(12) United States Patent
Kelly et al.

(10) Patent No.: US 7,625,753 B2
(45) Date of Patent: Dec. 1, 2009

(54) EXPANSION OF DEFINITIVE ENDODERM CELLS

(75) Inventors: Olivia Kelly, San Diego, CA (US); Emmanuel E. Baetge, Encinitas, CA (US); Melissa Carpenter, San Diego, CA (US)

(73) Assignee: Cythera, Inc., San Diego, CA (US)

( * ) Notice: Subject to any disclaimer, the term of this patent is extended or adjusted under 35 U.S.C. 154(b) by 228 days.

(21) Appl. No.: 11/317,387

(22) Filed: Dec. 22, 2005

(65) Prior Publication Data

US 2006/0148081 A1 Jul. 6, 2006

Related U.S. Application Data

(63) Continuation-in-part of application No. 11/021,618, filed on Dec. 23, 2004, now Pat. No. 7,510,876.

(60) Provisional application No. 60/736,598, filed on Nov. 14, 2005, provisional application No. 60/693,317, filed on Jun. 23, 2005, provisional application No. 60/587,942, filed on Jul. 14, 2004, provisional application No. 60/586,566, filed on Jul. 9, 2004, provisional application No. 60/532,004, filed on Dec. 23, 2003.

(51) Int. Cl.
*C12N 5/00* (2006.01)
*C12N 5/02* (2006.01)

(52) U.S. Cl. ...................................... 435/377; 435/374

(58) Field of Classification Search ............ 435/377, 435/374
See application file for complete search history.

(56) References Cited

U.S. PATENT DOCUMENTS

| | | | |
|---|---|---|---|
| 5,453,357 A | 9/1995 | Hogan | |
| 5,670,372 A | 9/1997 | Hogan | |
| 5,690,926 A | 11/1997 | Hogan | |
| 5,817,637 A | 10/1998 | Weiner et al. | |
| 5,830,876 A | 11/1998 | Weiner et al. | |
| 5,843,780 A | 12/1998 | Thomson | |
| 6,015,671 A | 1/2000 | Field | |
| 6,090,622 A | 7/2000 | Gearhart et al. | |
| 6,165,993 A | 12/2000 | Herrmann et al. | |
| 6,200,806 B1 | 3/2001 | Thomson | |
| 6,251,671 B1 | 6/2001 | Hogan et al. | |
| 6,261,281 B1 | 7/2001 | Mathiesen et al. | |
| 6,458,589 B1 | 10/2002 | Rambhatla et al. | |
| 6,506,574 B1 | 1/2003 | Rambhatla et al. | |
| 6,872,389 B1 | 3/2005 | Faris | |
| 6,921,811 B2 * | 7/2005 | Zamora et al. | 536/21 |
| 7,033,831 B2 | 4/2006 | Fisk et al. | |
| 7,153,684 B1 | 12/2006 | Hogan | |
| 7,256,042 B2 | 8/2007 | Rambhatla et al. | |
| 2002/0072117 A1 | 6/2002 | Xu et al. | |
| 2003/0138948 A1 | 7/2003 | Fisk et al. | |
| 2003/0138949 A1 | 7/2003 | Bhushan et al. | |
| 2003/0175956 A1 | 9/2003 | Bodnar et al. | |
| 2003/0190748 A1 | 10/2003 | Thomson | |
| 2003/0224411 A1 | 12/2003 | Stanton et al. | |
| 2004/0127406 A1 * | 7/2004 | Presnell et al. | 514/12 |
| 2004/0229350 A1 | 11/2004 | Strelchenko et al. | |
| 2006/0003446 A1 | 1/2006 | Keller et al. | |
| 2006/0019387 A1 | 1/2006 | Faris | |
| 2006/0040385 A1 | 2/2006 | Itskovitz-Eldor et al. | |
| 2006/0040387 A1 | 2/2006 | Fisk et al. | |
| 2006/0128017 A1 | 6/2006 | Zwaka et al. | |
| 2006/0276420 A1 * | 12/2006 | Keller et al. | 514/44 |
| 2007/0281355 A1 | 12/2007 | Dalton et al. | |

FOREIGN PATENT DOCUMENTS

| | | |
|---|---|---|
| EP | 1298201 A | 4/2003 |
| WO | WO 98/30679 | 7/1998 |
| WO | WO 99/13915 | 3/1999 |
| WO | WO 00/29442 | 5/2000 |
| WO | WO 02/10347 | 2/2002 |
| WO | WO 02/059278 | 8/2002 |
| WO | WO 03/050249 A2 | 6/2003 |
| WO | WO 03/050249 A3 | 6/2003 |
| WO | WO 03/100026 | 12/2003 |
| WO | WO 2004/098490 | 11/2004 |
| WO | WO 2005/017131 | 2/2005 |
| WO | WO 2005/033294 | 4/2005 |
| WO | WO 2005/045001 | 5/2005 |
| WO | WO 2005/063971 | 7/2005 |
| WO | WO 2005/097980 A2 | 10/2005 |
| WO | WO 2005/116073 | 12/2005 |
| WO | WO 2006/016999 | 2/2006 |
| WO | WO 2006/017134 | 2/2006 |
| WO | WO 2006/020919 A2 | 2/2006 |
| WO | WO 2007/002210 A2 | 1/2007 |

OTHER PUBLICATIONS

McGrath et al., Embryonic expression and function of the chemokine SDF-1 and its receptor, CXCR4. Dev Biol. 213(2): 442-56, 1999.*
Czyz et al., Embryonic stem cell differentiation: the role of extracellular factors. Differentiation. 68(4-5): 167-74, 2001.*
Mclean et al., Activin A efficiently specifies definitive endoderm from human embryonic stem cells only when phosphatidylinositol 3-kinase signaling is suppressed, Stem Cells, 25(1): 29-38, 2007.*
Tam et al., Early endoderm development in vertebrates: lineage differentiation and morphogenetic function. Curr Opin Genet Dev. 13(4): 393-400, 2003.*

(Continued)

*Primary Examiner*—Deborah Crouch
*Assistant Examiner*—Wu-Cheng Winston Shen
(74) *Attorney, Agent, or Firm*—Knobbe Martens Olson & Bear LLP

(57) ABSTRACT

Disclosed herein are cell cultures comprising expanded definitive endoderm cells as well as methods for expanding definitive endoderm cells in culture.

40 Claims, 39 Drawing Sheets

OTHER PUBLICATIONS

Yusuf et al. Expression of chemokine receptor CXCR4 during chick embryo development. Anat Embryol (Berl). 210(1): 35-41, 2005.*
Assady et al. "Insulin production by human embryonic stem cells" (2001)*Diabete* 50(8):1691-1697.
Collumbat, et al., Specifying pancreatic endocrine cell fates. Mech Dev. 123(7): 501-12, 2006.
Conley et al. "BMPs Regulate Differentiation of a Putative Visceral Endoderm Layer Within Human Embryonic Stem-Cell-Derived Embryoid Bodies" (2007) *Biochem Cell Biol* 85: 121-132.
Daheron et al. "LIF/STAT3 Signaling Fails to Maintain Self-Renewal of Human Embryonic Stem Cells" *Stem Cells* 22, 770-8 (2004).
D'Amour et al. "Production of pancreatic hormone-expressing endocrine cells from human embryonic stem cells" (Nov. 1, 2006) *Nature Biotechnology* 24, 1392-1401.
Holland, et al. Experimental control of pancreatic development and maintenance. Proc Natl Acad Sci USA 2002; 99(19):12 236-12 241.
Humphrey et al. "Maintenance of Pluripotency in Human Embryonic Stem Cells Is STAT3 Independent" (2004) *Stem Cells* 22, 522-30.
Jones et al. "Differences Between Human and Mouse Alpha-Fetoprotein Expression During Early Development" (2001) *J. Anat.* 198: 555-9.
Keller, G.M. "In vitro differentiation of embryonic stem cells" (1995)*Curr Op Cell Biol* 7:862-896.
Matsuda T, et al. "STAT3 Activation is Sufficient to Maintain an Undifferentiated State of Mouse Embryonic Stem Cells" (Aug. 2, 1999) *EMBO J*, 18(15):4261-9.
McGrath, et al. "Expression of Homeobox Genes, including an Insulin Promoting Factor, in the Murine Yolk Sac and the Time of Hematopoietic Initiation" (1997) *Mol Reprod Dev* 48: 145-153.
McLean et al. "Activin A Efficiently Specifies Definitive Endoderm from Human Embryonic Stem Cells Only When Phosphtidylinositol 3-Kinase Signaling Is Suppressed" (2007) *Stem Cells* 25: 29-38.
Millonig, et al. "Molecular Analysis of the Distal Enhancer of the Mouse Alpha-Fetoprotein Gene" (1995) *Mol. Cell Biol*. 15: 3848-3856.
Roche et al. "Ectodermal commitment of insulin-producing cells derived from mouse embryonic stem cells" *Faseb J* (2005) 19: 1341-3.
Urbach et al. "Modeling Lesch-Nyhan Disease by Gene Targeting in Human Embryonic Stem Cells" (2004) *Stem Cells* 22:635-641.
Vallier et al. "Nodal Inhibits Differentiation of Human Embryonic Stem Cells Along the Neuroectodermal Default Pathway" (2004) *Developmental Biology* 275, 403-421.
Vallier et al. "Activin/Nodal and FGF Pathways Cooperate to Maintain Pluripotency of Human Embryonic Stem Cells" (2005) *J Cell Sci*. 118: 4495-509.
Wei et al. "Transcriptome Profiling of Human and Murine ESCs Identifies Divergent Paths Required to Maintain the Stem Cell State"(2005) *Stem Cells* 23:166-185.
Wilding, et al., The role of pdx1 and HNF6 in proliferation and differentiation of endocrine precursors. Diabetes Metab Res Rev 20(2)114-23, 2004.
Zwaka, et al. "Homologous Recombination in Human Embryonic Stem Cells" *Nature Biotechnology* (2003) vol. 21.
Bendall, et al. "IGF and FGF Cooperatively Establish Regulatory Stem Cell Niche of Pluripotent Human Cells In Vitro." Nature (2007), 448; 1015-1021.
Freund, et al. "Insulin Redirect Differentiation from Cardiogenic Mesoderm and Endoderm to Neuroectoderm in Differentiating Human Embryonic Stem Cells," Stem Cells (2007), published online Dec. 20, 2007.
Rambhatla et al. "Generation of Hepatocyte-Like Cells From Human Embryonic Stem Cells." Cell Transplantation (2003), vol. 12, No. 1, p. 1-11.
Segev, Hanna et al. "Differentiation of human embryonic stem cells into insulin-producing clusters." Stem Cells (Dayton, Ohio) 2004, vol. 22, No. 3, 2004, pp. 265-274.
Shi, Yan, et al. "Inducing embryonic stem cells to differentiate into pancreatic beta cells by a novel three-step approach with activin A and all-trans retinoic acid." Stem Cells (Dayton, Ohio) May 2005, vol. 23, No. 5, pp. 656-662.

Wang, et al. "Self-Renewal of Human embryonic Stem Cells Requires Insulin-Like Growth Factor-1 Receptor and ERBB2 Receptor Signaling." Blood (2007), 110; 4110-4119.
Xu, et al. "BMP4 Initiates Human Embryonic Stem Cell Differentiation to Trophoblast." Nature Biotechnology (Dec. 2002), vol. 20, pp. 1261-1264.
Ying, et al. "BMP Induction of Id Proteins Suppresses Differentiation and Sustains Embryonic Stem Cell Self-Renewal in Collaboration with STAT3." Cell (Oct. 31, 2003), vol. 115, pp. 281-292.
Abe K et al., "Endoderm-Specific Gene Expression in Embryonic Stem Cells Differentiated to Embryoid Bodies." Experimental Cell Research. vol. 229, No. 1, p. 27-34, 1996.
Alexander, J., and Stainier, D.Y. (1999). A molecular pathway leading to endoderm formation in zebrafish. Curr Biol 9, 1147-1157.
Alexander, J., Rothenberg, M., Henry, G.L., and Stainier, Dn. (1999). Casanova plays an early and essential role in endoderm formation in zebrafish. Dev Biol 215, 343-357.
Ang et al., "The Formation and Maintenance of the Definitive Endoderm Lineage in the Mouse: Involvement of HNF3/forkhead Proteins." Development, 119:1301-1315. (1993).
Aoki, T.O., Mathieu, J., Saint-Etienne, L., Rebagliati, M.R., Peurieras, N., and Rosa, F. M. (2002). Regulation of nodal signalling and mesendoderm formation by TARAM-A, a TGFbeta-related type I receptor. Dev Biol 241, 273-288.
Bain et al., "Embryonic Stem Cells Express Neuronal Properties in Vitro." Developmental Biology. 168:342-357 (1995).
Barry et al. <<Production of monoclonal antibodies by genetic immunization.>>Biotechniques 16 : 616-620. (1994).
Beck, S., Le Good, J.A., Guzman, M., Ben Haim, N., Roy, K., Beermann, F., and Constam, D.B. (2002). Extra-embryonic proteases regulate Nodal signaling during gastrulation. Nat Cell Biol 4, 981-985.
Beddington, R.S., Rashbass, P., and Wilson, V. (1992). Brachyury—a gene affecting mouse gastrulation and easly organogenesis. Day Suppl, 157-165.
Bongso. A., Fong, C.V., Ng, S.C., and Ratnam, S. (1994). Isolation and culture of inner cell mass cells from human blastocysts. Hum Reprod 9, 2110-2117.
Bost et al., "Retinoic Acid Activation of the ERK Pathway is Required for Embryonic Stem Cell Commitment into the Adipocyte Lineage." Biochem. J. 361:621-627. (2002).
Chang, H., Brown, C.W., and Matzuk, M.M (2002). Genetic analysis of the mammalian transforming growth factor-beta superfamily. Endocr Rev 23, 787-823.
Conlon, F.L., Lyons, K.M., Takaesu, N., Barth, K.S., Kispert, A., Herrmann, B., and Robertson, E.J. (1994). A primary requirement for nodal in the formation and maintenance of the primitive streak in the mouse. Development 120, 1919-1928.
Costaglia et al. (1998) Genetic immunization against the human thyrotropin receptor causes thyroiditis and allows production of monoclonal antibodies recognizing the native receptor. J. Immunol. 160:1458-1465.
D'Amour Kevin A. et al., "Efficient differentiation of human embryonic stem cells to definitive endoderm." Nature Biotechnology, Dec. 2005, vol. 23, No. 12, pp. 1534-1541.
Dani et al., "Differentiation of Embryonic Stem Cells into Adipocytes in Vitro." Journal of Cell Science. 110:1279-1285. (1997).
Dougan, St., Warga, R.M., Kane, D.A., Schier, A.F., and Talbot, W.S. (2003). The role of the zebrafish nodal-related genes squint and Cyclops in patterning of mesendodernri. Development 130, 1837-1851.
Defelice Mario et al., "TTF-1 Phosphorylation is required for peripheral lung Morphogenesis, Perinatal Survival, and Tissue-Specific Gene Expression." The Journal of Biological Chemistry. 278:37, pp. 35574-35583. (2003).
Edlund, H., "Factors Controlling Pancreatic Cell Differentiation and Function," Diabetologia, Sep. 2001, vol. 44, No. 9, pp. 1071-1079.
Falasca, L. et al., "Retinoic Acid Treatment Induces Apoptosis or Expression of a More Differentiated Phenotype on Different Fractions of Cultured Fetal Rat Hepatocytes Hepatology," 1998, vol. 28, No. 3, pp. 727-737.

Fehling et al., "Development and Disease: Tracking Mesoderm Induction and its Specification to the Hemangioblast during Embryonic Stem Cell Differentiation." Development. 130:4217-4227, (2003).

Feldman, B., Gates, M.A., Egan, E.S., Dougan, S.T., Rennebeck, G., Sirotkin, H. I., Schier, A.F., and Talbot, W.S. (1998). Zebrafish organizer development and germ-layer formation require nodal-related signals. Nature 395, 181-185.

Feng, Y., Broder, C.C., Kennedy, P.E., and Berger, E.A. (1996). HIV-1 entry cofactor: functional cDNA cloning of a seven-transmembrane, G protein-coupled receptor, Science 272, 872-877.

Futaki, S., Hayashi, Y., Yamashita, M., Yagi, K., Bono, H., Hayashizaki, Y., Okazaki, Y., and Sekiguchi, K. (2003). Molecular basis of constitutive production of basement membrane components: Gene expression profiles of engelbreth-holm-swarm tumor and F9 embryonal carcinoma cells. J Biol. Chem.

Goumans et al., "Mouse Embryonic Stem Cells with Aberrant Transforming Growth Factor B signaling Exhibit Impaired Differentiation in Vitro and In Vivo." Differentiation. 63:103-113. (1998).

Grapin-Botton, A., and Melton, D. A. (2000). Endoderm development: from patterning to organogenesis. Trends Genet 16, 124-130.

Hamazaki et al. "Hepatic Maturation in Differentiating Embryonic Stem Cells in Vitro." Febs Letter, Elsevier Science Publishers, Amsterdam, NL, vol. 497, No. 1: 15-19, May 18, 2001.

Harris, T. M., and Childs, G. (2002). Global gene expression patterns during differentiation of F9 embryonal carcinoma cells into parietal endoderm. Funct Integr Geneomics 2, 105-119.

Hogan, B.L. (1996). Bone morphogenetic proteins in development. Curr Opin Genet Dev 6, 432-438.

Howe, C.C., Overton, G.C., Sawicki, J., Solter, D., Stein, P., and Strickland, S. (1988). Expression of SPARC/osteonectin transcript in murine embryos and gonads. Differentiation 37, 20-25.

Hudson, C., Clements, D., Friday, R. V., Stott, D., and Woodland, H.R. (1997). Xsox17alpha and—beta mediate endoderm formation in Xenopus. Cell 91, 397-405.

Imada, M., Imada, S., Iwasaki, H., Kume, A., Yamaguchi, H., and Moore, E.E. (1987). Fetomodulin: Marker surface protein of fetal development which is modulatable by cyclic Amp. Dev Biol 122, 483-491.

Jain, K. et al., "Glucose Control and Long-Term Survival in Breeding/Worcester Rats After Intraperitoneal Implantation of Hydrophilic Macrobeads containing Porcine Islets without Immunosuppression," Transplantation, 1999, vol. 68, No. 11, pp. 1693-1700.

Kahan, B.W., et al. "Pancreatic Precursors and Differentiated Islet Cell Types from Murine Embryonic Stem Cells: An In Vitro Model to Study Islet Differentiation." Diabetes. Aug. 2003, vol. 52, No. 8, pp. 2016-2024.

Kanai-Azuma, M., Kanai, Y., Gad, J.M., Tajima, Y., Taya, C., Kurohmaru, M., Sanai, Y., Yonekawa, H., Yazaki, K., Tam, P.P., and Hayashi, Y. (2002). Depletion of definitive gut endoderm in Sox17-null mutant mice. Development 129, 2367-2379.

Katoh, M. (2002). Expression of human SOX7 in normal tissues and tumors. Int J Mol Med 9, 363-368.

Kieffer, T.J., and J.F. Habener, "The Glucagon-Like Peptides," Endocrinology Reviews, Dec. 1999, vol. 20, No. 6, pp. 876-913.

Kikuchi, Y., Agathon, A., Alexander, J., Thisse, C., Waldron, S., Yelon, D., Thisse, B., and Stainier, D.Y. (2001). Casanova encodes a novel Sox-related protein necessary and sufficient for early endoderm formation in zebrafish. Genes Dev 15, 1493-1505.

Kilpatrick et al. (1998). Gene gun delivered DNA-based immunizations mediate rapid production of murine monoclonal antibodies to the Flt-3 receptor. Hybridoma 17: 569-576.

Kim, C.H., and Brozmeyer, H.E. (1999). Chemokines: signal lamps for trafficking of T and B cells for development and effector function. J Leukoc Biol 65, 6-15.

Grapin-Botton, A., and Melton, D. A. (2000). Endoderm development from patterning to organogenesis. Trends Genet 16, 124-130.

Hamazaki et al. "Hepatic Maturation in Differentiating Embryonic Stem Cells in Vitro." Febs Letter, Elsevier Science Publishers, Amsterdam, NL, vol. 497, No. 1: 15-19.

Harris, T. M., and Childs, G. (2002). Global gene expression patterns during differentiation of F9 embryonal carcinoma cells into parietal endoderm. Funct Integr Geneomics 2, 105-119.

Hogan, B.L (1996). Bone morphogenetic proteins in development. Cuff Opin Genet Dev 6, 432-438.

Hovve, C.C., Overton, G.C., Sawicki, J., Solter, D., Stein, P., and Strickland, S. (1988). Expression of SPARC/osteonectin transcript in murine embryos and gonads. Differentiation 37, 20-25.

Kanai-Azuma, M., Kenai, Y., Gad, J.M., Tajima, Y., Taya, C., Kurohrnaru, M., Sanai, Y., Yonekawa, H., Yazaki, K., Tam, P.P., and Hayashi, Y. (2002). Depletion of definitive gut endoderm in Sox17-null mutant mice. Development 129, 2367-2379.

Kimelman, D., and Griffin, K. J. (2000). Vertebrae mesendoderm induction and patterning, Curr Opin Genet Dev 10, 350-356.

Krasemann et al. (1999). Generation of monoclonal antibodies against proteins with an unconventional nucleic acid-based immunization strategy. J. Biotechnol. 73: 119-129.

Kubo, A., Shinozaki, K., Shannon, J, M., Kouskoff, V., Kennedy, M., Woo, S., Fehlong, H.J., and Keller, G. (2004). Development of definitive endoderm from embryonic stem cells in culture. Development 131, 1651-1652.

Kumar, A., Novoselov, V., Celeste, A. J., Wolfman, N.M., ten Dijke, P., and Kuehn, M. R. (2001). Nodal signaling uses activin and transforming growth factor-beta receptor-regulated Smads. J Biol Chem 276, 658-661.

Labosky, P.A., Barlow, D. P., and Hogan, B. L. (1994). Embryonic germ cell lines and their derivation from mouse primordial germ cells. Ciba Found Symp 182, 157-168; discussion 168-178.

Labosky, P.A., Barlow, D. P., and Hogan, B. L. (1994). Mourse embryonic germ (EG) cell lines: transmission through the germline and differences in the methylation imprint of insulin-like growth factor 2 receptor (Igf2r) gene compared with embryonic stem (ES) cell lines. Development 120, 3197-3204.

Latif, Z.A. et al., "A Simple Method of Staining Fresh and Cultured Islets," Transplantation, 1998, vol. 45, No. 4, pp. 827-830.

Lickert, H., Kutsch, S., Kanzler, B., Tamai, Y., Taketo, M.M., and Kemler, R. (2002). Formation of multiple hearts in mice following deletion of beta-catenin in the embryonic endoderm. Dev Cell 3, 171-181.

Lu, C.C., Brennanm J., and Robertson, E. J., (2001). From fertilization to gastrulation: axis formation in the mouse embryo. Curr Opin Genet Dev 11, 384-392.

Lumelsky, N. et al., "Differentiation of Embryonic Stem Cells to Insulin-Secreting Structures Similar to Pancreatic Islets," Science vol. 292, pp. 1389-1394 (2001).

Micallef Suzanne, et al. "Retinoic Acid Induces Pdx1-positive Endoderm in Differentiating mouse embryonic stem cells." Diabetes. Feb. 2005, vol. 54, No. 2, pp. 301-305.

Ma, Q., Jones, D., and Springer, T. A. (1999). The chemokine receptor CXCR4 is required for the retention of B lineage and granulocytic precursors within the bone marrow microenvironment, Immunity 10, 463-471.

McGrath, K.E., Koniski, A. D., Maltby, K. M., McGann, J.K. and Palis, J. (1999). Embryonic expression and function of the chemokine SDF-1 and its receptor, CXCR4. Dev Biol. 213, 442-456.

Miyazono, K., Kusanagi, K., and Inoue, H. (2001). Divergence and convergenence of TGF-beta/BMP signaling. J Cell Physiol 187, 265-276.

Mizusawa et al., "Differentiation Phenotypes of Pancreatic Islet Beta- and Alpha-Cells are Closely Related with Homeotic Genes and a Group of Defferentially Expressed Genes." Gene: An Int. Journal on Genes and Genomes. 331:53-63. (2004).

Moriya, N. et al., "In Vitro Pancreas Formation from *Xenopus* Ectoderm Treated with Activin and Retinoic Acid," Develop. Growth Differ., vol. 42, pp. 593-602 (2000).

Nagasawa, T., Hirota, S., Tachibaba, K., Takakura, N., Nichikawa, S., Kitamura, Y., Yoshida, N., Kikutani, H., and Kishimito, T. (1996). Defects of B-cell lymphopoiesis and bone-marrow myelopoiesis in mice lacking the CXC chemokine PBSF/SDF-1. Nature 382, 635-638.

Niwa, H. (2001). Molecular mechanism to maintain stem cell renewal of ES cells, Cell Struct Funct 26, 137-148.

O'Hare, M.J. et al., "Conditional Immortilization of Freshly Isolated Human Mammary Fibroblast and Endothelial Cells," Proc. Nat. Acad. Sci., vol. 98, pp. 646-651 (2001).

Ogura, H., Aruga, J., and Mikoshiba, K. (2001). Behavioral abnormalities of Zic1 and Zic2 mutant mice: implications as models for human neurological disorders, Behav Genet 31,317-324.

Phillips at al., "Differentiation of Embryonic Stem Cells for Pharmacological Studies on Adipose Cells." Pharmacological Research. 47:263-268. (2003).

Reubinoff, B.E., Pera, M.F., Fong, C.Y. Tounson, A., and Bongso, A. (2000). Embryonic stem cell lines from human blastocysts: somatic differentiation in vitro. Nat Biotechnol 18, 399-404.

Rodaway, A., and Patient, R. (2001). Mesendoderm, an ancient germ layer? Cell 105, 169-172.

Rodaway, A., Takeda, K., Koshida, S., Broadbent, J., Price, B., Smith, J.C., Patient, R., and Holder, N. (1999). Induction of the mesendoderm in the zebrafish germ ring by yolk cell-derived TGF-beta family signals and discrimination of mesoderm and endoderm by FGF. Development 126, 3067-3078.

Rohr, K.B., Schulte-Merker, S., and Tautz, D. (1999). Zebrafish zic1 expression in brain and somites is affected by BMP and hedgehog signaling. Mech Dev 85, 147-159.

Sander, M. and M.S. German, "The Beta Cell Transcription Factors and Development of the Pancreas," Journal of Molecular Medicine, May 1997, vol. 75, No. 5, pp. 327-340.

Schier, A. F. (2003). Nodal signaling in vertebrae development Annu Rev Cell Dev Biol 19, 589-621.

Schmolke et al. (1998). Identification of hepatitis G virus particles in human serum by E2-specific monoclonal antibodies generated by DNA immunization. J. Virol. 72: 4541-4545.

Schoenwolf, G.C., and Smith, J. L. (2000). Gastrulation and early mesodermal patterning in vertebrates. Methods Mol Biol 135, 113-125.

Schuldiner et al. (2000). Effects of Eight Growth Factors on the Differentiation of Cell Derived from Human Embryonic Stem Cells. Proc. Natl. Sci., vol. 97, 11307-11312.

Shamblott, M.J., Axelman, J., Wang, S., Bugg, E. M., Littlefield, J.W., Donovan, P. J., Blumenthal, P. D., Huggins, G. R., and Gearhart, J.D. (1998). Derivation of pluripotent stem cells from cultured human primordial germ cells. Proc Natl Acad Sci USA 95, 13726-13731.

Shapiro, A. M., Lakey, J.R., Ryan, E. A., Korbuttm G. S., Toth, E., Warnock, G. L., Kneteman, N.M., and Rajotte, R. V. (2000). Islet transplantation in seven patients with type 1 diabetes mellitus using a glucocorticoid-free immunosuppressive regimen. N Engl J Med 343, 230-238.

Shapiro, A. M., Ryan, E. A., and Lakey, J. R. (2001) Pancreatic islet transmplantation in the treatment of diabetes mellitus. Best Pract Res Clin Endocrinol Metab 15, 241-264.

Shapiro, J., Ryan, E., Warnock, G. L., Kneteman, N. M., Lakey, J., Korbutt, G. S., and Rajotte, R. V. (2001) Could fewer islet cells be transplanted in type 1 diabetes? Insulin independence should be dominant force in islet transplantation. Bmj 322, 861.

Shiozawa, M., Hiraoka, Y., Komatsu, N., Ogawa, M., Sakai, Y., and Also, D. (1996). Cloning and characterization of Xenopus laevis xSox 7 xDNA. Biochim Biophys Ada 1309, 73-76.

Skoudy, A., et al. "Transforming Growth Factor (TGF) beta, Fibroblast Growth Factor (FGF) and Retinoid Signaling Pathways Promote Pancreatic Exocrine Gene Expression in Mouse Embryonic Stem Cells". The Biochemical Journal. May 1, 2004, vol. 379, No. Pt 3, pp. 749-756.

Smith, J. (1997). Brachyury and the T-box genes. Curr Opin Genet Dev 7, 474-480.

Smith, J. C., Armes, N. A., Conlon, F. L., Tada, M., Umbhauer, M., and Weston, K.M. (1997). Upstream and downstream from Brachyury, a gene required for vertebrae mesoderm formation. Cold Springs Herb Symp Quant Biol 62, 337-346.

Soon-Shiong, P., "Treatment of Type I Diabetes using Encapsulated Islets," Advanced Drug Delivery Reviews, 1999, vol. 35, pp. 259-270.

Soria, et al. "Insulin-Secreting Cells Derived from Embryonic Stem Cells Normalize Glycemla in Streptozotocin-lnduced Diabetic Mice." Diabetes, New York, NY, vol. 49, No. 2: 157-162.

Stafford, D. and Prince, V. (2001). Pancreatic Development, Proliferation and Stem Cells. Meeting Abstract, Oct. 18-19, National Institute of Health.

Stafford, D. and Prince, V. (2002). Retinoic Acid Signaling Is Required for a Critical Early Step in Zebrafish Pancreatic Development, Current Biology, vol. 12, 1215-1220, Jul. 23, 2002.

Suzuki, M. et al: Cloned Cells Develop Renal Cortical Collecting Tubles. Nephron. 1994, vol. 68, pp. 118-124.

Takash, W., Canizares, J., Bonneaud, N., Poulat, F., Mattei, M.G., Jay, P., and Berta, P. (2001). SOX7 transcription factor: sequence, chromosomal localization, expression, transactivation and interference with Wnt signaling. Nucleic Acids Res 29, 4274-4283.

Taniguchi, K., Hiraoka, Y., Ogawa, M.,Sakal, Y., Kldo, S., and Also, S. (1999). Isolation and characterization of a mouse SRY-related cDNA, mSox7. Biochim Biophys Act 1445, 225-231.

Technau, U. (2001). Brachyury, the blastopore and the evolution of the mesoderm. Bioassays 23, 788-794.

Tiedemann et al., "Pluripotent cells (stem cells) and Their Determination and Differentiation in Early Vertebrate Embryogenesis." Develop. Growth Differ. 43:469-502, (2001).

Thomson, J.A., Itskovitz-Eldor, J., Shapiro, S. S., Waknitz, M. A., Swiergiel, J. J., Marshall, V. S., and Jones, J. M. (1998). Embryonic stem cell lines derived from human blastocysts, Science 282, 1145-1147.

Tremblay, K. D., Hoodless, P. A., Bikoff, E. K., and Robertson, E. J. (2000). Formation of the definitive endoderm in mouse is a Smad2-dependent process. Development 127, 3079-3090.

Ulivieri et al. (1996). Generation of a monoclonal antibody to a defined portion of the Heliobacter pylori vacuolating cytotoxin by DNA immunization. J. Biotechnol. 51: 191-194.

Soria, et al. "Insulin-Secreting Cells Derived from Embryonic Stem Cells Normalize Glycemia in Streptozotocin-Induced Diabetic Mice." Diabetes, NewYork, NY, vol. 49, No. 2: 157-162. (Feb. 2000).

Vandesompele, J., De Prefer, K., Pattyn, F., Poppe, B., Van Roy, N., De Paepe, A., and Speleman, F. (2002). Accurate normalization of real-time quantitative RT-PCR data by geometric averaging of multiple internal control genes. Genome Biol 3, RESEARCH0034.

Varlet, I., Collignon, J., and Robertson, E. J. (1997). Nodal expression in the primitive endoderm is required for specification of the anterior axis during mouse gastrulation. Development 124, 1033-1044.

Vincent, S. D., Dunn, N. R., Hayashi, D. P., and Robertson, E. J, (2003). Cell fate decisions within the mouse organizer are governed by graded nodal signals. Genes Dev 17, 1646-1662.

Vogel, G. Stem Cells are Coaxed to Produce Insulin, Science. Apr. 27, 2001, vol. 292, pp. 615-616.

Weiler-Guettler, H., Aird, W. C., Raybum, H., Husain, M., and Rosenberg, R. D. (1996). Developmentally regulated gene expression of thrornbomodulin in postimplantation mouse embryos. Development 122, 2271-2281.

Weiler-Guettler, H., Yu, K., Soff, G., Gudas, L. J., and Rosenberg, R. D. (1992). Thrombomodulatin gene regulation by cAMP and retinoic acid in F9 embryonal carcinoma cells. Proceedings of the National Academy of Sciences of the United States of America 89, 2155-2159.

Wells, J.M., and Melton, D. A. (1999). Vertebrate endoderm development. Annu Rev Cell Dev Biol 15, 393-410.

Wells, J.M., and Melton, D.A. (2000). Early mouse endoderm is patterned by soluble factors from adjacent germ layers. Development 127, 1563-1572.

Willison, K. (1990). The mouse Brachyury gene and mesoderm formation. Trends Genet 6, 104-105.

Xu et al., "Characterization and Enrichment of Cardiomyocytes Derived From Human Embryonic Stem Cells." Cellular Biology. 91:501-508. (2002).

Yasunaga Masahiro et al., "Induction and monitoring of definitive and visceral endoderm differentiation of mouse ES cells." Nature Biotechnology. Dec. 2005, vol. 23, No. 12, pp. 1542-1550.

Zhao, G. Q. (2003). Consequences of knocking out BMP signaling in the mouse. Genesis 35, 43-56.

Zhou, X., Sasaki, H., Lowe, L., Hogan, B.L., and Kuehn, M. R. (1993). Nodal is a novel TGF-beta-like gene expressed in the mouse node during gastrulation. Nature 361, 543-547.

International Search Report from PCT/US2005/047175 dated Dec. 22, 2005.

* cited by examiner (+) Activin A (B)

6.8-fold difference (−) Activin A (A)

(A)

(B)

(C)

(A)

(B)

(A)

(B)

(C)

G  H  I

J  K  L

EXPANSION OF DEFINITIVE ENDODERM CELLS

RELATED APPLICATIONS

This application is a nonprovisional application of and claims priority to U.S. Provisional Patent Application No. 60/693,317, entitled EXPANSION OF ISOLATED DEFINITIVE ENDODERM CELLS, filed Jun. 23, 2005 and a nonprovisional application of and claims priority to U.S. Provisional Patent Application No. 60/736,598, entitled MARKERS OF DEFINITIVE ENDODERM, filed Nov. 14, 2005; this application is also a continuation-in-part of and claims priority to U.S. patent application Ser. No. 11/021,618, entitled DEFINITIVE ENDODERM, filed Dec. 23, 2004, now U.S. Pat. No. 7,510,876 which claims priority under 35 U.S.C. § 119(e) as a nonprovisional application to U.S. Provisional Patent Application No. 60/587,942, entitled CHEMOKINE CELL SURFACE RECEPTOR FOR THE ISOLATION OF DEFINITIVE ENDODERM, filed Jul. 14, 2004; U.S. Provisional Patent Application No. 60/586,566, entitled CHEMOKINE CELL SURFACE RECEPTOR FOR THE ISOLATION OF DEFINITIVE ENDODERM, filed Jul. 9, 2004 and U.S. Provisional Patent Application No. 60/532,004, entitled DEFINITIVE ENDODERM, filed Dec. 23, 2003.

FIELD OF THE INVENTION

The present invention relates to the fields of medicine and cell biology. In particular, the present invention relates to compositions of definitive endoderm cells which have been expanded either prior to or subsequent to enrichment, isolation and/or purification as well as methods of producing and using such cells.

BACKGROUND

Human pluripotent stem cells, such as embryonic stem (ES) cells and embryonic germ (EG) cells, were first isolated in culture without fibroblast feeders in 1994 (Bongso et al., 1994) and with fibroblast feeders (Hogan, 1997). Later, Thomson, Reubinoff and Shamblott established continuous cultures of human ES and EG cells using mitotically inactivated mouse feeder layers (Reubinoff et al., 2000; Shamblott et al., 1998; Thomson et al., 1998).

Human ES and EG cells (hESCs) offer unique opportunities for investigating early stages of human development as well as for therapeutic intervention in several disease states, such as diabetes mellitus and Parkinson's disease. For example, the use of insulin-producing β-cells derived from hESCs would offer a vast improvement over current cell therapy procedures that utilize cells from donor pancreases for the treatment of diabetes. However, presently it is not known how to generate an insulin-producing β-cell from hESCs. As such, current cell therapy treatments for diabetes mellitus, which utilize islet cells from donor pancreases, are limited by the scarcity of high quality islet cells needed for transplant. Cell therapy for a single Type I diabetic patient requires a transplant of approximately $8 \times 10^8$ pancreatic islet cells. (Shapiro et al., 2000; Shapiro et al., 2001a; Shapiro et al., 2001b). As such, at least two healthy donor organs are required to obtain sufficient islet cells for a successful transplant. Human embryonic stem cells offer a source of starting material from which to develop substantial quantities of high quality differentiated cells for human cell therapies.

Two properties that make hESCs uniquely suited to cell therapy applications are pluripotence and the ability to maintain these cells in culture for prolonged periods. Pluripotency is defined by the ability of hESCs to differentiate to derivatives of all 3 primary germ layers (endoderm, mesoderm, ectoderm) which, in turn, form all somatic cell types of the mature organism in addition to extraembryonic tissues (e.g. placenta) and germ cells. Although pluripotency imparts extraordinary utility upon hESCs, this property also poses unique challenges for the study and manipulation of these cells and their derivatives. Owing to the large variety of cell types that may arise in differentiating hESC cultures, the vast majority of cell types are produced at very low efficiencies in mixed cell populations. In order to use hESCs as a starting material to generate cells that are useful in cell therapy applications, it would be advantageous to overcome the foregoing problems.

SUMMARY OF THE INVENTION

Embodiments of the present invention relate to cell cultures comprising expanded definitive endoderm cells. Further embodiments described herein relate to methods for expanding enriched, isolated and/or purified definitive endoderm cells in culture.

Some of the methods described herein relate to the maintenance, growth, passage and/or expansion of definitive endoderm cells in cell culture. In such embodiments, cell cultures comprising definitive endoderm cells are obtained. The cells are then isolated so that at least some of the definitive endoderm cells are separated from at least some of the other cells in the cell culture, thereby producing a cell population that is enriched in definitive endoderm cells. In some embodiments, the enriched cell populations of definitive endoderm cells are cultured under conditions that permit the expansion of the definitive endoderm cells.

In other embodiments of the methods described herein, the definitive endoderm cells are multipotent cells that can differentiate into cells of the gut tube or organs derived therefrom. In preferred embodiments, the definitive endoderm cells are human definitive endoderm cells that are obtained by differentiating human embryonic stem cells (hESCs). In such embodiments, definitive endoderm cells can be derived from hESCs by contacting such cells with at least one growth factor from the TGFβ superfamily, such as activin A. In other embodiments, human and/or other definitive endoderm cells can be obtained from a pre-existing culture of definitive endoderm cells. In such embodiments, either a portion of or the entire culture may be used in the definitive endoderm expansion methods described herein.

In addition to obtaining cell cultures comprising definitive endoderm cells, some embodiments of the expansion methods described herein also comprise the step of producing enriched definitive endoderm cell populations. In some embodiments, such enriched definitive endoderm cell populations are produced by separating at least some of the definitive endoderm cells from at least some of the other cells in the cell cultures. As such, the at least some of the definitive endoderm cells are isolated from at least some of the other cells which remain in the cell culture. In some embodiments, the isolating step comprises providing the cells in the cell culture with a reagent which binds to a marker expressed in said definitive endoderm cells but which is not substantially expressed in said other cells present in the cell culture. The reagent-bound definitive endoderm cells are then separated from the non-reagent-bound cells, thereby producing an enriched definitive endoderm cell population. In some embodiments, the marker is CXCR4 and the reagent is an antibody with an affinity for CXCR4. In some embodiments, the definitive endoderm cells are separated by fluorescence activated cell sorting (FACS).

In still other embodiments, at least some of the definitive endoderm cells are separated from at least some of the other cells in the culture by specifically fluorescently labeling the definitive endoderm cells in culture and then separating the labeled cells from the unlabeled cells by FACS. In some embodiments, the fluorescence is produced by green fluorescent protein (GFP) or enhanced green fluorescent protein (EGFP). In some embodiments, the GFP and/or EGFP is expressed under the control of the SOX17 or the CXCR4 promoter.

In some embodiments, the enriched definitive endoderm cell populations that are produced as described above are substantially free of cells other than definitive endoderm cells. In other embodiments, the enriched definitive endoderm cell populations comprise from at least about 96% to at least about 100% definitive endoderm cells.

Additional embodiments of the methods described herein also include a culturing step that comprises plating the population enriched in definitive endoderm cells or a portion of the population. In some embodiments, the cells are plated on a surface coated with human fibronectin and/or poly-ornithine. In other embodiments, the culturing step comprises incubating the enriched definitive endoderm cell population or portion thereof in a medium comprising about 2% (v/v) serum. In some embodiments, the medium also comprises at least one growth factor. In certain embodiments, the at least one growth factor is a growth factor comprises a member of the TGFβ superfamily, such as activin A. Alternatively, the growth factor can be IGF1, bFGF, EGF or another growth factor. In such embodiments, the growth factor can be present in the medium at a concentration ranging from about 1 ng/ml to about 5000 ng/ml. In some embodiments, a combination of growth factors is present in the culture medium.

Additional embodiments described herein relate to methods of expanding definitive endoderm cells in culture by obtaining a cell culture comprising definitive endoderm cells and then passaging the definitive endoderm cells so as to produce a plurality of cell cultures comprising definitive endoderm cells. In some embodiments, the definitive endoderm cells obtained in cell culture are attached to a substrate, such as the surface of a cell culture flask or the surface of a microtiter plate. In some embodiments, the definitive endoderm cells are passaged using enzymatic methods. In other embodiments, the definitive endoderm cells are mechanically passaged. In yet other embodiments, the definitive endoderm cells are passage using a cell dispersal buffer.

Still other embodiments described herein relate to expanded definitive endoderm cell cultures and/or populations produced by the methods described herein. In such embodiments, the definitive endoderm cells are multipotent cells that can differentiate into cells of the gut tube or organs derived therefrom.

In certain jurisdictions, there may not be any generally accepted definition of the term "comprising." As used herein, the term "comprising" is intended to represent "open" language which permits the inclusion of any additional elements. With this in mind, additional embodiments of the present inventions are described with reference to the numbered paragraphs below:

1. A method of expanding definitive endoderm cells in culture, said method comprising the steps of: (a) obtaining a cell culture comprising definitive endoderm cells, (b) isolating at least some of the definitive endoderm cells from at least some of the other cells in the cell culture, thereby producing a cell population enriched in definitive endoderm cells; and (c) culturing said cell population enriched in definitive endoderm cells under conditions that permit the expansion of said definitive endoderm cells.

2. The method of paragraph 1, wherein said definitive endoderm cells being multipotent cells that can differentiate into cells of the gut tube or organs derived therefrom.

3. The method of paragraph 1, wherein said definitive endoderm cells are human definitive endoderm cells.

4. The method of paragraph 3, wherein said definitive endoderm cells are derived from human embryonic stem cells (hESCs).

5. The method of paragraph 4, wherein the obtaining step comprises contacting hESCs with at least one growth factor from the TGFβ superfamily so as to permit differentiation of at least some of said hESCs to definitive endoderm cells.

6. The method of paragraph 5, wherein said at least one growth factor from the TGFβ superfamily comprises activin A.

7. The method of paragraph 1, wherein the step of obtaining said cell culture comprising definitive endoderm further comprises obtaining a portion of an existing definitive endoderm culture.

8. The method of paragraph 1, wherein said cell population enriched in definitive endoderm cells is substantially free of cells other than definitive endoderm cells.

9. The method of paragraph 1, wherein said cell population enriched in definitive endoderm cells comprises at least about 96% definitive endoderm cells.

10. The method of paragraph 1, wherein said cell population enriched in definitive endoderm cells comprises at least about 97% definitive endoderm cells.

11. The method of paragraph 1, wherein said cell population enriched in definitive endoderm cells comprises at least about 98% definitive endoderm cells.

12. The method of paragraph 1, wherein said cell population enriched in definitive endoderm cells comprises at least about 99% definitive endoderm cells.

13. The method of paragraph 1, wherein said cell population enriched in definitive endoderm cells comprises about 100% definitive endoderm cells.

14. The method of paragraph 1, wherein said isolating step comprises providing said cell culture with a reagent which binds to a marker expressed in said definitive endoderm cells but which is not substantially expressed in said other cells present in the cell culture, and separating said definitive endoderm cells bound to said reagent from said other cells present in the cell culture, thereby producing a cell population enriched in definitive endoderm cells.

15. The method of paragraph 14, wherein said marker is CXCR4.

16. The method of paragraph 14, wherein said reagent is an antibody.

17. The method of paragraph 16, wherein said antibody has affinity for CXCR4.

18. The method of paragraph 14, wherein said definitive endoderm cells bound to said reagent are separated from said other cells present in the cell culture by fluorescence activated cell sorting (FACS).

19. The method of paragraph 1, wherein said isolating step comprises separating fluorescently-labeled definitive endoderm cells from unlabeled cells.

20. The method of paragraph 19, wherein said fluorescently-labeled definitive endoderm cells are labeled as a result of the expression of enhanced green fluorescent protein (EGFP).

21. The method of paragraph 20, wherein the expression of EGFP is under control of the SOX17 promoter.

22. The method of paragraph 20, wherein the expression of EGFP is under control of the CXCR4 promoter.

23. The method of paragraph 19, wherein said fluorescently-labeled definitive endoderm cells are separated from unlabeled cells by FACS.

24. The method of paragraph 1, wherein said culturing step comprises plating said population enriched in definitive endoderm cells or a portion thereof.

25. The method of paragraph 24, wherein said population enriched in definitive endoderm cells or a portion thereof is plated on a surface coated with human fibronectin.

26. The method of paragraph 25, wherein said surface is coated with poly-ornithine.

27. The method of paragraph 1, wherein said culturing step comprises incubating said population enriched in definitive endoderm cells or a portion thereof in a medium comprising about 2% (v/v) serum.

28. The method of paragraph 1, wherein said culturing step comprises incubating said population enriched in definitive endoderm cells or a portion thereof in a medium comprising greater than about 2% (v/v) serum.

29. The method of paragraph 1, wherein said culturing step comprises incubating said population enriched in definitive endoderm cells or a portion thereof in a medium comprising less than about 2% (v/v) serum.

30. The method of paragraph 1, wherein said culturing step comprises incubating said population enriched in definitive endoderm cells or a portion thereof in a medium comprising at least one growth factor.

31. The method of paragraph 30, wherein said at least one growth factor is a growth factor from the TGFβ superfamily of growth factors.

32. The method of paragraph 31, wherein said at least one growth factor from the TGFβ superfamily of growth factors comprises activin A.

33. The method of paragraph 32, wherein said activin A is present in said medium at a concentration of about 100 ng/ml.

34. The method of paragraph 30, wherein said at least one growth factor comprises IGF1.

35. The method of paragraph 34, wherein said IGF1 is present in said medium at a concentration of about 100 ng/ml.

36. The method of paragraph 30, wherein said at least one growth factor comprises a combination of activin A and IGF1.

37. The method of paragraph 30, wherein said at least one growth factor comprises bFGF.

38. The method of paragraph 37, wherein said bFGF is present in said medium at a concentration of about 12 ng/ml.

39. The method of paragraph 30, wherein said at least one growth factor comprises EGF.

40. The method of paragraph 39, wherein said EGF is present in said medium at a concentration of about 10 ng/ml.

41. The method of paragraph 30, wherein said at least one growth factor comprises a combination of activin A, bFGF and EGF.

42. An expanded definitive endoderm cell population produced by the method of paragraph 1.

43. A method of expanding definitive endoderm cells in culture, said method comprising the steps of: (a) obtaining a cell culture comprising definitive endoderm cells, and (b) passaging said definitive endoderm cells, thereby producing a plurality of cell cultures comprising definitive endoderm cells.

44. The method of paragraph 43, wherein the step of passaging said definitive endoderm cells comprises providing at least one enzyme to said cell culture.

45. The method of paragraph 44, wherein said at least one enzyme comprises at least one protease.

46. The method of paragraph 45, wherein said at least one protease comprises trypsin.

47. The method of paragraph 43, wherein the step of passaging said definitive endoderm cells comprises mechanically disrupting contacts between said definitive endoderm cells.

48. The method of paragraph 43, wherein the step of passaging said definitive endoderm cells comprises incubating said definitive endoderm cells in a cell dispersal buffer.

49. The method of paragraph 43, wherein said definitive endoderm cells are attached to a substrate.

50. The method of paragraph 49, wherein the step of passaging said definitive endoderm cells comprises detaching said definitive endoderm cells from said substrate.

51. The method of paragraph 50, wherein said substrate is a surface of a tissue culture flask.

52. The method of paragraph 50, wherein said substrate is a surface of a microtiter plate.

53. An expanded definitive endoderm cell population produced by the method of paragraph 43.

It will be appreciated that the methods and compositions described above relate to cells cultured in vitro. However, the above-described in vitro differentiated cell compositions may be used for in vivo applications.

Additional embodiments of the present invention may also be found in U.S. Provisional Patent Application No. 60/532,004, entitled DEFINITIVE ENDODERM, filed Dec. 23, 2003; U.S. Provisional Patent Application No. 60/566,293, entitled PDX1 EXPRESSING ENDODERM, filed Apr. 27, 2004; U.S. Provisional Patent Application No. 60/586,566, entitled CHEMOKINE CELL SURFACE RECEPTOR FOR THE ISOLATION OF DEFINITIVE ENDODERM, filed Jul. 9, 2004; U.S. Provisional Patent Application No. 60/587,942, entitled CHEMOKINE CELL SURFACE RECEPTOR FOR THE ISOLATION OF DEFINITIVE ENDODERM, filed Jul. 14, 2004; U.S. patent application Ser. No. 11/021,618, entitled DEFINITIVE ENDODERM, filed Dec. 23, 2004; U.S. patent application Ser. No. 11/115,868, entitled PDX1 EXPRESSING ENDODERM, filed Apr. 26, 2005; U.S. patent application Ser. No. 11/165,305, entitled METHODS FOR IDENTIFYING FACTORS FOR DIFFERENTIATING DEFINITIVE ENDODERM, filed Jun. 23, 2005; U.S. Provisional Patent Application No. 60/693,364, entitled PREPRIMITIVE STREAK AND MESENDODERM CELLS, filed Jun. 23, 2005; U.S. Provisional Patent Application No. 60/693,317, entitled EXPANSION OF ISOLATED DEFINITIVE ENDODERM CELLS, filed Jun. 23, 2005; and U.S. Provisional Patent Application No. 60/736,598, entitled MARKERS OF DEFINITIVE ENDODERM, filed Nov. 14, 2005, the disclosures of which are incorporated herein by reference in their entireties.

DETAILED DESCRIPTION

Figure 1:
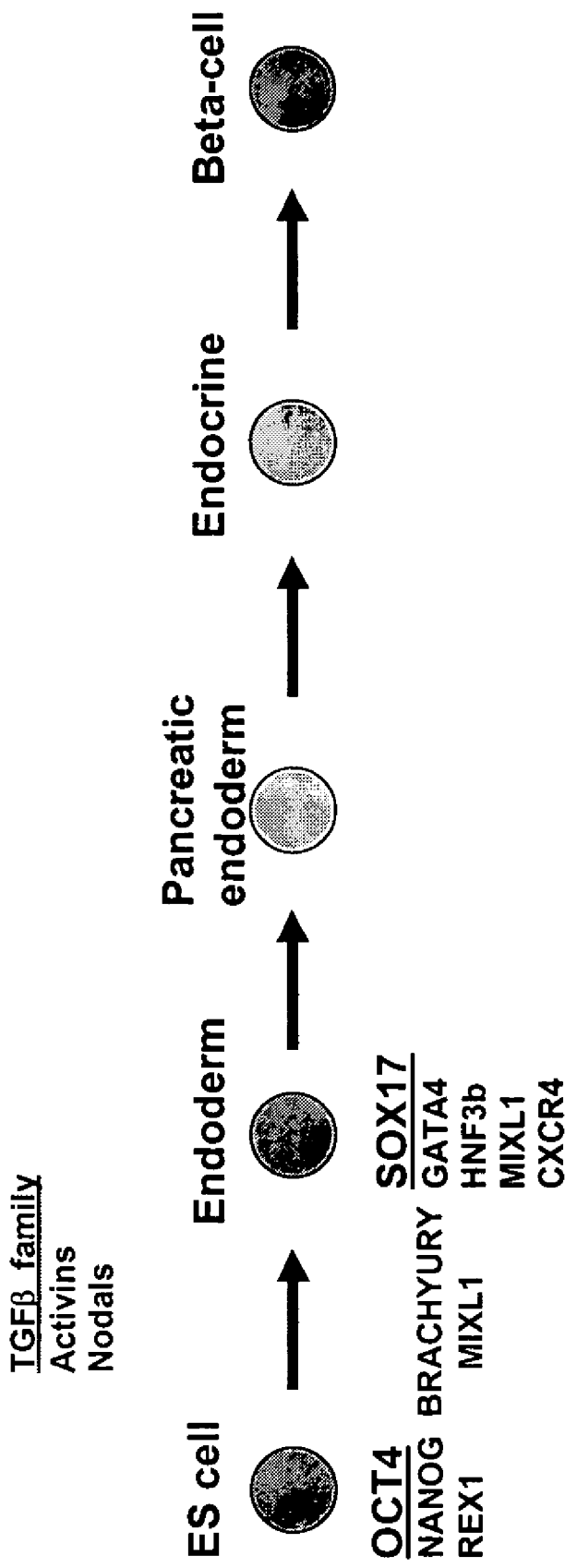
FIG. 1 is a schematic of a proposed differentiation pathway for the production of beta-cells from hESCs. The first step in the pathway commits the ES cell to the definitive endoderm lineage and represents one of the earliest known steps in the further differentiation of ES cells to pancreatic endoderm, endocrine endoderm, or islet/beta-cell. Some factors useful for mediating this transition are members of the TGFβ family which include, but are not limited to, activins and nodals. Exemplary markers for defining the definitive endoderm target cell are SOX17, GATA4, HNF3b, MIX1 and CXCR4.

A crucial stage in early human development termed gastrulation occurs 2-3 weeks after fertilization. Gastrulation is extremely significant because it is at this time that the three primary germ layers are first specified and organized (Lu et al., 2001; Schoenwolf and Smith, 2000). The ectoderm is responsible for the eventual formation of the outer coverings of the body and the entire nervous system whereas the heart, blood, bone, skeletal muscle and other connective tissues are derived from the mesoderm. Definitive endoderm is defined as the germ layer that is responsible for formation of the entire gut tube which includes the esophagus, stomach and small and large intestines, and the organs which derive from the gut tube such as the lungs, liver, thymus, parathyroid and thyroid glands, gall bladder and pancreas (Grapin-Botton and Melton, 2000; Kimelman and Griffin, 2000; Tremblay et al., 2000; Wells and Melton, 1999; Wells and Melton, 2000). A very important distinction should be made between the definitive endoderm and the completely separate lineage of cells termed primitive endoderm. The primitive endoderm is primarily responsible for formation of extra-embryonic tissues, mainly the parietal and visceral endoderm portions of the placental yolk sac and the extracellular matrix material of Reichert's membrane.

During gastrulation, the process of definitive endoderm formation begins with a cellular migration event in which mesendoderm cells (cells competent to form mesoderm or endoderm) migrate through a structure called the primitive streak. Definitive endoderm is derived from cells, which migrate through the anterior portion of the streak and through the node (a specialized structure at the anterior-most region of the streak). As migration occurs, definitive endoderm populates first the most anterior gut tube and culminates with the formation of the posterior end of the gut tube.

Definitive endoderm and endoderm cells derived therefrom represent important multipotent starting points for the derivation of cells which make up terminally differentiated tissues and/or organs derived from the definitive endoderm lineage. Such cells, tissues and/or organs are extremely useful in cell therapies. Because large numbers of cells are usually necessary for successful cell therapy applications, it is beneficial to begin differentiation procedures with large numbers of cells of a single cell type. As embryonic stem cells in culture differentiate to definitive endoderm, not every embryonic stem cell is converted to the definitive endoderm cell type. To overcome this problem, definitive endoderm cells growing in mixed cell cultures can be enriched, isolated and/or purified using the methodology described herein. After such enrichment, isolation and/or purification, the resulting definitive endoderm cells may not be easy to grow in culture. Methods described herein improve the ability of enriched, isolated and/or purified definitive endoderm cells to grow and expand in cell culture. Because definitive endoderm cells can now be expanded in culture subsequent to enrichment, isolation and/or purification, cells, tissues and/or organs derived from definitive endoderm cells can be produced in greater numbers.

Some embodiments of the present invention relate to methods of expanding definitive endoderm cells in cell culture. In some embodiments, definitive endoderm cells are enriched by separating these cells from other cells in a mixed cell culture. The enriched definitive endoderm cells are then cultured under conditions which permit their expansion.

Definitions

Certain terms and phrases as used throughout this application have the meanings provided as follows:

As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer.

As used herein, "multipotent" or "multipotent cell" refers to a cell type that can give rise to a limited number of other particular cell types.

As used herein, "expression" refers to the production of a material or substance as well as the level or amount of production of a material or substance. Thus, determining the expression of a specific marker refers to detecting either the relative or absolute amount of the marker that is expressed or simply detecting the presence or absence of the marker.

As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipd, a lipid, a lipoprotein or a small molecule (for example, molecules having a molecular weight of less than 10,000 amu)

When used in connection with cell cultures and/or cell populations, the term "portion" means any non-zero amount of the cell culture or cell population, which ranges from a single cell to the entirety of the cell culture or cells population.

With respect to cells in cell cultures or in cell populations, the phrase "substantially free of" means that the specified cell type of which the cell culture or cell population is free, is present in an amount of less than about 5% of the total number of cells present in the cell culture or cell population.

With respect to cell culture medium, as used herein, "low serum RPMI" refers to a low serum containing medium, wherein the serum concentration is gradually increased over a defined time period. For example, in one embodiment, low serum RPMI comprises a concentration of about 0.2% fetal bovine serum (FBS) on the first day of cell growth, about 0.5% FBS on the second day of cell growth and about 2% FBS on the third through fifth day of cell growth. In another embodiment, low serum RPMI comprises a concentration of about 0% on day one, about 0.2% on day two and about 2% on the third and subsequent days.

As used herein, the terms "bFGF" and "FGF2" are used interchangeably.

Definitive Endoderm Cells and Processes Related Thereto

Embodiments described herein relate to novel, defined processes for the production of definitive endoderm cells in culture by differentiating pluripotent cells, such as stem cells into multipotent definitive endoderm cells. As described above, definitive endoderm cells do not differentiate into tissues produced from ectoderm or mesoderm, but rather, differentiate into the gut tube as well as organs that are derived from the gut tube. In certain preferred embodiments, the definitive endoderm cells are derived from hESCs. Such processes can provide the basis for efficient production of human endodermal derived tissues such as pancreas, liver, lung, stomach, intestine, thyroid and thymus. For example, production of definitive endoderm may be the first step in differentiation of a stem cell to a functional insulin-producing β-cell. To obtain useful quantities of insulin-producing β-cells, high efficiency of differentiation is desirable for each of the differentiation steps that occur prior to reaching the pancreatic islet/β-cell fate. Since differentiation of stem cells to definitive endoderm cells represents perhaps the earliest step towards the production of functional pancreatic islet/β-cells (as shown in FIG. 1), high efficiency of differentiation at this step is particularly desirable.

In view of the desirability of efficient differentiation of pluripotent cells to definitive endoderm cells, some aspects of the differentiation processes described herein relate to in vitro methodology that results in approximately 50-80% conversion of pluripotent cells to definitive endoderm cells. Typically, such methods encompass the application of culture and growth factor conditions in a defined and temporally specified fashion. Further enrichment of the cell population for definitive endoderm cells can be achieved by isolation and/or purification of the definitive endoderm cells from other cells in the population by using a reagent that specifically binds to definitive endoderm cells. As such, some embodiments described herein relate to definitive endoderm cells as well as methods for producing and isolating and/or purifying such cells.

In order to determine the amount of definitive endoderm cells in a cell culture or cell population, a method of distinguishing this cell type from the other cells in the culture or in the population is desirable. Accordingly, certain embodiments described herein relate to cell markers whose presence, absence and/or relative expression levels are specific for definitive endoderm and methods for detecting and determining the expression of such markers.

In some embodiments described herein, the presence, absence and/or level of expression of a marker is determined by quantitative PCR (Q-PCR). For example, the amount of transcript produced by certain genetic markers, such as SOX17, CXCR4, OCT4, AFP, TM, SPARC, SOX7, MIXL1, GATA4, HNF3b, GSC, FGF17, VWF, CALCR, FOXQ1, CMKOR1, CRIP1 and other markers described herein is determined by quantitative Q-PCR. In other embodiments, immunohistochemistry is used to detect the proteins expressed by the above-mentioned genes. In still other embodiments, Q-PCR and immunohistochemical techniques are both used to identify and determine the amount or relative proportions of such markers.

By using methods, such as those described above, to determine the expression of one or more appropriate markers, it is possible to identify definitive endoderm cells, as well as determine the proportion of definitive endoderm cells in a cell culture or cell population. For example, in some embodiments of the present invention, the definitive endoderm cells or cell populations that are produced express the SOX17 and/or the CXCR4 gene at a level of about 2 orders of magnitude greater than non-definitive endoderm cell types or cell populations. In other embodiments, the definitive endoderm cells or cell populations that are produced express the SOX17 and/or the CXCR4 gene at a level of more than 2 orders of magnitude greater than non-definitive endoderm cell types or cell populations. In still other embodiments, the definitive endoderm cells or cell populations that are produced express one or more of the markers selected from the group consisting of SOX17, CXCR4, GSC, FGF17, VWF, CALCR, FOXQ1, CMKOR1 and CRIP1 at a level of about 2 or more than 2 orders of magnitude greater than non-definitive endoderm cell types or cell populations. In some embodiments described herein, definitive endoderm cells do not substantially express PDX1.

Embodiments described herein also relate to definitive endoderm compositions. For example, some embodiments relate to cell cultures comprising definitive endoderm, whereas others relate to cell populations enriched in definitive endoderm cells. Some preferred embodiments relate to cell cultures which comprise definitive endoderm cells, wherein at least about 50-80% of the cells in culture are definitive endoderm cells. An especially preferred embodiment relates to cells cultures comprising human cells, wherein at least about 50-80% of the human cells in culture are definitive endoderm cells. Because the efficiency of the differentiation procedure can be adjusted by modifying certain parameters, which include but are not limited to, cell growth conditions, growth factor concentrations and the timing of culture steps, the differentiation procedures described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% conversion of pluripotent cells to definitive endoderm. In other preferred embodiments, conversion of a pluripotent cell population, such as a stem cell population, to substantially pure definitive endoderm cell population is contemplated.

The compositions and methods described herein have several useful features. For example, the cell cultures and cell populations comprising definitive endoderm as well as the methods for producing such cell cultures and cell populations are useful for modeling the early stages of human development. Furthermore, the compositions and methods described herein can also serve for therapeutic intervention in disease states, such as diabetes mellitus. For example, since definitive endoderm serves as the source for only a limited number of tissues, it can be used in the development of pure tissue or cell types.

Production of Definitive Endoderm from Pluripotent Cells

Processes for differentiating pluripotent cells to produce cell cultures and enriched cell populations comprising definitive endoderm is described below and in U.S. Pat. No. 11/021,618, entitled DEFINITIVE ENDODERM, filed Dec. 23, 2004, the disclosure of which is incorporated herein by reference in its entirety. In some of these processes, the pluripotent cells used as starting material are stem cells. In certain processes, definitive endoderm cell cultures and enriched cell populations comprising definitive endoderm cells are produced from embryonic stem cells. A preferred method for deriving definitive endoderm cells utilizes human embryonic stem cells as the starting material for definitive endoderm production. Such pluripotent cells can be cells that originate from the morula, embryonic inner cell mass or those obtained from embryonic gonadal ridges. Human embryonic stem cells can be maintained in culture in a pluripotent state without substantial differentiation using methods that are known in the art. Such methods are described, for example, in U.S. Pat. Nos. 5,453,357, 5,670,372, 5,690,926 5,843,780, 6,200,806 and 6,251,671 the disclosures of which are incorporated herein by reference in their entireties.

In some processes for producing definitive endoderm cells, hESCs are maintained on a feeder layer. In such processes, any feeder layer which allows hESCs to be maintained in a pluripotent state can be used. One commonly used feeder layer for the cultivation of human embryonic stem cells is a layer of mouse fibroblasts. More recently, human fibroblast feeder layers have been developed for use in the cultivation of hESCs (see US Patent Application No. 2002/0072117, the disclosure of which is incorporated herein by reference in its entirety). Alternative processes for producing definitive endoderm permit the maintenance of pluripotent hESC without the use of a feeder layer. Methods of maintaining pluripotent hESCs under feeder-free conditions have been described in US Patent Application No. 2003/0175956, the disclosure of which is incorporated herein by reference in its entirety.

The human embryonic stem cells used herein can be maintained in culture either with or without serum. In some embryonic stem cell maintenance procedures, serum replacement is used. In others, serum free culture techniques, such as those described in US Patent Application No. 2003/0190748, the disclosure of which is incorporated herein by reference in its entirety, are used.

Stem cells are maintained in culture in a pluripotent state by routine passage until it is desired that they be differentiated into definitive endoderm. In some processes, differentiation to definitive endoderm is achieved by providing to the stem cell culture a growth factor of the TGFβ superfamily in an amount sufficient to promote differentiation to definitive endoderm. Growth factors of the TGFβ superfamily which are useful for the production of definitive endoderm are selected from the Nodal/Activin or BMP subgroups. In some preferred differentiation processes, the growth factor is selected from the group consisting of Nodal, activin A, activin B and BMP4. Additionally, the growth factor Wnt3a and other Wnt family members are useful for the production of definitive endoderm cells. In certain differentiation processes, combinations of any of the above-mentioned growth factors can be used.

With respect to some of the processes for the differentiation of pluripotent stem cells to definitive endoderm cells, the above-mentioned growth factors are provided to the cells so that the growth factors are present in the cultures at concentrations sufficient to promote differentiation of at least a portion of the stem cells to definitive endoderm cells. In some processes, the above-mentioned growth factors are present in the cell culture at a concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, at least about 1000 ng/ml, at least about 2000 ng/ml, at least about 3000 ng/ml, at least about 4000 ng/ml, at least about 5000 ng/ml or more than about 5000 ng/ml.

In certain processes for the differentiation of pluripotent stem cells to definitive endoderm cells, the above-mentioned growth factors are removed from the cell culture subsequent to their addition. For example, the growth factors can be removed within about one day, about two days, about three days, about four days, about five days, about six days, about seven days, about eight days, about nine days or about ten days after their addition. In a preferred processes, the growth factors are removed about four days after their addition.

Cultures of definitive endoderm cells can be grown in medium containing reduced serum or no serum. Under certain culture conditions, serum concentrations can range from about 0.05% v/v to about 20% v/v. For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In some processes, definitive endoderm cells are grown without serum or with serum replacement. In still other processes, definitive endoderm cells are grown in the presence of B27. In such processes, the concentration of B27 supplement can range from about 0.1% v/v to about 20% v/v.

Monitoring the Differentiation of Pluripotent Cells to Definitive Endoderm

The progression of the hESC culture to definitive endoderm can be monitored by determining the expression of markers characteristic of definitive endoderm. In some processes, the expression of certain markers is determined by detecting the presence or absence of the marker. Alternatively, the expression of certain markers can be determined by measuring the level at which the marker is present in the cells of the cell culture or cell population. In such processes, the measurement of marker expression can be qualitative or quantitative. One method of quantitating the expression of markers that are produced by marker genes is through the use of quantitative PCR (Q-PCR). Methods of performing Q-PCR are well known in the art. Other methods which are known in the art can also be used to quantitate marker gene expression. For example, the expression of a marker gene product can be detected by using antibodies specific for the marker gene product of interest. In certain processes, the expression of marker genes characteristic of definitive endoderm as well as the lack of significant expression of marker genes characteristic of hESCs and other cell types is determined.

As described further in the Examples below, a reliable marker of definitive endoderm is the SOX17 gene. As such, the definitive endoderm cells produced by the processes described herein express the SOX17 marker gene, thereby producing the SOX17 gene product. Other markers of definitive endoderm are MIXL1, GATA4, HNF3b, GSC, FGF17, VWF, CALCR, FOXQ1, CMKOR1 and CRIP1. Since definitive endoderm cells express the SOX17 marker gene at a level higher than that of the SOX7 marker gene, which is characteristic of primitive and visceral endoderm (see Table 1), in some processes, the expression of both SOX17 and SOX7 is monitored. In other processes, expression of the both the SOX17 marker gene and the OCT4 marker gene, which is characteristic of hESCs, is monitored. Additionally, because definitive endoderm cells express the SOX17 marker gene at a level higher than that of the AFP, SPARC or Thrombomodulin (TM) marker genes, the expression of these genes can also be monitored.

Another marker of definitive endoderm is the CXCR4 gene. The CXCR4 gene encodes a cell surface chemokine receptor whose ligand is the chemoattractant SDF-1. The principal roles of the CXCR4 receptor-bearing cells in the adult are believed to be the migration of hematopoetic cells to the bone marrow, lymphocyte trafficking and the differentiation of various B cell and macrophage blood cell lineages [Kim, C., and Broxmeyer, H. J. Leukocyte Biol. 65, 6-15 (1999)]. The CXCR4 receptor also functions as a coreceptor for the entry of HIV-1 into T-cells [Feng,. Y., et al. Science, 272, 872-877 (1996)]. In an extensive series of studies carried out by [McGrath, K. E. et al. Dev. Biology 213, 442-456 (1999)], the expression of the chemokine receptor CXCR4 and its unique ligand, SDF-1 [Kim, C., and Broxmyer, H., J. Leukocyte Biol. 65, 6-15 (1999)], were delineated during early development and adult life in the mouse. The CXCR4/SDF1 interaction in development became apparent when it was demonstrated that if either gene was disrupted in transgenic mice [Nagasawa et al. Nature, 382, 635-638 (1996)], Ma, Q., et al Immunity, 10, 463-471 (1999)] it resulted in late embryonic lethality. McGrath et al. demonstrated that CXCR4 is the most abundant chemokine receptor messenger RNA detected during early gastrulating embryos (E7.5) using a combination of RNase protection and in situ hybridization methodologies. In the gastrulating embryo, CXCR4/SDF-1 signaling appears to be mainly involved in inducing migration of primitive-streak germlayer cells and is expressed on definitive endoderm, mesoderm and extraembryonic mesoderm present at this time. In E7.2-7.8 mouse embryos, CXCR4 and alpha-fetoprotein are mutually exclusive indicating a lack of expression in visceral endoderm [McGrath, K. E. et al. Dev. Biology 213, 442-456 (1999)].

Since definitive endoderm cells produced by differentiating pluripotent cells express the CXCR4 marker gene, expression of CXCR4 can be monitored in order to track the production of definitive endoderm cells. Additionally, definitive endoderm cells produced by the methods described herein express other markers of definitive endoderm including, but not limited to, SOX17, MIXL1, GATA4, HNF3b, GSC, FGF17, VWF, CALCR, FOXQ1, CMKOR1 and CRIP1. Since definitive endoderm cells express the CXCR4 marker gene at a level higher than that of the SOX7 marker gene, the expression of both CXCR4 and SOX7 can be monitored. In other processes, expression of both the CXCR4 marker gene and the OCT4 marker gene, is monitored. Additionally, because definitive endoderm cells express the CXCR4 marker gene at a level higher than that of the AFP, SPARC or Thrombomodulin (TM) marker genes, the expression of these genes can also be monitored.

It will be appreciated that expression of CXCR4 in endodermal cells does not preclude the expression of SOX17. As such, definitive endoderm cells produced by the processes described herein will substantially express SOX17 and CXCR4 but will not substantially express AFP, TM, SPARC or PDX1.

It will be appreciated that SOX17 and/or CXCR4 marker expression is induced over a range of different levels in definitive endoderm cells depending on the differentiation conditions. As such, in some embodiments described herein, the expression of the SOX17 marker and/or the CXCR4 marker in definitive endoderm cells or cell populations is at least about 2-fold higher to at least about 10,000-fold higher than the expression of the SOX17 marker and/or the CXCR4 marker in non-definitive endoderm cells or cell populations, for example pluripotent stem cells. In other embodiments, the expression of the SOX17 marker and/or the CXCR4 marker in definitive endoderm cells or cell populations is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of the SOX17 marker and/or the CXCR4 marker in non-definitive endoderm cells or cell populations, for example pluripotent stem cells. In some embodiments, the expression of the SOX17 marker and/or CXCR4 marker in definitive endoderm cells or cell populations is infinitely higher than the expression of the SOX17 marker and/or the CXCR4 marker in non-definitive endoderm cells or cell populations, for example pluripotent stem cells.

It will also be appreciated that in some embodiments described herein, the expression of markers selected from the group consisting of GATA4, MIXL1, HNF3b, GSC, FGF17, VWF, CALCR, FOXQ1, CMKOR1 and CRIP1 in definitive endoderm cells or cell populations is increased as compared to the expression of GATA4, MIXL1, HNF3b, GSC, FGF17, VWF, CALCR, FOXQ1, CMKOR1 and CRIP1 in non-definitive endoderm cells or cell populations.

Additionally, it will be appreciated that there is a range of differences between the expression level of the SOX17 marker and the expression levels of the OCT4, SPARC, AFP, TM and/or SOX7 markers in definitive endoderm cells. Similarly, there exists a range of differences between the expression level of the CXCR4 marker and the expression levels of the OCT4, SPARC, AFP, TM and/or SOX7 markers in definitive endoderm cells. As such, in some embodiments described herein, the expression of the SOX17 marker or the CXCR4 marker is at least about 2-fold higher to at least about 10,000-fold higher than the expression of OCT4, SPARC, AFP, TM and/or SOX7 markers. In other embodiments, the expression of the SOX17 marker or the CXCR4 marker is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of OCT4, SPARC, AFP, TM and/or SOX7 markers. In some embodiments, OCT4, SPARC, AFP, TM and/or SOX7 markers are not significantly expressed in definitive endoderm cells.

It will also be appreciated that in some embodiments described herein, the expression of markers selected from the group consisting of GATA4, MIXL1, HNF3b, GSC, FGF17, VWF, CALCR, FOXQ1, CMKOR1 and CRIP1 in definitive endoderm cells is increased as compared to the expression of OCT4, SPARC, AFP, TM and/or SOX7 in definitive endoderm cells.

Enrichment, Isolation and/or Purification of Definitive Endoderm

Definitive endoderm cells produced by any of the above-described processes can be enriched, isolated and/or purified by using an affinity tag that is specific for such cells. Examples of affinity tags specific for definitive endoderm cells are antibodies, ligands or other binding agents that are specific to a marker molecule, such as a polypeptide, that is present on the cell surface of definitive endoderm cells but which is not substantially present on other cell types that would be found in a cell culture produced by the methods described herein. In some processes, an antibody which binds to CXCR4 is used as an affinity tag for the enrichment, isolation or purification of definitive endoderm cells. In other processes, the chemokine SDF-1 or other molecules based on SDF-1 can also be used as affinity tags. Such molecules include, but not limited to, SDF-1 fragments, SDF-1 fusions or SDF-1 mimetics.

Methods for making antibodies and using them for cell isolation are known in the art and such methods can be implemented for use with the antibodies and definitive endoderm cells described herein. In one process, an antibody which binds to CXCR4 is attached to a magnetic bead and then allowed to bind to definitive endoderm cells in a cell culture which has been enzymatically treated to reduce intercellular and substrate adhesion. The cell/antibody/bead complexes are then exposed to a movable magnetic field which is used to separate bead-bound definitive endoderm cells from unbound cells. Once the definitive endoderm cells are physically separated from other cells in culture, the antibody binding is disrupted and the cells are replated in appropriate tissue culture medium.

Additional methods for obtaining enriched, isolated or purified definitive endoderm cell cultures or populations can also be used. For example, in some embodiments, the CXCR4 antibody is incubated with a definitive endoderm-containing cell culture that has been treated to reduce intercellular and substrate adhesion. The cells are then washed, centrifuged and resuspended. The cell suspension is then incubated with a secondary antibody, such as an FITC-conjugated antibody that is capable of binding to the primary antibody. The cells are then washed, centrifuged and resuspended in buffer. The cell suspension is then analyzed and sorted using a fluorescence activated cell sorter (FACS). CXCR4-positive cells are collected separately from CXCR4-negative cells, thereby resulting in the isolation of such cell types. If desired, the isolated cell compositions can be further purified by using an alternate affinity-based method or by additional rounds of sorting using the same or different markers that are specific for definitive endoderm.

In still other processes, definitive endoderm cells are enriched, isolated and/or purified using a ligand or other molecule that binds to CXCR4. In some processes, the molecule is SDF-1 or a fragment, fusion or mimetic thereof.

In some embodiments of the processes described herein, definitive endoderm cells are fluorescently labeled then isolated from non-labeled cells by using a fluorescence activated cell sorter (FACS). In such embodiments, a nucleic acid encoding green fluorescent protein (GFP) or another nucleic acid encoding an expressible fluorescent marker gene is used to label PDX1-positive cells. For example, in some embodiments, at least one copy of a nucleic acid encoding GFP or a biologically active fragment thereof is introduced into a pluripotent cell, preferably a human embryonic stem cell, downstream of the SOX17 or CXCR4 promoter such that the expression of the GFP gene product or biologically active fragment thereof is under control of the SOX17 or CXCR4 promoter. In some embodiments, the entire coding region of the nucleic acid, which encodes SOX17 or CXCR4, is replaced by a nucleic acid encoding GFP or a biologically active fragment thereof. In other embodiments, the nucleic acid encoding GFP or a biologically active fragment thereof is fused in frame with at least a portion of the nucleic acid encoding SOX17 or CXCR4, thereby generating a fusion protein. In such embodiments, the fusion protein retains a fluorescent activity similar to GFP.

Fluorescently marked cells, such as the above-described pluripotent cells, are differentiated to definitive endoderm as described previously above. Because definitive endoderm cells express the fluorescent marker gene, whereas other cell types do not, definitive endoderm cells can be separated from the other cell types. In some embodiments, cell suspensions comprising a mixture of fluorescently-labeled definitive endoderm cells and unlabeled non-definitive endoderm cells are sorted using a FACS. Definitive endoderm cells are collected separately from non-fluorescing cells, thereby resulting in the isolation of definitive endoderm. If desired, the isolated cell compositions can be further purified by additional rounds of sorting using the same or different markers that are specific for definitive endoderm.

In preferred processes, definitive endoderm cells are enriched, isolated and/or purified from other non-definitive endoderm cells after the stem cell cultures are induced to differentiate towards the definitive endoderm lineage. It will be appreciated that the above-described enrichment, isolation and purification procedures can be used with such cultures at any stage of differentiation.

In addition to the procedures just described, definitive endoderm cells may also be isolated by other techniques for cell isolation. Additionally, definitive endoderm cells may also be enriched or isolated by methods of serial subculture in growth conditions which promote the selective survival or selective expansion of the definitive endoderm cells.

Using the methods described herein, enriched, isolated and/or purified populations of definitive endoderm cells and or tissues can be produced in vitro from pluripotent cell cultures or cell populations, such as stem cell cultures or populations, which have undergone at least some differentiation. In some methods, the cells undergo random differentiation. In a preferred method, however, the cells are directed to differentiate primarily into definitive endoderm. Some preferred enrichment, isolation and/or purification methods relate to the in vitro production of definitive endoderm from human embryonic stem cells.

Using the methods described herein, cell populations or cell cultures can be enriched in definitive endoderm content by at least about 2- to about 1000-fold as compared to untreated cell populations or cell cultures. In some embodiments, definitive endoderm cells can be enriched by at least about 5- to about 500-fold as compared to untreated cell populations or cell cultures. In other embodiments, definitive endoderm cells can be enriched from at least about 10- to about 200-fold as compared to untreated cell populations or cell cultures. In still other embodiments, definitive endoderm cells can be enriched from at least about 20- to about 100-fold as compared to untreated cell populations or cell cultures. In yet other embodiments, definitive endoderm cells can be enriched from at least about 40- to about 80-fold as compared to untreated cell populations or cell cultures. In certain embodiments, definitive endoderm cells can be enriched from at least about 2- to about 20-fold as compared to untreated cell populations or cell cultures.

Compositions Comprising Definitive Endoderm

Cell compositions produced by the above-described methods include cell cultures comprising definitive endoderm and cell populations enriched in definitive endoderm. For example, cell cultures which comprise definitive endoderm cells, wherein at least about 50-80% of the cells in culture are definitive endoderm cells, can be produced. Because the efficiency of the differentiation process can be adjusted by modifying certain parameters, which include but are not limited to, cell growth conditions, growth factor concentrations and the timing of culture steps, the differentiation procedures described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% conversion of pluripotent cells to definitive endoderm. In processes in which isolation of definitive endoderm cells is employed, for example, by using an affinity reagent that binds to the CXCR4 receptor, a substantially pure definitive endoderm cell population can be recovered.

Some embodiments described herein relate to compositions, such as cell populations and cell cultures, that comprise both pluripotent cells, such as stem cells, and definitive endoderm cells. For example, using the methods described herein, compositions comprising mixtures of hESCs and definitive endoderm cells can be produced. In some embodiments, compositions comprising at least about 5 definitive endoderm cells for about every 95 pluripotent cells are produced. In other embodiments, compositions comprising at least about 95 definitive endoderm cells for about every 5 pluripotent cells are produced. Additionally, compositions comprising other ratios of definitive endoderm cells to pluripotent cells are contemplated. For example, compositions comprising at least about 1 definitive endoderm cell for about every 1,000,000 pluripotent cells, at least about 1 definitive endoderm cell for about every 100,000 pluripotent cells, at least about 1 definitive endoderm cell for about every 10,000 pluripotent cells, at least about 1 definitive endoderm cell for about every 1000 pluripotent cells, at least about 1 definitive endoderm cell for about every 500 pluripotent cells, at least about 1 definitive endoderm cell for about every 100 pluripotent cells, at least about 1 definitive endoderm cell for about every 10 pluripotent cells, at least about 1 definitive endoderm cell for about every 5 pluripotent cells, at least about 1 definitive endoderm cell for about every 2 pluripotent cells, at least about 2 definitive endoderm cells for about every 1 pluripotent cell, at least about 5 definitive endoderm cells for about every 1 pluripotent cell, at least about 10 definitive endoderm cells for about every 1 pluripotent cell, at least about 20 definitive endoderm cells for about every 1 pluripotent cell, at least about 50 definitive endoderm cells for about every 1 pluripotent cell, at least about 100 definitive endoderm cells for about every 1 pluripotent cell, at least about 1000 definitive endoderm cells for about every 1 pluripotent cell, at least about 10,000 definitive endoderm cells for about every 1 pluripotent cell, at least about 100,000 definitive endoderm cells for about every 1 pluripotent cell and at least about 1,000,000 definitive endoderm cells for about every 1 pluripotent cell are contemplated. In some embodiments, the pluripotent cells are human pluripotent stem cells. In certain embodiments the stem cells are derived from a morula, the inner cell mass of an embryo or the gonadal ridges of an embryo. In certain other embodiments, the pluripotent cells are derived from the gondal or germ tissues of a multicellular structure that has developed past the embryonic stage.

Some embodiments described herein relate to cell cultures or cell populations comprising from at least about 5% definitive endoderm cells to at least about 95% definitive endoderm cells. In some embodiments the cell cultures or cell populations comprise mammalian cells. In preferred embodiments, the cell cultures or cell populations comprise human cells. For example, certain specific embodiments relate to cell cultures comprising human cells, wherein from at least about 5% to at least about 95% of the human cells are definitive endoderm cells. Other embodiments relate to cell cultures comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or greater than 90% of the human cells are definitive endoderm cells. In embodiments where the cell cultures or cell populations comprise human feeder cells, the above percentages are calculated without respect to the human feeder cells in the cell cultures or cell populations.

Further embodiments described herein relate to compositions, such as cell cultures or cell populations, comprising human cells, such as human definitive endoderm cells, wherein the expression of either the SOX17 or the CXCR4 marker is greater than the expression of the OCT4, SPARC, alpha-fetoprotein (AFP), Thrombomodulin (TM) and/or SOX7 marker in at least about 5% of the human cells. In other embodiments, the expression of either the SOX17 or the CXCR4 marker is greater than the expression of the OCT4, SPARC, AFP, TM and/or SOX7 marker in at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells or in greater than 95% of the human cells. In embodiments where the cell cultures or cell populations comprise human feeder cells, the above percentages are calculated without respect to the human feeder cells in the cell cultures or cell populations.

It will be appreciated that some embodiments described herein relate to compositions, such as cell cultures or cell populations, comprising human cells, such as human definitive endoderm cells, wherein the expression of one or more markers selected from the group consisting of GATA4, MIXL1, HNF3b, GSC, FGF17, VWF, CALCR, FOXQ1, CMKOR1 and CRIP1 is greater than the expression of the OCT4, SPARC, AFP, TM and/or SOX7 markers in from at least about 5% to greater than at least about 95% of the human cells. In embodiments where the cell cultures or cell populations comprise human feeder cells, the above percentages are calculated without respect to the human feeder cells in the cell cultures or cell populations.

Still other embodiments described herein relate to compositions, such as cell cultures or cell populations, comprising human cells, such as human definitive endoderm cells, wherein the expression both the SOX17 and the CXCR4 marker is greater than the expression of the OCT4, SPARC, AFP, TM and/or SOX7 marker in at least about 5% of the human cells. In other embodiments, the expression of both the SOX17 and the CXCR4 marker is greater than the expression of the OCT4, SPARC, AFP, TM and/or SOX7 marker in at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells or in greater than 95% of the human cells. In embodiments where the cell cultures or cell populations comprise human feeder cells, the above percentages are calculated without respect to the human feeder cells in the cell cultures or cell populations.

It will be appreciated that some embodiments described herein relate to compositions, such as cell cultures or cell populations, comprising human cells, such as human definitive endoderm cells, wherein the expression of the GATA4, MIXL1, HNF3b, GSC, FGF17, VWF, CALCR, FOXQ1, CMKOR1 and CRIP1 markers is greater than the expression of the OCT4, SPARC, AFP, TM and/or SOX7 markers in from at least about 5% to greater than at least about 95% of the human cells. In embodiments where the cell cultures or cell populations comprise human feeder cells, the above percentages are calculated without respect to the human feeder cells in the cell cultures or cell populations.

Additional embodiments described herein relate to compositions, such as cell cultures or cell populations, comprising mammalian endodermal cells, such as human endoderm cells, wherein the expression of either the SOX17 or the CXCR4 marker is greater than the expression of the OCT4, SPARC, AFP, TM and/or SOX7 marker in at least about 5% of the endodermal cells. In other embodiments, the expression of either the SOX17 or the CXCR4 marker is greater than the expression of the OCT4, SPARC, AFP, TM and/or SOX7 marker in at least about 10% of the endodermal cells, in at least about 15% of the endodermal cells, in at least about 20% of the endodermal cells, in at least about 25% of the endodermal cells, in at least about 30% of the endodermal cells, in at least about 35% of the endodermal cells, in at least about 40% of the endodermal cells, in at least about 45% of the endodermal cells, in at least about 50% of the endodermal cells, in at least about 55% of the endodermal cells, in at least about 60% of the endodermal cells, in at least about 65% of the endodermal cells, in at least about 70% of the endodermal cells, in at least about 75% of the endodermal cells, in at least about 80% of the endodermal cells, in at least about 85% of the endodermal cells, in at least about 90% of the endodermal cells, in at least about 95% of the endodermal cells or in greater than 95% of the endodermal cells.

It will be appreciated that some embodiments described herein relate to compositions, such as cell cultures or cell populations comprising mammalian endodermal cells, wherein the expression of one or more markers selected from the group consisting of GATA4, MIXL1, HNF3b, GSC, FGF17, VWF, CALCR, FOXQ1, CMKOR1 and CRIP1 is greater than the expression of the OCT4, SPARC, AFP, TM and/or SOX7 markers in from at least about 5% to greater than at least about 95% of the endodermal cells.

Still other embodiments described herein relate to compositions, such as cell cultures or cell populations, comprising mammalian endodermal cells, such as human endodermal cells, wherein the expression of both the SOX17 and the CXCR4 marker is greater than the expression of the OCT4, SPARC, AFP, TM and/or SOX7 marker in at least about 5% of the endodermal cells. In other embodiments, the expression of both the SOX17 and the CXCR4 marker is greater than the expression of the OCT4, SPARC, AFP, TM and/or SOX7 marker in at least about 10% of the endodermal cells, in at least about 15% of the endodermal cells, in at least about 20% of the endodermal cells, in at least about 25% of the endodermal cells, in at least about 30% of the endodermal cells, in at least about 35% of the endodermal cells, in at least about 40% of the endodermal cells, in at least about 45% of the endodermal cells, in at least about 50% of the endodermal cells, in at least about 55% of the endodermal cells, in at least about 60% of the endodermal cells, in at least about 65% of the endodermal cells, in at least about 70% of the endodermal cells, in at least about 75% of the endodermal cells, in at least about 80% of the endodermal cells, in at least about 85% of the endodermal cells, in at least about 90% of the endodermal cells, in at least about 95% of the endodermal cells or in greater than 95% of the endodermal cells.

It will be appreciated that some embodiments described herein relate to compositions, such as cell cultures or cell populations comprising mammalian endodermal cells, wherein the expression of the GATA4, MIXL1, HNF3b, GSC, FGF17, VWF, CALCR, FOXQ1, CMKOR1 and CRIP1 markers is greater than the expression of the OCT4, SPARC, AFP, TM and/or SOX7 markers in from at least about 5% to greater than at least about 95% of the endodermal cells.

Using the methods described herein, compositions comprising definitive endoderm cells substantially free of other cell types can be produced. In some embodiments described herein, the definitive endoderm cell populations or cell cultures produced by the methods described herein are substantially free of cells that significantly express the OCT4, SOX7, AFP, SPARC, TM, ZIC1 or BRACH marker genes.

In one embodiment, a description of a definitive endoderm cell based on the expression of marker genes is, SOX17 high, MIXL1 high, AFP low, SPARC low, Thrombomodulin low, SOX7 low, CXCR4 high.

Expansion of Definitive Endoderm Cells

According to some of the in vitro methods described herein, definitive endoderm cells are maintained, grown, passaged and/or expanded while in cell culture. In some embodiments the definitive endoderm cells are maintained, grown, passaged and/or expanded without any significant differentiation. In other words, in such embodiments, the definitive endoderm cells maintain the definitive endoderm phenotype while being maintained, grown, passaged and/or expanded in cell culture.

In some embodiments, definitive endoderm cells used in the expansion methods described herein, are multipotent cells that can differentiate into cells of the gut tube or organs derived therefrom. Such cells include, but are not limited to, cells of the pancreas, liver, lungs, stomach, intestine, thyroid, thymus, pharynx, gallbladder and urinary bladder as well as precursors of such cells. Additionally, these cells can further develop into higher order structures such as tissues and/or organs. In some embodiments, the definitive endoderm cells are human definitive endoderm cells.

Some embodiments of the methods described herein comprise a step of obtaining a cell culture comprising definitive endoderm cells. The cell culture can be a pure culture of definitive endoderm cells or a mixed cell culture that comprises definitive endoderm cells as well as cells of other types. For example, the cell culture can be a culture comprising both definitive endoderm cells and human embryonic stem cells (hESCs). In some embodiments, the definitive endoderm cell culture is obtained by differentiating in vitro cell cultures of hESCs. In certain embodiments, the hESCs are derived from a morula, the inner cell mass of an embryo or the gonadal ridges of an embryo. In certain other embodiments, the pluripotent cells are derived from the gonadal or germ tissues of a multicellular structure that has developed past the embryonic stage.

Methods of differentiating hESCs so as to produce cell cultures comprising human definitive endoderm cells have been described throughout this application and in U.S. patent application Ser. No. 11/021,618, entitled DEFINITIVE ENDODERM, filed Dec. 23, 2004, the disclosure of which is incorporated herein by reference in its entirety. However, it will be appreciated that any known methods for producing human definitive endoderm cells from hESCs or from other human cell types can be used. In some embodiments described herein, the cultures of definitive endoderm cells produced by differentiating hESCs can be mixed definitive endoderm cultures, which comprise definitive endoderm cells and one or more types of other cells, enriched definitive endoderm cell cultures and/or purified definitive endoderm cell cultures. Some methods for obtaining definitive endoderm cells from hESCs comprise contacting or otherwise providing the hESCs with at least one growth factor from the TGFβ superfamily. Such growth factors can include, but are not limited to, Nodal, activin A and activin B. In some embodiments, the growth factor is provided to the hESCs at a concentration ranging from 5 ng/ml to 5000 ng/ml. In certain embodiments the growth factor is provided to the hESCs in culture at a concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, at least about 1000 ng/ml, at least about 2000 ng/ml, at least about 3000 ng/ml, at least about 4000 ng/ml, at least about 5000 ng/ml or more than about 5000 ng/ml.

In other embodiments of the methods described herein, definitive endoderm cells can be obtained from a pre-existing culture of definitive endoderm cells. In such embodiments, either a portion of or the entire culture may be used in the definitive endoderm expansion methods described herein.

In addition to obtaining cell cultures comprising definitive endoderm cells, some embodiments of the expansion methods described herein also comprise the step of isolating at least some of the definitive endoderm cells from the cell culture. In such embodiments, at least some of the definitive endoderm cells are separated from at least some of the other cells in the cell culture, thereby producing a cell population enriched in definitive endoderm cells. In some embodiments, at least some of the definitive endoderm cell are removed from the cell culture while at least some of the other cells remain in the cell culture. Other cells that are present in the cell culture can include, but are not limited to, hESCs, primitive endoderm, trophectoderm, mesoderm and ectoderm.

In other embodiments described herein, the isolating step comprises providing the cells in the cell culture with a reagent which binds to a marker expressed in said definitive endoderm cells but which is not substantially expressed in said other cells present in the cell culture. As described previously herein, in some embodiments, the marker can be any cell surface marker that is specific to definitive endoderm cells. One such marker that is described throughout this application (see especially the Examples below) is the CXCR4 marker. As described previously herein, the reagent-bound definitive endoderm cells can be separated from the non-reagent-bound cells by numerous methods. For example, an antibody against the CXCR4 receptor that is selectively present on the surface of definitive endoderm cells, can be provided to definitive endoderm cells in a cell culture. Antibody-bound definitive endoderm cells can then be separated from other cells in the culture by, for example, fluorescent activated cell sorting (FACS), binding the antibody to a solid support or isolating appropriately tagged antibody in a magnetic field. In some embodiments, the antibody is released from the definitive endoderm cells after the separation process.

As an alternative means of separation, at least some of the definitive endoderm cells are separated from at least some of the other cells in the culture by specifically fluorescently labeling the definitive endoderm cells in culture and then separating the labeled cells from the unlabeled cells by FACS. As described previously above and in the Examples, in such embodiments, hESCs are transfected with a vector comprising a fluorescent reporter gene under the control of the promoter of a marker gene that is highly expressed in definitive endoderm cells but not significantly expressed in other cell types. In some embodiments, the fluorescent reporter gene is the gene encoding green fluorescent protein (GFP) or enhanced green fluorescent protein (EGFP). In some embodiments, the GFP and/or EGFP is expressed under the control of the SOX17 or the CXCR4 promoter. Transfected hESCs are then grown in culture in the presence of a differentiation factor that specifically induces the production of definitive endoderm. In preferred embodiments, the differentiation factor is activin A. In other preferred embodiments, activin A is added to the cell culture at a concentration of 100 ng/ml.

In some embodiments described herein, the enriched definitive endoderm cell populations that are produced as a result of the isolating step are substantially free of cells other than definitive endoderm cells. In other embodiments, the enriched definitive endoderm cell populations comprise from at least about 96% to at least about 100% definitive endoderm cells. In still other embodiments, the enriched definitive endoderm cell populations comprise from at least about 96%, at least about 97%, at least about 98%, at least about 99% and at least about 100% definitive endoderm cells.

According to further embodiments of the expansion methods described herein a cell culture step is contemplated. For example, some embodiments include a culturing step that comprises plating the population enriched in definitive endoderm cells or a portion of the population. In some embodiments, the cells are plated on a surface coated with human fibronectin. In other embodiments the plates are coated with poly-ornithine. In still other embodiments, the plates are coated with poly-ornithine and human fibronectin. In preferred embodiments, the plates are IVF plates coated with both poly-ornithine and human fibronectin. It will be appreciated that although human fibronectin is a preferred coating for the plates described herein, fibronectin from other sources is sufficient for coating plates.

In other embodiments, the culturing step comprises incubating the enriched definitive endoderm cell population or portion thereof in an expansion medium comprising about 2% (v/v) serum. In some embodiments, the serum concentration can range from about 0% (v/v) to about 20% (v/v). For example, in some methods described herein, the serum concentration of the medium can be about 0.05% (v/v), about 0.1% (v/v), about 0.2% (v/v), about 0.3% (v/v), about 0.4% (v/v), about 0.5% (v/v), about 0.6% (v/v), about 0.7% (v/v), about 0.8% (v/v), about 0.9% (v/v), about 1% (v/v), about 2% (v/v), about 3% (v/v), about 4% (v/v), about 5% (v/v), about 6% (v/v), about 7% (v/v), about 8% (v/v), about 9% (v/v), about 10% (v/v), about 15% (v/v) or about 20% (v/v). In some embodiments, serum replacement is included in the medium.

In still other embodiments of the expansion methods described herein, the expansion medium also comprises at least one growth factor. In certain embodiments, the at least one growth factor is a growth factor comprises a member of the TGFβ superfamily. In such embodiments, the at least one growth factor of the TGFβ superfamily includes, but is not limited to Nodal, activin A, activin B and combinations of these growth factors. Alternatively, in some embodiments, the at least one growth factor can be IGF1 or a combination of IGF and a growth factor of the TGFβ superfamily. In other embodiments, the at least one growth factor can be bFGF, EGF or another growth factor. In yet other embodiments, the at least one growth factor can be a combination of bFGF, EGF and a growth factor of the TGFβ superfamily. In each of the above embodiments, one or more of the growth factors can be present at a concentration ranging from about 1 ng/ml to about 5000 ng/ml. In such embodiments, the concentration of growth factor in the medium is at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, at least about 1000 ng/ml, at least about 2000 ng/ml, at least about 3000 ng/ml, at least about 4000 ng/ml, at least about 5000 ng/ml or more than about 5000 ng/ml. In certain embodiments, a combination of growth factors is present in the culture medium. In such embodiments, each growth factor is present in the medium at a concentration of at a concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, at least about 1000 ng/ml, at least about 2000 ng/ml, at least about 3000 ng/ml, at least about 4000 ng/ml, at least about 5000 ng/ml or more than about 5000 ng/ml.

In addition to the above-described expansion methods, in some embodiments definitive endoderm cells are expanded by first obtaining a cell culture comprising definitive endoderm cells and then passaging the definitive endoderm cells so as to produce a plurality of cell cultures comprising definitive endoderm cells. These methods of expanding definitive endoderm cells by passaging the cells can be performed using any definitive endoderm culture regardless of how such culture is obtained. For example, these methods can be performed as part of the culturing step that follows the cell isolation step in the above-described expansion methods, or alternatively, this methods can be performed using definitive endoderm cells that have been freshly differentiated from hESCs.

In accordance with certain aspects of the expansion methods described herein, the step of passaging definitive endoderm cells comprises providing at least one enzyme to a cell culture comprising definitive endoderm cells. For example, the at least one enzyme can be one or more enzymes selected from the group consisting of papain, pronase, type I collagenase, type II collagenase, type III collagenase, type IV collagenase, trypsin, hyaluronidase, elastase, DNase I, and dispase. In some embodiments, the at least one enzyme comprises at least one protease. In preferred embodiments, the at least one protease comprises trypsin. For example, in certain embodiments, definitive endoderm cells growing in a culture vessel are passaged with trypsin by first removing the culture medium from the cells. Next, a sterile trypsin solution is provided to the definitive endoderm cells for several minutes at room temperature. The trypsin solution is then gently removed so as not to disturb the cells. After the trypsin solution has been removed, the definitive endoderm cells are provided with a culture medium, such as RPMI with 2% (v/v) serum, and the cell culture vessel is then agitated so as to disrupt cell adhesions and generate a cell suspension. In some embodiments, the cell culture medium comprises trypsin inhibitor to inactivate residual trypsin.

It will be appreciated that trypsin can be provided in a variety of sterile solutions, for example, trypsin can be provided to the definitive endoderm cells in a balanced salt solution, such as Hanks balanced salt solution. Alternatively, trypsin can be provided to the definitive endoderm in a medium with or without serum, for example in low serum RPMI.

In accordance with other aspects of the expansion methods described herein, the step of passaging definitive endoderm cells comprises mechanically disrupting contacts between said definitive endoderm cells. Such mechanical disruption techniques should be sufficient to substantially disrupt cell contacts and the substrate, however, these techniques should not be so harsh as to affect cell viability. Mechanical cell disruption techniques, such as trituration, are known to those of ordinary skill in the art.

In accordance with yet other aspects of the expansion methods described herein, the step of passaging definitive endoderm cells comprises incubating said definitive endoderm cells in a cell dispersal buffer. The cell dispersal buffer can be any dispersal buffer known in the art, for example, commercially available chemical dissociation buffers.

In some embodiments of the expansion methods described herein, the definitive endoderm cells are grown in a cell culture vessel. Cell culture vessels can include, but are not limited to, tissue culture flasks and cell culture plate, such as microtiter plates. In some embodiments, the definitive endoderm cells in culture are attached to a substrate. In certain embodiments, the step of passaging said definitive endoderm cells comprises detaching said definitive endoderm cells from the substrate. In preferred embodiments, the substrate is a surface of a tissue culture flask. In other preferred embodiments, the substrate is a surface of a microtiter plate.

EXAMPLES

Many of the examples below describe the use of pluripotent human cells. Methods of producing pluripotent human cells are well known in the art and have been described numerous scientific publications, including U.S. Pat. Nos. 5,453,357, 5,670,372, 5,690,926, 6,090,622, 6,200,806 and 6,251,671 as well as U.S. Patent Application Publication No. 2004/0229350, the disclosures of which are incorporated herein by reference in their entireties.

Example 1

Human ES Cells

For our studies of endoderm development we employed human embryonic stem cells, which are pluripotent and can divide seemingly indefinitely in culture while maintaining a normal karyotype. ES cells were derived from the 5-day-old embryo inner cell mass using either immunological or mechanical methods for isolation. In particular, the human embryonic stem cell line hESCyt-25 was derived from a supernumerary frozen embryo from an in vitro fertilization cycle following informed consent by the patient. Upon thawing the hatched blastocyst was plated on mouse embryonic fibroblasts (MEF), in ES medium (DMEM, 20% FBS, non essential amino acids, beta-mercaptoethanol, and FGF2). The embryo adhered to the culture dish and after approximately two weeks, regions of undifferentiated hESCs were transferred to new dishes with MEFs. Transfer was accomplished with mechanical cutting and a brief digestion with dispase, followed by mechanical removal of the cell clusters, washing and re-plating. Since derivation, hESCyt-25 has been serially passaged over 100 times. We employed the hESCyt-25 human embryonic stem cell line as our starting material for the production of definitive endoderm.

It will be appreciated by those of skill in the art that stem cells or other pluripotent cells can also be used as starting material for the differentiation procedures described herein. For example, cells obtained from embryonic gonadal ridges, which can be isolated by methods known in the art, can be used as pluripotent cellular starting material.

Example 2 hESCyt-25 Characterization

The human embryonic stem cell line, hESCyt-25 has maintained a normal morphology, karyotype, growth and self-renewal properties over 18 months in culture. This cell line displays strong immunoreactivity for the OCT4, SSEA-4 and TRA-1-60 antigens, all of which, are characteristic of undifferentiated hESCs and displays alkaline phosphatase activity as well as a morphology identical to other established hESC lines. Furthermore, the human stem cell line, hESCyt-25, also readily forms embryoid bodies (EBs) when cultured in suspension. As a demonstration of its pluripotent nature, hESCyT-25 differentiates into various cell types that represent the three principal germ layers. Ectoderm production was demonstrated by Q-PCR for ZIC1 as well as immunocytochemistry (ICC) for nestin and more mature neuronal markers. Immunocytochemical staining for β-III tubulin was observed in clusters of elongated cells, characteristic of early neurons. Previously, we treated EBs in suspension with retinoic acid, to induce differentiation of pluripotent stem cells to visceral endoderm (VE), an extra-embryonic lineage. Treated cells expressed high levels of α-fetoprotein (AFP) and SOX7, two markers of VE, by 54 hours of treatment. Cells differentiated in monolayer expressed AFP in sporadic patches as demonstrated by immunocytochemical staining. As will be described below, the hESCyT-25 cell line was also capable of forming definitive endoderm, as validated by real-time quantitative polymerase chain reaction (Q-PCR) and immunocytochemistry for SOX17, in the absence of AFP expression. To demonstrate differentiation to mesoderm, differentiating EBs were analyzed for Brachyury gene expression at several time points. Brachyury expression increased progressively over the course of the experiment. In view of the foregoing, the hESCyT-25 line is pluripotent as shown by the ability to form cells representing the three germ layers.

Example 3

Production of SOX17 Antibody

A primary obstacle to the identification of definitive endoderm in hESC cultures is the lack of appropriate tools. We therefore undertook the production of an antibody raised against human SOX17 protein.

The marker SOX17 is expressed throughout the definitive endoderm as it forms during gastrulation and its expression is maintained in the gut tube (although levels of expression vary along the A-P axis) until around the onset of organogenesis. SOX17 is also expressed in a subset of extra-embryonic endoderm cells. No expression of this protein has been observed in mesoderm or ectoderm. It has now been discovered that SOX17 is an appropriate marker for the definitive endoderm lineage when used in conjunction with markers to exclude extra-embryonic lineages.

As described in detail herein, the SOX17 antibody was utilized to specifically examine effects of various treatments and differentiation procedures aimed at the production of SOX17 positive definitive endoderm cells. Other antibodies reactive to AFP, SPARC and Thrombomodulin were also employed to rule out the production of visceral and parietal endoderm (extra-embryonic endoderm).

Figure 2:
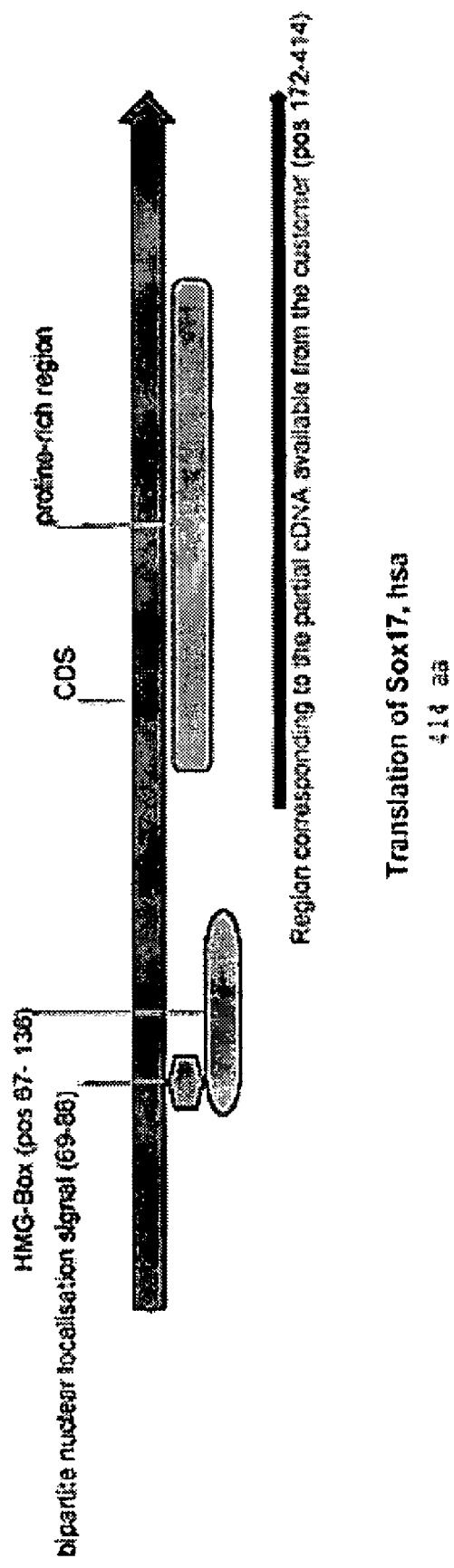
FIG. 2 is a diagram of the human SOX17 cDNA which displays the positions of conserved motifs and highlights the region used for the immunization procedure by GENOVAC.

In order to produce an antibody against SOX17, a portion of the human SOX17 cDNA (SEQ ID NO: 1) corresponding to amino acids 172-414 (SEQ ID NO: 2) in the carboxyterminal end of the SOX17 protein (FIG. 2) was used for genetic immunization in rats at the antibody production company, GENOVAC (Freiberg, Germany), according to procedures developed there. Procedures for genetic immunization can be found in U.S. Pat. Nos. 5,830,876, 5,817,637, 6,165,993 and 6,261,281 as well as International Patent Application Publication Nos. WO00/29442 and WO99/13915, the disclosures of which are incorporated herein by reference in their entireties.

Other suitable methods for genetic immunization are also described in the non-patent literature. For example, Barry et al. describe the production of monoclonal antibodies by genetic immunization in *Biotechniques* 16: 616-620, 1994, the disclosure of which is incorporated herein by reference in its entirety. Specific examples of genetic immunization methods to produce antibodies against specific proteins can be found, for example, in Costaglia et al., (1998) Genetic immunization against the human thyrotropin receptor causes thyroiditis and allows production of monoclonal antibodies recognizing the native receptor, *J. Immunol.* 160: 1458-1465; Kilpatrick et al (1998) Gene gun delivered DNA-based immunizations mediate rapid production of murine monoclonal antibodies to the Flt-3 receptor, *Hybridoma* 17: 569-576; Schmolke et al., (1998) Identification of hepatitis G virus particles in human serum by E2-specific monoclonal antibodies generated by DNA immunization, *J. Virol.* 72: 4541-4545; Krasemann et al., (1999) Generation of monoclonal antibodies against proteins with an unconventional nucleic acid-based immunization strategy, *J. Biotechnol.* 73: 119-129; and Ulivieri et al., (1996) Generation of a monoclonal antibody to a defined portion of the *Heliobacter pylori* vacuolating cytotoxin by DNA immunization, *J. Biotechnol.* 51: 191-194, the disclosures of which are incorporated herein by reference in their entireties.

Figure 3:
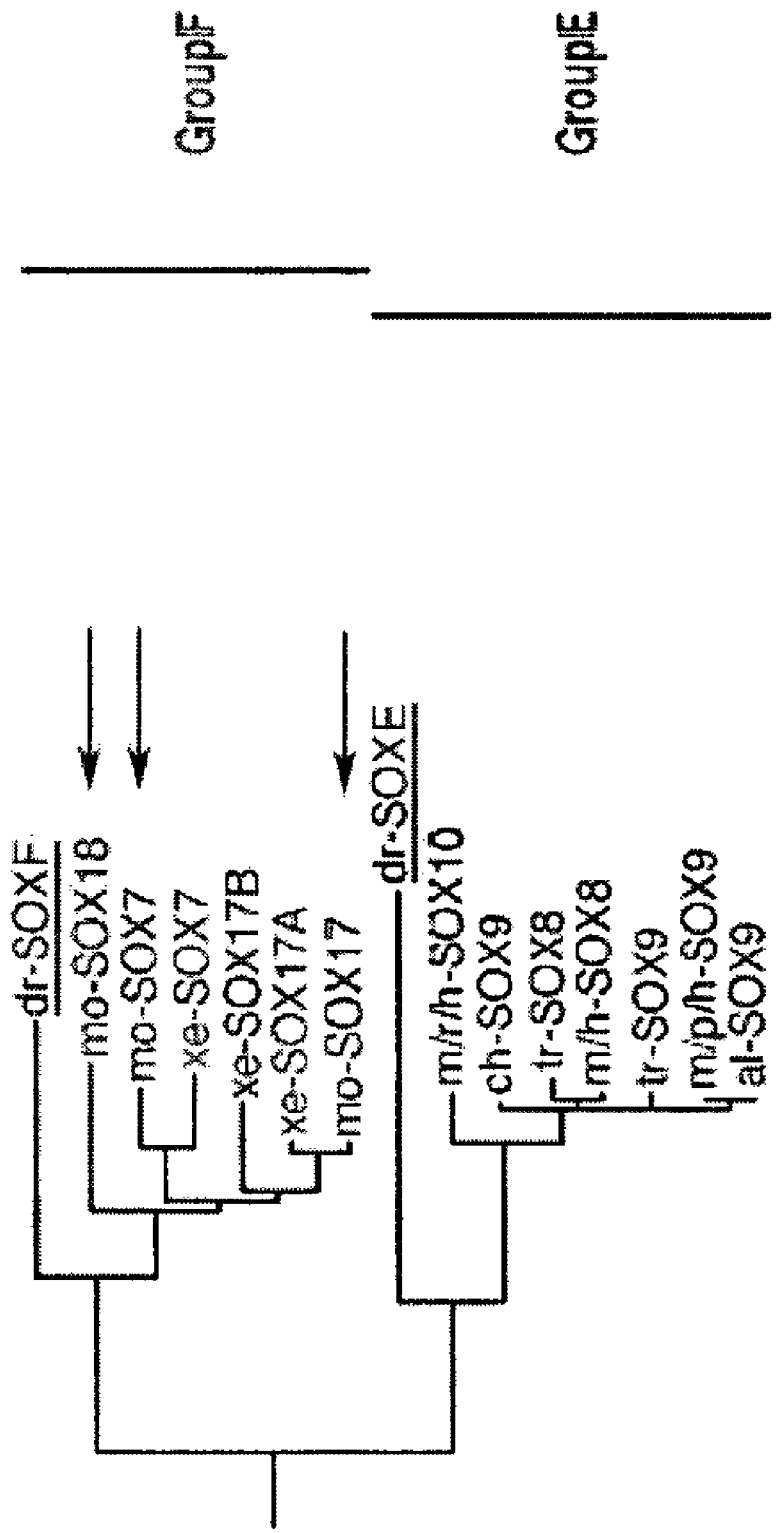
FIG. 3 is a relational dendrogram illustrating that SOX17 is most closely related to SOX7 and somewhat less to SOX18. The SOX17 proteins are more closely related among species homologs than to other members of the SOX group F subfamily within the same species.

SOX7 and SOX18 are the closest Sox family relatives to SOX17 as depicted in the relational dendrogram shown in FIG. 3. We employed the human SOX7 polypeptide as a negative control to demonstrate that the SOX17 antibody produced by genetic immunization is specific for SOX17 and does not react with its closest family member. In particular, SOX7 and other proteins were expressed in human fibroblasts, and then, analyzed for cross reactivity with the SOX17 antibody by Western blot and ICC. For example, the following methods were utilized for the production of the SOX17, SOX7 and EGFP expression vectors, their transfection into human fibroblasts and analysis by Western blot. Expression vectors employed for the production of SOX17, SOX7, and EGFP were pCMV6 (OriGene Technologies, Inc., Rockville, Md.), pCMV-SPORT6 (Invitrogen, Carlsbad, Calif.) and pEGFP-N1 (Clonetech, Palo Alto, Calif.), respectively. For protein production, telomerase immortalized MDX human fibroblasts were transiently transfected with supercoiled DNA in the presence of Lipofectamine 2000 (Invitrogen, Carlsbad, Calif.). Total cellular lysates were collected 36 hours post-transfection in 50 mM TRIS-HCl (pH 8), 150 mM NaCl, 0.1% SDS, 0.5% deoxycholate, containing a cocktail of protease inhibitors (Roche Diagnostics Corporation, Indianapolis, Ind.). Western blot analysis of 100 μg of cellular proteins, separated by SDS-PAGE on NuPAGE (4-12% gradient polyacrylamide, Invitrogen, Carlsbad, Calif.), and transferred by electro-blotting onto PDVF membranes (Hercules, Calif.), were probed with a 1/1000 dilution of the rat SOX17 anti-serum in 10 mM TRIS-HCl (pH 8), 150 mM NaCl, 10% BSA, 0.05% Tween-20 (Sigma, St. Louis, Mo.), followed by Alkaline Phosphatase conjugated anti-rat IgG (Jackson ImmunoResearch Laboratories, West Grove, Pa.), and revealed through Vector Black Alkaline Phosphatase staining (Vector Laboratories, Burlingame, Calif.). The proteins size standard used was wide range color markers (Sigma, St. Louis, Mo.).

Figure 4:
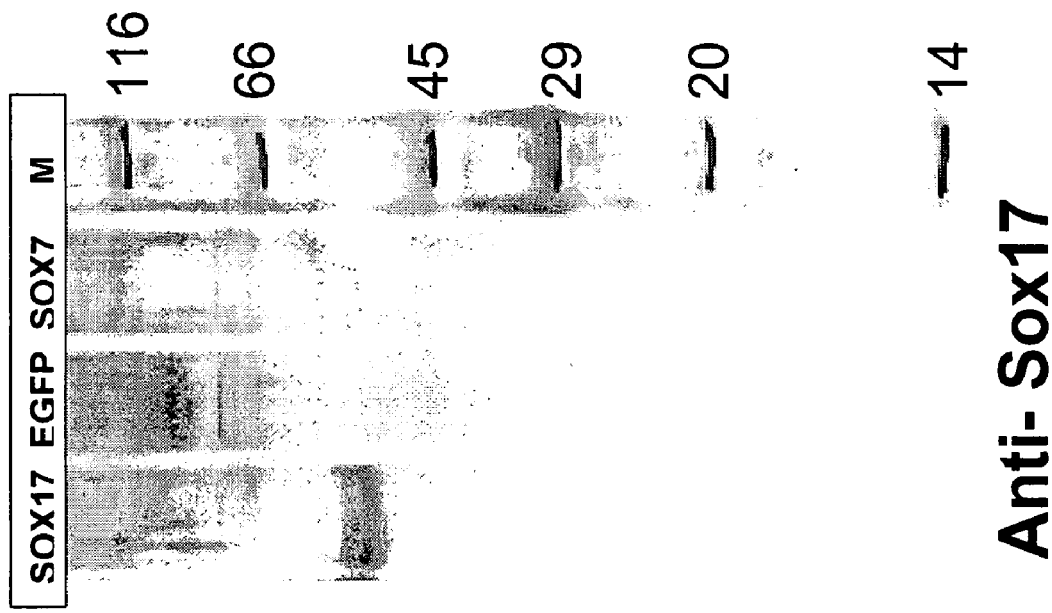
FIG. 4 is a Western blot probed with the rat anti-SOX17 antibody. This blot demonstrates the specificity of this antibody for human SOX17 protein over-expressed in fibroblasts (lane 1) and a lack of immunoreactivity with EGFP (lane 2) or the most closely related SOX family member, SOX7 (lane 3).

In FIG. 4, protein extracts made from human fibroblast cells that were transiently transfected with SOX17, SOX7 or EGFP cDNA's were probed on Western blots with the SOX17 antibody. Only the protein extract from hSOX17 transfected cells produced a band of ~51 Kda which closely matched the predicted 46 Kda molecular weight of the human SOX17 protein. There was no reactivity of the SOX17 antibody to extracts made from either human SOX7 or EGFP transfected cells. Furthermore, the SOX17 antibody clearly labeled the nuclei of human fibroblast cells transfected with the hSOX17 expression construct but did not label cells transfected with EGFP alone. As such, the SOX17 antibody exhibits specificity by ICC.

Example 4

Validation of SOX17 Antibody as a Marker of Definitive Endoderm

Figure 5:
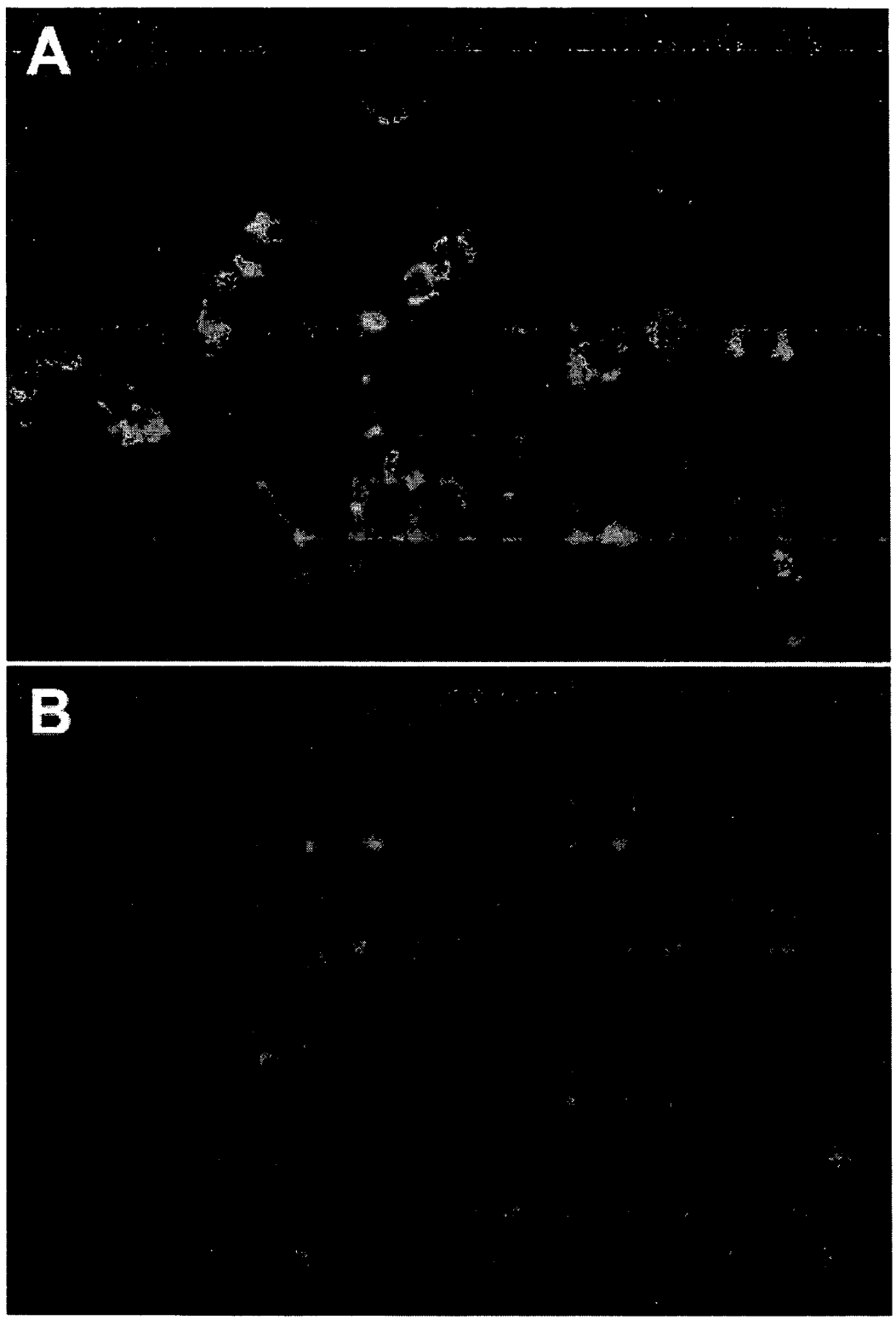
FIGS. 5A-B are micrographs showing a cluster of SOX17$^+$ cells that display a significant number of AFP$^+$ co-labeled cells (A). This is in striking contrast to other SOX17$^+$ clusters (B) where little or no AFP$^+$ cells are observed.
Figure 6:
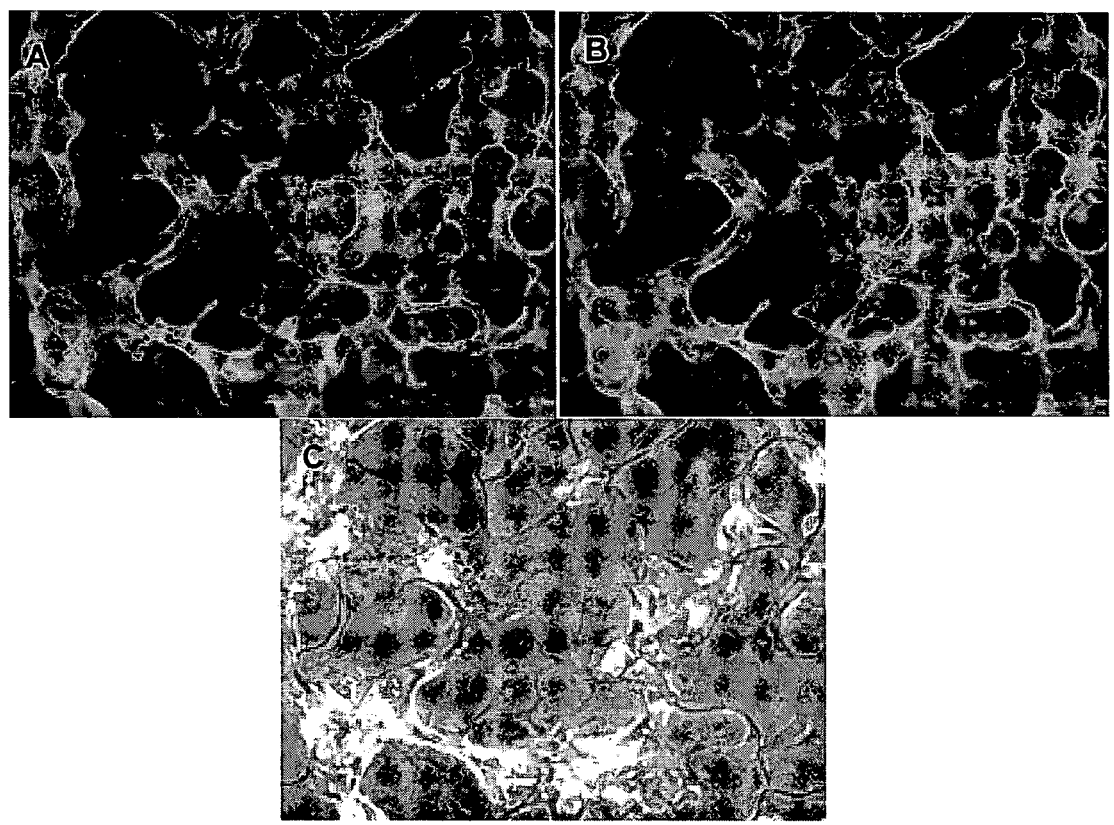
FIGS. 6A-C are micrographs showing parietal endoderm and SOX17. Panel A shows immunocytochemistry for human Thrombomodulin (TM) protein located on the cell surface of parietal endoderm cells in randomly differentiated cultures of hES cells. Panel B is the identical field shown in A double-labeled for TM and SOX17. Panel C is the phase contrast image of the same field with DAPI labeled nuclei. Note the complete correlation of DAPI labeled nuclei and SOX17 labeling.

Partially differentiated hESCs were co-labeled with SOX17 and AFP antibodies to demonstrate that the SOX17 antibody is specific for human SOX17 protein and furthermore marks definitive endoderm. It has been demonstrated that SOX17, SOX7 (which is a closely related member of the SOX gene family subgroup F (FIG. 3)) and AFP are each expressed in visceral endoderm. However, AFP and SOX7 are not expressed in definitive endoderm cells at levels detectable by ICC, and thus, they can be employed as negative markers for bonifide definitive endoderm cells. It was shown that SOX17 antibody labels populations of cells that exist as discrete groupings of cells or are intermingled with AFP positive cells. In particular, FIG. 5A shows that small numbers of SOX17 cells were co-labeled with AFP; however, regions were also found where there were little or no AFP$^+$ cells in the field of SOX17$^+$ cells (FIG. 5B). Similarly, since parietal endoderm has been reported to express SOX17, antibody co-labeling with SOX17 together with the parietal markers SPARC and/or Thrombomodulin (TM) can be used to identify the SOX17$^+$ cells that are parietal endoderm. As shown in FIGS. 6A-C, Thrombomodulin and SOX17 co-labeled parietal endoderm cells were produced by random differentiation of hES cells.

In view of the above cell labeling experiments, the identity of a definitive endoderm cell can be established by the marker profile SOX17$^{hi}$/AFP$^{lo}$/[TM$^{lo}$ or SPARC$^{lo}$]. In other words, the expression of the SOX17 marker is greater than the expression of the AFP marker, which is characteristic of visceral endoderm, and the TM or SPARC markers, which are characteristic of parietal endoderm. Accordingly, those cells positive for SOX17 but negative for AFP and negative for TM or SPARC are definitive endoderm.

Figure 7:
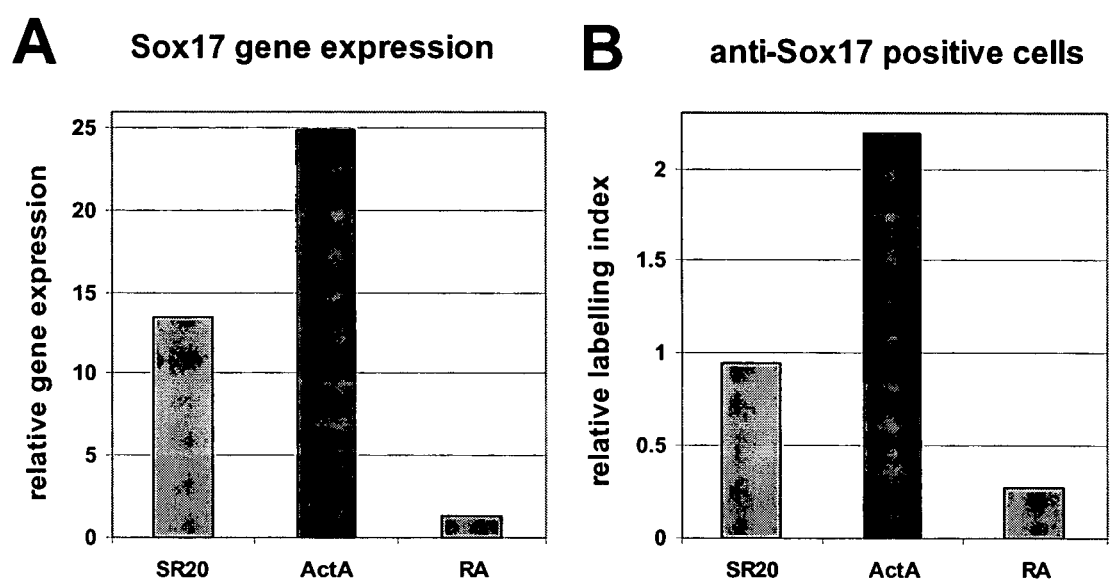
FIGS. 7A-B are bar charts showing SOX17 gene expression by quantitative PCR (Q-PCR) and anti-SOX17 positive cells by SOX17-specific antibody. Panel A shows that activin A increases SOX17 gene expression while retinoic acid (RA) strongly suppresses SOX17 expression relative to the undifferentiated control media (SR20). Panel B shows the identical pattern as well as a similar magnitude of these changes is reflected in SOX17$^+$ cell number, indicating that Q-PCR measurement of SOX17 gene expression is very reflective of changes at the single cell level.
Figure 8:
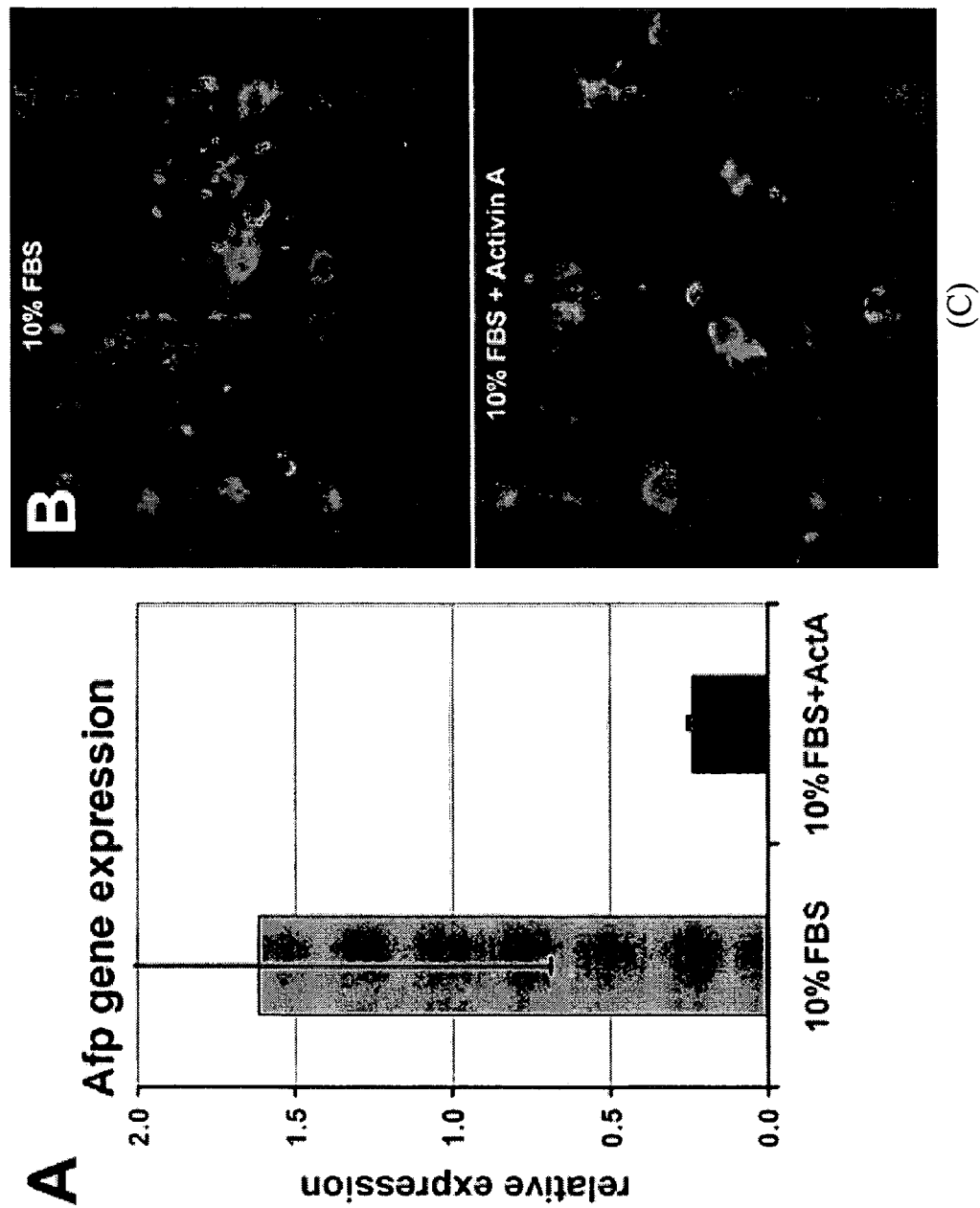
FIG. 8A is a bar chart which shows that a culture of differentiating hESCs in the presence of activin A maintains a low level of AFP gene expression while cells allowed to randomly differentiate in 10% fetal bovine serum (FBS) exhibit a strong upregulation of AFP. The difference in expression levels is approximately 7-fold.
FIGS. 8B-C are images of two micrographs showing that the suppression of AFP expression by activin A is also evident at the single cell level as indicated by the very rare and small clusters of AFP$^+$ cells observed in activin A treatment conditions (bottom) relative to 10% FBS alone (top).
Figure 9:
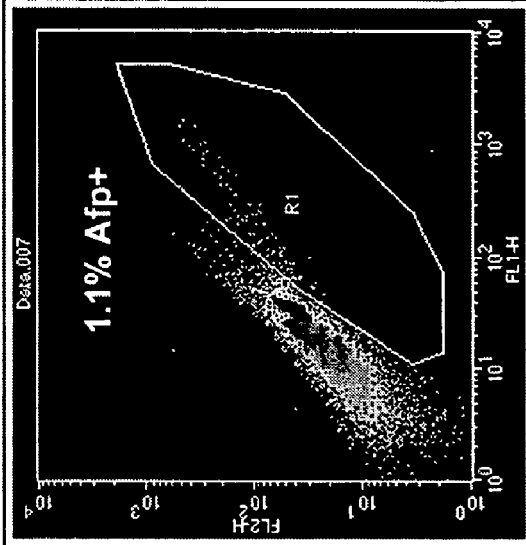
FIGS. 9A-B are comparative images showing the quantitation of the AFP$^+$ cell number using flow cytometry. This figure demonstrates that the magnitude of change in AFP gene expression (FIG. 8A) in the presence (right panel) and absence (left panel) of activin A exactly corresponds to the number of AFP$^+$ cells, further supporting the utility of Q-PCR analyses to indicate changes occurring at the individual cell level.
Figure 9:
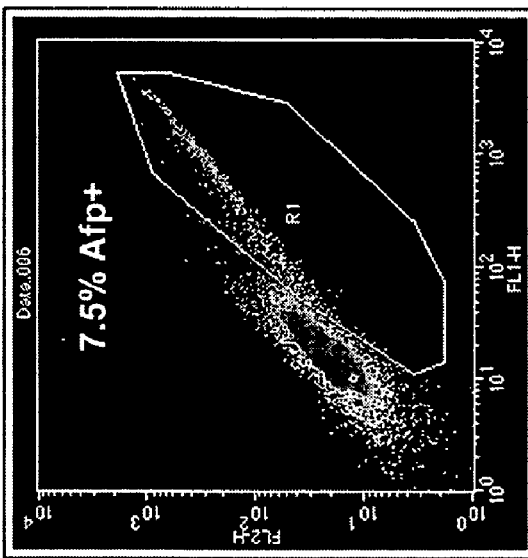
Figure 10:
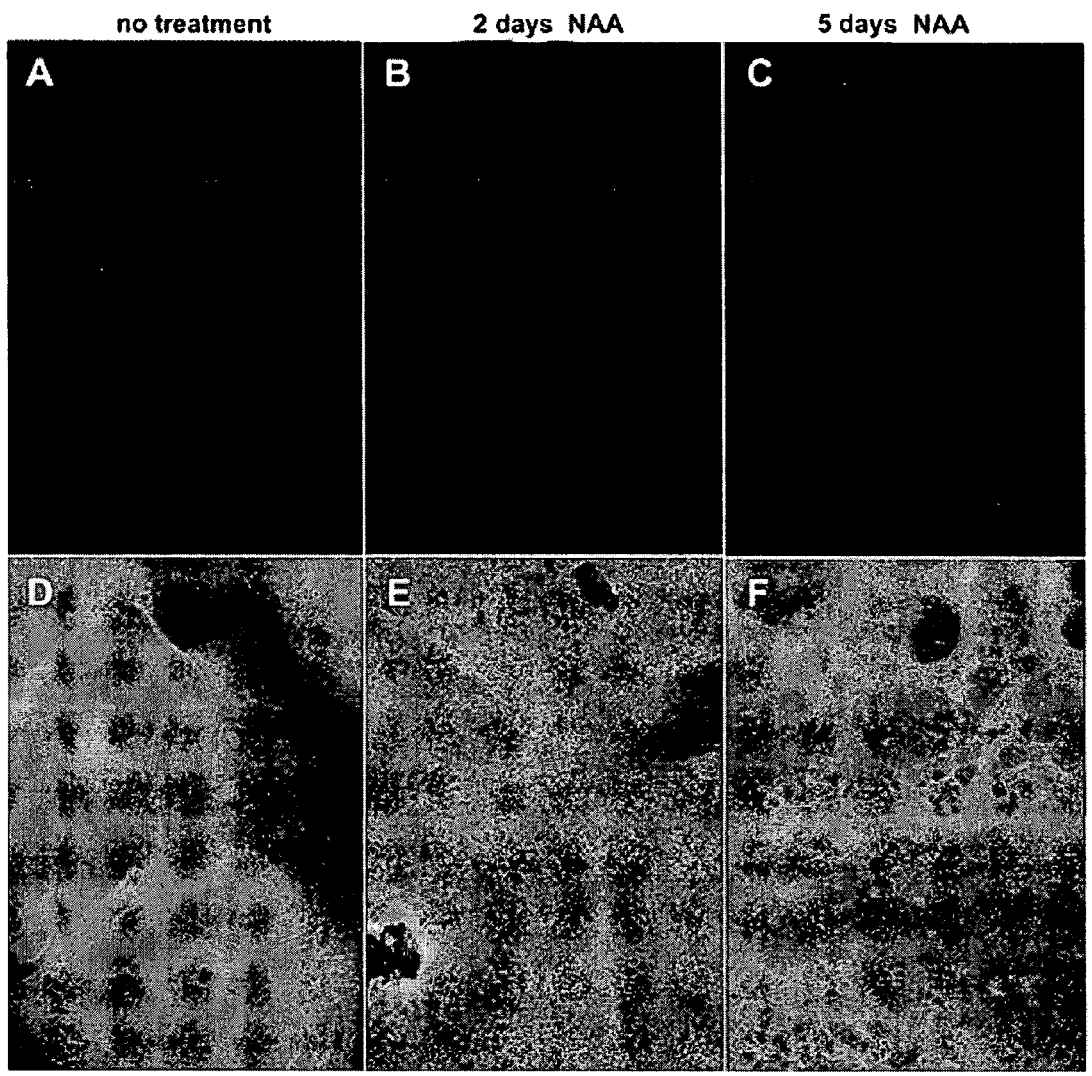
FIGS. 10A-F are micrographs which show that exposure of hESCs to nodal, activin A and activin B (NAA) yields a striking increase in the number of SOX17$^+$ cells over the period of 5 days (A-C). By comparing to the relative abundance of SOX17$^+$ cells to the total number of cells present in each field, as indicated by DAPI stained nuclei (D-F), it can be seen that approximately 30-50% of all cells are immunoreactive for SOX17 after five days treatment with NAA.
Figure 11:
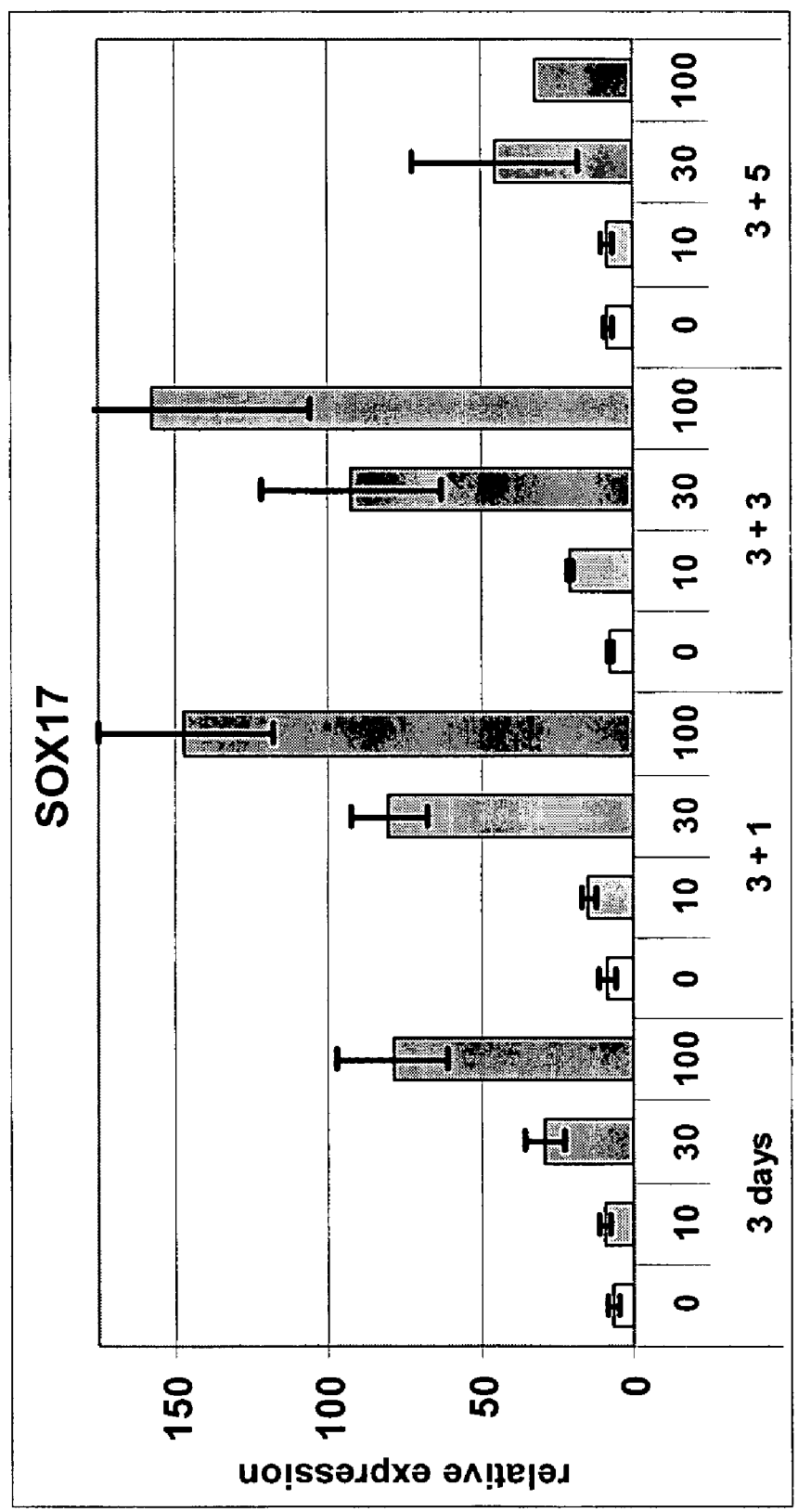
FIG. 11 is a bar chart which demonstrates that activin A (0, 10, 30 or 100 ng/ml) dose-dependently increases SOX17 gene expression in differentiating hESCs. Increased expression is already robust after 3 days of treatment on adherent cultures and continues through subsequent 1, 3 and 5 days of suspension culture as well.
Figure 12:
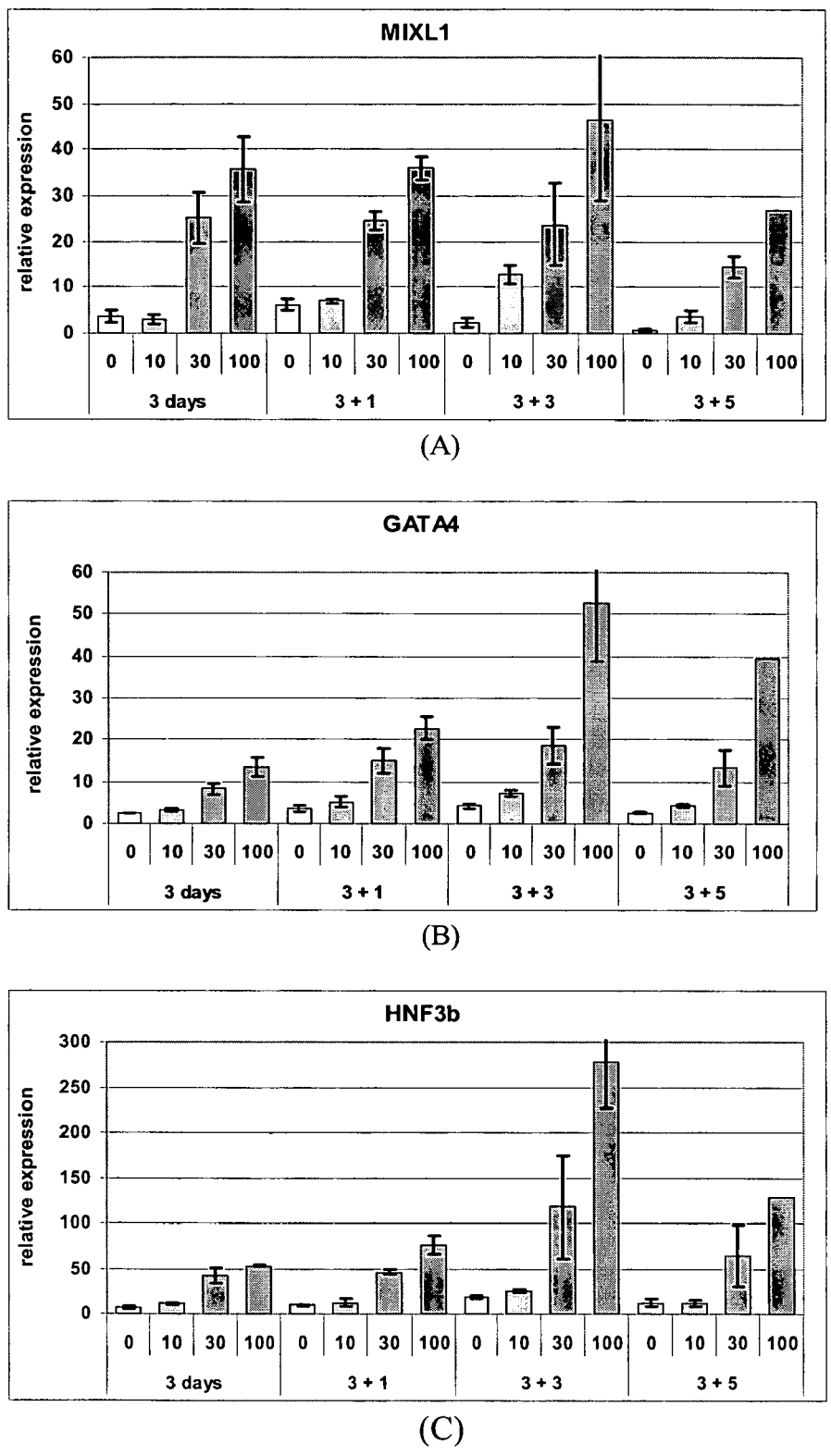
FIGS. 12A-C are bar charts which demonstrate the effect of activin A on the expression of MIXL1 (panel A), GATA4 (panel B) and HNF3b (panel C). Activin A dose-dependent increases are also observed for three other markers of definitive endoderm; MIXL1, GATA4 and HNF3b. The magnitudes of increased expression in response to activin dose are strikingly similar to those observed for SOX17, strongly indicating that activin A is specifying a population of cells that co-express all four genes (SOX17$^+$, MIXL1$^+$, GATA4$^+$ and HNF3b$^+$).
Figure 13:
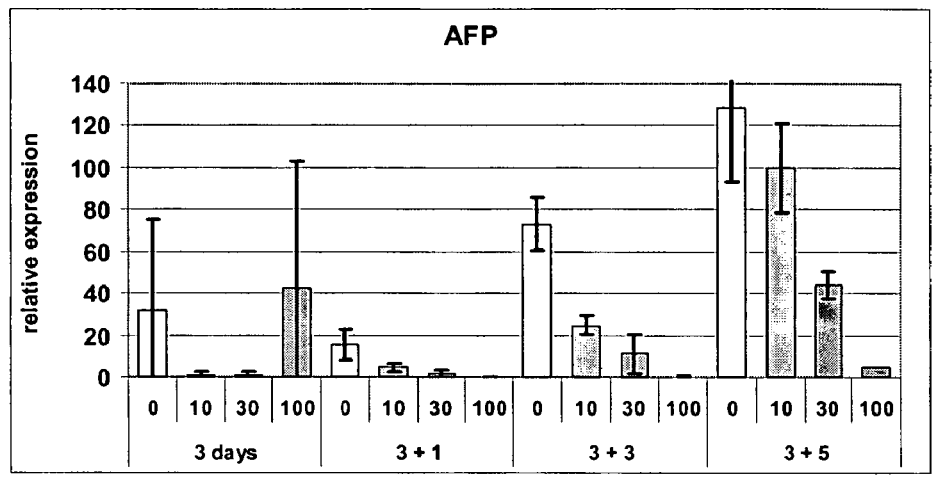
FIGS. 13A-C are bar charts which demonstrate the effect of activin A on the expression of AFP (panel A), SOX7 (panel B) and SPARC (panel C). There is an activin A dose-dependent decrease in expression of the visceral endoderm marker AFP. Markers of primitive endoderm (SOX7) and parietal endoderm (SPARC) remain either unchanged or exhibit suppression at some time points indicating that activin A does not act to specify these extra-embryonic endoderm cell types. This further supports the fact that the increased expression of SOX17, MIXL1, GATA4, and HNF3b are due to an increase in the number of definitive endoderm cells in response to activin A.
Figure 13:
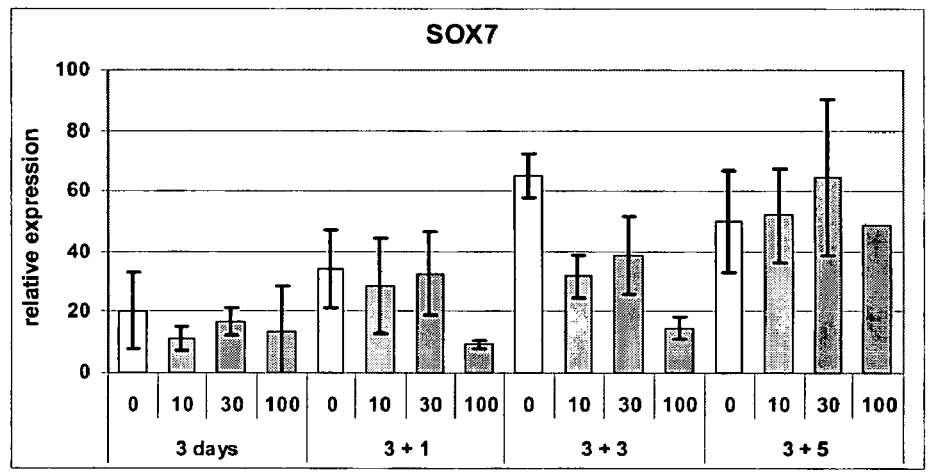
Figure 13:
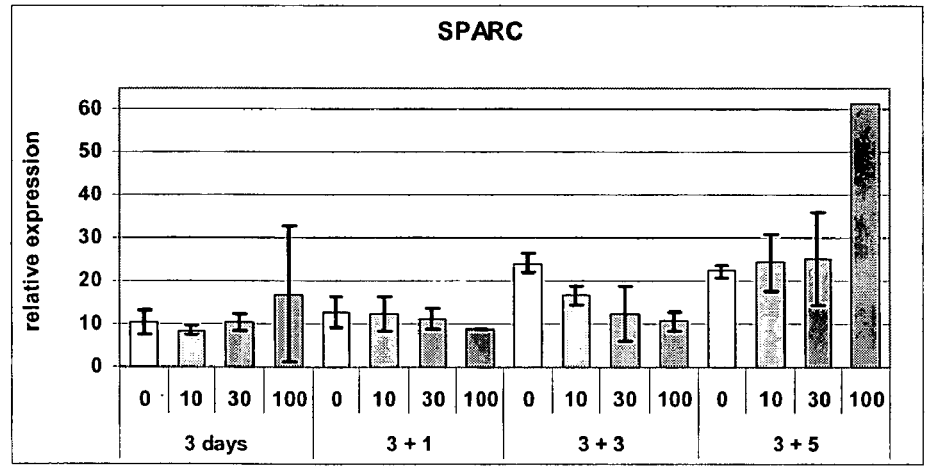
Figure 14:
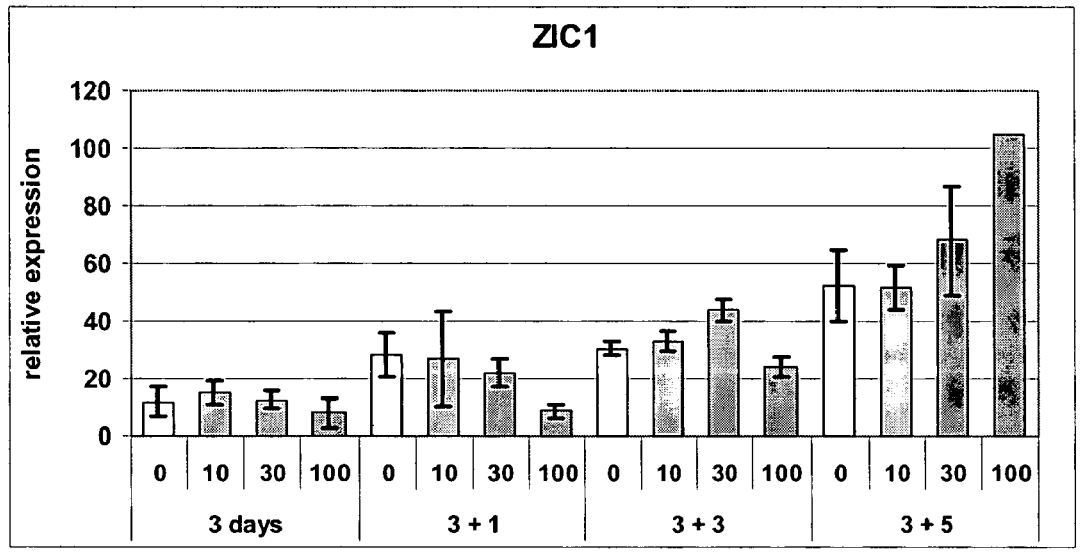
FIGS. 14A-B are bar charts showing the effect of activin A on ZIC1 (panel A) and Brachyury expression (panel B) Consistent expression of the neural marker ZIC1 demonstrates that there is not a dose-dependent effect of activin A on neural differentiation. There is a notable suppression of mesoderm differentiation mediated by 100 ng/ml of activin A treatment as indicated by the decreased expression of brachyury. This is likely the result of the increased specification of definitive endoderm from the mesendoderm precursors. Lower levels of activin A treatment (10 and 30 ng/ml) maintain the expression of brachyury at later time points of differentiation relative to untreated control cultures.
Figure 14:
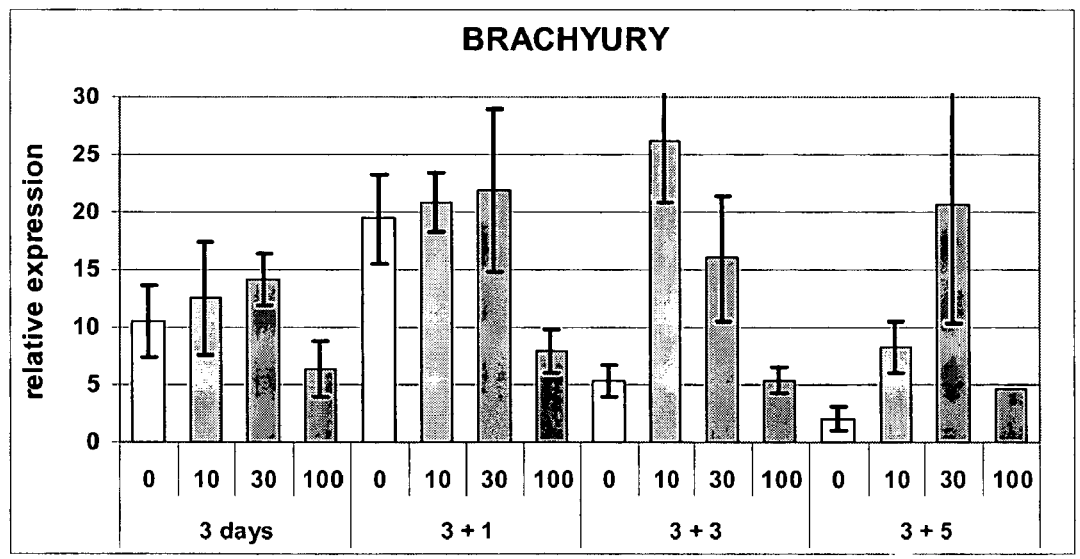

As a further evidence of the specificity of the SOX17$^{hi}$/AFP$^{lo}$/TM$^{lo}$/SPARC$^{lo}$ marker profile as predictive of definitive endoderm, SOX17 and AFP gene expression was quantitatively compared to the relative number of antibody labeled cells. As shown in FIG. 7A, hESCs treated with retinoic acid (visceral endoderm inducer), or activin A (definitive endoderm inducer), resulted in a 10-fold difference in the level of SOX17 mRNA expression. This result mirrored the 10-fold difference in SOX17 antibody-labeled cell number (FIG. 7B). Furthermore, as shown in FIG. 8A, activin A treatment of hESCs suppressed AFP gene expression by 6.8-fold in comparison to no treatment. This was visually reflected by a dramatic decrease in the number of AFP labeled cells in these cultures as shown in FIGS. 8B-C. To quantify this further, it was demonstrated that this approximately 7-fold decrease in AFP gene expression was the result of a similar 7-fold decrease in AFP antibody-labeled cell number as measured by flow cytometry (FIGS. 9A-B). This result is extremely significant in that it indicates that quantitative changes in gene expression as seen by Q-PCR mirror changes in cell type specification as observed by antibody staining.

Incubation of hESCs in the presence of Nodal family members (Nodal, activin A and activin B—NAA) resulted in a significant increase in SOX17 antibody-labeled cells over time. By 5 days of continuous activin treatment greater than 50% of the cells were labeled with SOX17 (FIGS. 10A-F). There were few or no cells labeled with AFP after 5 days of activin treatment.

In summary, the antibody produced against the carboxy-terminal 242 amino acids of the human SOX17 protein identified human SOX17 protein on Western blots but did not recognize SOX7, it's closest Sox family relative. The SOX17 antibody recognized a subset of cells in differentiating hESC cultures that were primarily SOX17$^+$/AFP$^{lo/-}$ (greater than 95% of labeled cells) as well as a small percentage (<5%) of cells that co-label for SOX17 and AFP (visceral endoderm). Treatment of hESC cultures with activins resulted in a marked elevation of SOX17 gene expression as well as SOX17 labeled cells and dramatically suppressed the expression of AFP mRNA and the number of cells labeled with AFP antibody.

Example 5

Q-PCR Gene Expression Assay

In the following experiments, real-time quantitative RT-PCR (Q-PCR) was the primary assay used for screening the effects of various treatments on hESC differentiation. In particular, real-time measurements of gene expression were analyzed for multiple marker genes at multiple time points by Q-PCR. Marker genes characteristic of the desired as well as undesired cell types were evaluated to gain a better understanding of the overall dynamics of the cellular populations. The strength of Q-PCR analysis includes its extreme sensitivity and relative ease of developing the necessary markers, as the genome sequence is readily available. Furthermore, the extremely high sensitivity of Q-PCR permits detection of gene expression from a relatively small number of cells within a much larger population. In addition, the ability to detect very low levels of gene expression provides indications for "differentiation bias" within the population. The bias towards a particular differentiation pathway, prior to the overt differentiation of those cellular phenotypes, is unrecognizable using immunocytochemical techniques. For this reason, Q-PCR provides a method of analysis that is at least complementary and potentially much superior to immunocytochemical techniques for screening the success of differentiation treatments. Additionally, Q-PCR provides a mechanism by which to evaluate the success of a differentiation protocol in a quantitative format at semi-high throughput scales of analysis.

The approach taken here was to perform relative quantitation using SYBR Green chemistry on a Rotor Gene 3000 instrument (Corbett Research) and a two-step RT-PCR format. Such an approach allowed for the banking of cDNA samples for analysis of additional marker genes in the future, thus avoiding variability in the reverse transcription efficiency between samples.

Primers were designed to lie over exon-exon boundaries or span introns of at least 800 bp when possible, as this has been empirically determined to eliminate amplification from contaminating genomic DNA. When marker genes were employed that do not contain introns or they possess pseudogenes, DNase I treatment of RNA samples was performed.

We routinely used Q-PCR to measure the gene expression of multiple markers of target and non-target cell types in order to provide a broad profile description of gene expression in cell samples. The markers relevant for the early phases of hESC differentiation (specifically ectoderm, mesoderm, definitive endoderm and extra-embryonic endoderm) and for which validated primer sets are available are provided below in Table 1. The human specificity of these primer sets has also been demonstrated. This is an important fact since the hESCs were often grown on mouse feeder layers. Most typically, triplicate samples were taken for each condition and independently analyzed in duplicate to assess the biological variability associated with each quantitative determination.

To generate PCR template, total RNA was isolated using RNeasy (Qiagen) and quantitated using RiboGreen (Molecular Probes). Reverse transcription from 350-500 ng of total RNA was carried out using the iScript reverse transcriptase kit (BioRad), which contains a mix of oligo-dT and random primers. Each 20 µL reaction was subsequently diluted up to 100 µL total volume and 3 µL was used in each 10 µL Q-PCR reaction containing 400 nM forward and reverse primers and 5 µL 2× SYBR Green master mix (Qiagen). Two step cycling parameters were used employing a 5 second denature at 85-94° C. (specifically selected according to the melting temp of the amplicon for each primer set) followed by a 45 second anneal/extend at 60° C. Fluorescence data was collected during the last 15 seconds of each extension phase. A three point, 10-fold dilution series was used to generate the standard curve for each run and cycle thresholds (Ct's) were converted to quantitative values based on this standard curve. The quantitated values for each sample were normalized to housekeeping gene performance and then average and standard deviations were calculated for triplicate samples. At the conclusion of PCR cycling, a melt curve analysis was performed to ascertain the specificity of the reaction. A single specific product was indicated by a single peak at the $T_m$ appropriate for that PCR amplicon. In addition, reactions performed without reverse transcriptase served as the negative control and do not amplify.

A first step in establishing the Q-PCR methodology was validation of appropriate housekeeping genes (HGs) in the experimental system. Since the HG was used to normalize across samples for the RNA input, RNA integrity and RT efficiency, it was of value that the HG exhibited a constant level of expression over time in all sample types in order for the normalization to be meaningful. We measured the expression levels of Cyclophilin G, hypoxanthine phosphoribosyl-transferase 1 (HPRT), beta-2-microglobulin, hydroxymethylbiane synthase (HMBS), TATA-binding protein (TBP), and glucoronidase beta (GUS) in differentiating hESCs. Our results indicated that beta-2-microglobulin expression levels increased over the course of differentiation and therefore we excluded the use of this gene for normalization. The other genes exhibited consistent expression levels over time as well as across treatments. We routinely used both Cyclophilin G and GUS to calculate a normalization factor for all samples. The use of multiple HGs simultaneously reduces the variability inherent to the normalization process and increases the reliability of the relative gene expression values.

After obtaining genes for use in normalization, Q-PCR was then utilized to determine the relative gene expression levels of many marker genes across samples receiving different experimental treatments. The marker genes employed have been chosen because they exhibit enrichment in specific populations representative of the early germ layers and in particular have focused on sets of genes that are differentially expressed in definitive endoderm and extra-embryonic endoderm. These genes as well as their relative enrichment profiles are highlighted in Table 1.

TABLE 1

| Germ Layer | Gene | Expression Domains |
|---|---|---|
| Endoderm | SOX17 | definitive, visceral and parietal endoderm |
| | MIXL1 | endoderm and mesoderm |
| | GATA4 | definitive and primitive endoderm |
| | HNF3b | definitive endoderm and primitive endoderm, mesoderm, neural plate |
| | GSC | endoderm and mesoderm |
| Extra-embryonic | SOX7 | visceral endoderm |
| | AFP | visceral endoderm, liver |
| | SPARC | parietal endoderm |
| | TM | parietal endoderm/trophectoderm |
| Ectoderm | ZIC1 | neural tube, neural progenitors |
| Mesoderm | BRACH | nascent mesoderm |

Since many genes are expressed in more than one germ layer it is useful to quantitatively compare expression levels of many genes within the same experiment. SOX17 is expressed in definitive endoderm and to a smaller extent in visceral and parietal endoderm. SOX7 and AFP are expressed in visceral endoderm at this early developmental time point. SPARC and TM are expressed in parietal endoderm and Brachyury is expressed in early mesoderm.

Definitive endoderm cells were predicted to express high levels of SOX17 mRNA and low levels of AFP and SOX7 (visceral endoderm), SPARC (parietal endoderm) and Brachyury (mesoderm). In addition, ZIC1 was used here to further rule out induction of early ectoderm. Finally, GATA4 and HNF3b were expressed in both definitive and extra-embryonic endoderm, and thus, correlate with SOX17 expression in definitive endoderm (Table 1). A representative experiment is shown in FIGS. 11-14 which demonstrates how the marker genes described in Table 1 correlate with each other among the various samples, thus highlighting specific patterns of differentiation to definitive endoderm and extra-embryonic endoderm as well as to mesodermal and neural cell types.

In view of the above data it is clear that increasing doses of activin resulted in increasing SOX17 gene expression. Further this SOX17 expression predominantly represented definitive endoderm as opposed to extra-embryonic endoderm. This conclusion stems from the observation that SOX17 gene expression was inversely correlated with AFP, SOX7, and SPARC gene expression.

Example 6

Directed Differentiation of Human ES Cells to Definitive Endoderm

Human ES cell cultures randomly differentiate if cultured under conditions that do not actively maintain their undifferentiated state. This heterogeneous differentiation results in production of extra-embryonic endoderm cells comprised of both parietal and visceral endoderm (AFP, SPARC and SOX7 expression) as well as early ectodermal and mesodermal derivatives as marked by ZIC1 and Nestin (ectoderm) and Brachyury (mesoderm) expression. Definitive endoderm cell appearance has not been examined or specified for lack of specific antibody markers in ES cell cultures. As such, and by default, early definitive endoderm production in ES cell cultures has not been well studied. Since satisfactory antibody reagents for definitive endoderm cells have been unavailable, most of the characterization has focused on ectoderm and extra-embryonic endoderm. Overall, there are significantly greater numbers of extra-embryonic and neurectodermal cell types in comparison to SOX17$^{hi}$ definitive endoderm cells in randomly differentiated ES cell cultures.

As undifferentiated hESC colonies expand on a bed of fibroblast feeders, the cells at the edges of the colony take on alternative morphologies that are distinct from those cells residing within the interior of the colony. Many of these outer edge cells can be distinguished by their less uniform, larger cell body morphology and by the expression of higher levels of OCT4. It has been described that as ES cells begin to differentiate they alter the levels of OCT4 expression up or down relative to undifferentiated ES cells. Alteration of OCT4 levels above or below the undifferentiated threshold may signify the initial stages of differentiation away from the pluripotent state.

When undifferentiated colonies were examined by SOX17 immunocytochemistry, occasionally small 10-15-cell clusters of SOX17-positive cells were detected at random locations on the periphery and at the junctions between undifferentiated hESC colonies. As noted above, these scattered pockets of outer colony edges appeared to be some of the first cells to differentiate away from the classical ES cell morphology as the colony expanded in size and became more crowded. Younger, smaller fully undifferentiated colonies (<1 mm; 4-5 days old) showed no SOX17 positive cells within or at the edges of the colonies while older, larger colonies (1-2 mm diameter, >5 days old) had sporadic isolated patches of SOX17 positive, AFP negative cells at the periphery of some colonies or in regions interior to the edge that did not display the classical hESC morphology described previously. Given that this was the first development of an effective SOX17 antibody, definitive endoderm cells generated in such early "undifferentiated" ES cell cultures have never been previously demonstrated.

Figure 15:
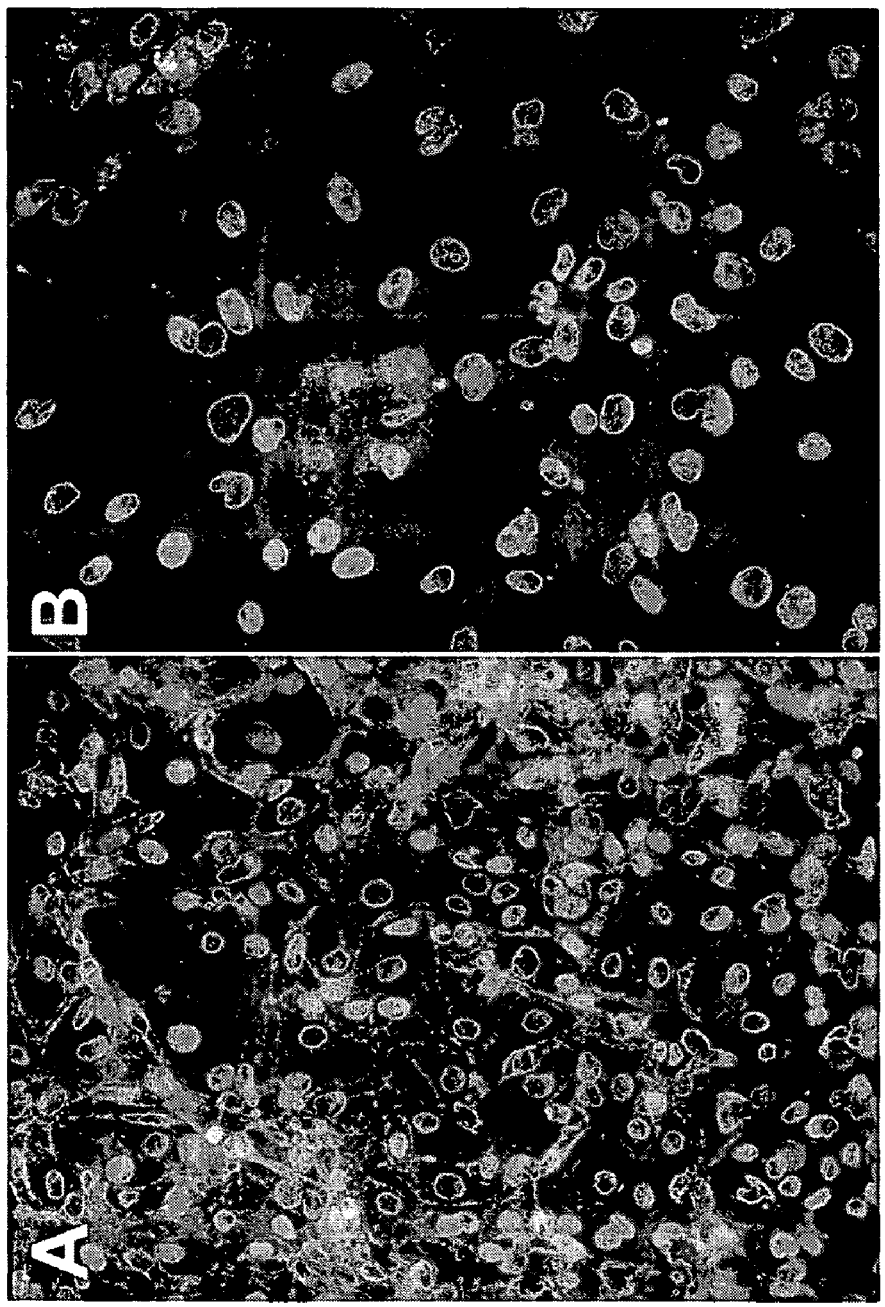
FIGS. 15A-B are micrographs showing decreased parietal endoderm differentiation in response to treatment with activins. Regions of TM$^{hi}$ parietal endoderm are found through the culture (A) when differentiated in serum alone, while differentiation to TM$^+$ cells is scarce when activins are included (B) and overall intensity of TM immunoreactivity is lower.
Figure 16:
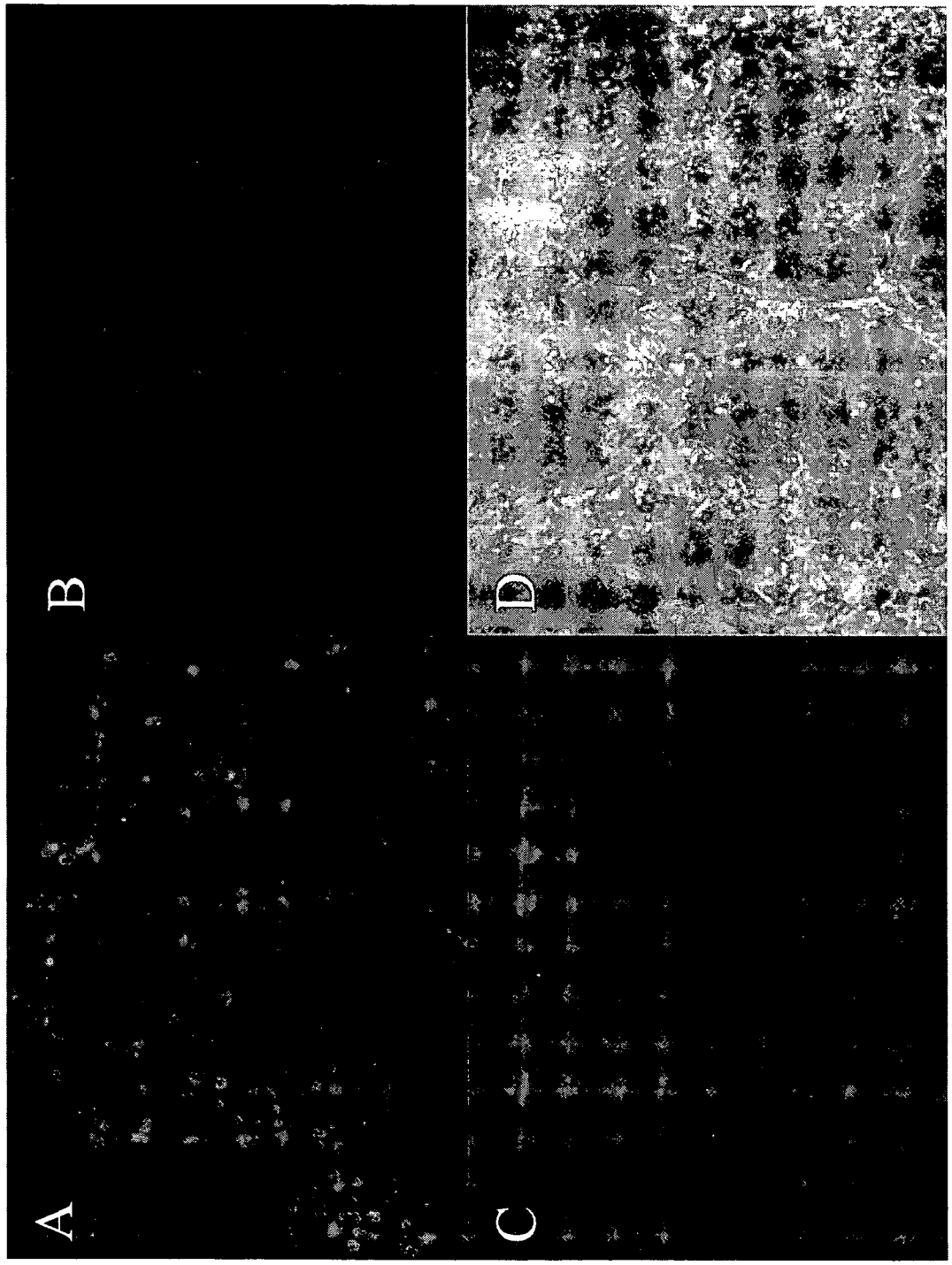
FIGS. 16A-D are micrographs which show marker expression in response to treatment with activin A and activin B. hESCs were treated for four consecutive days with activin A and activin B and triple labeled with SOX17, AFP and TM antibodies. Panel A—SOX17; Panel B—AFP; Panel C—TM; and Panel D—Phase/DAPI. Notice the numerous SOX17 positive cells (A) associated with the complete absence of AFP (B) and TM (C) immunoreactivity.
Figure 17:
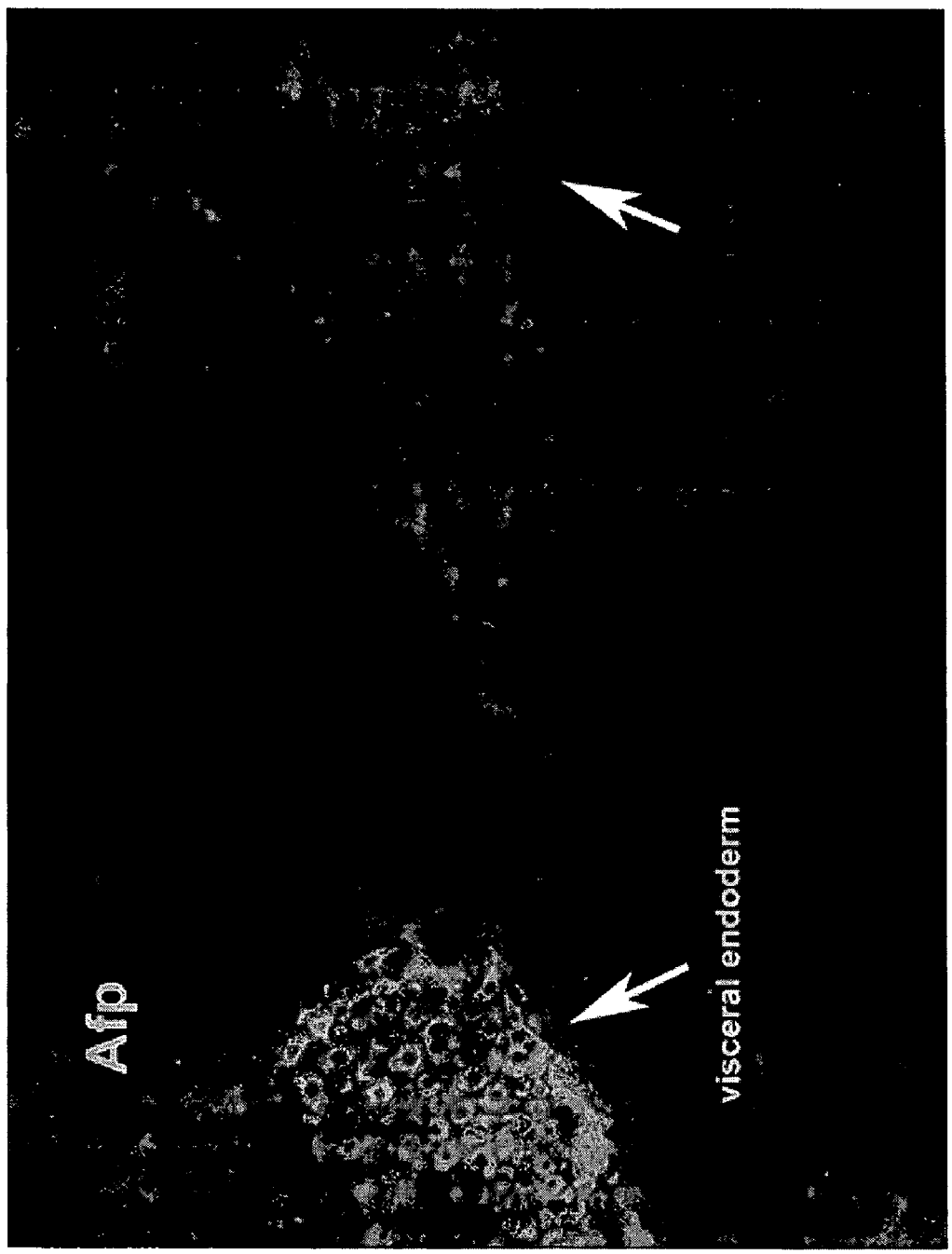
FIG. 17 is a micrograph showing the appearance of definitive endoderm and visceral endoderm in vitro from hESCs. The regions of visceral endoderm are identified by AFP$^{hi}$/SOX17$^{lo/-}$ while definitive endoderm displays the complete opposite profile, SOX17$^{hi}$/AFP$^{lo/-}$. This field was selectively chosen due to the proximity of these two regions to each other. However, there are numerous times when SOX17$^{hi}$/AFP$^{lo/-}$ regions are observed in absolute isolation from any regions of AFP$^{hi}$ cells, suggesting the separate origination of the definitive endoderm cells from visceral endoderm cells.
Figure 18:
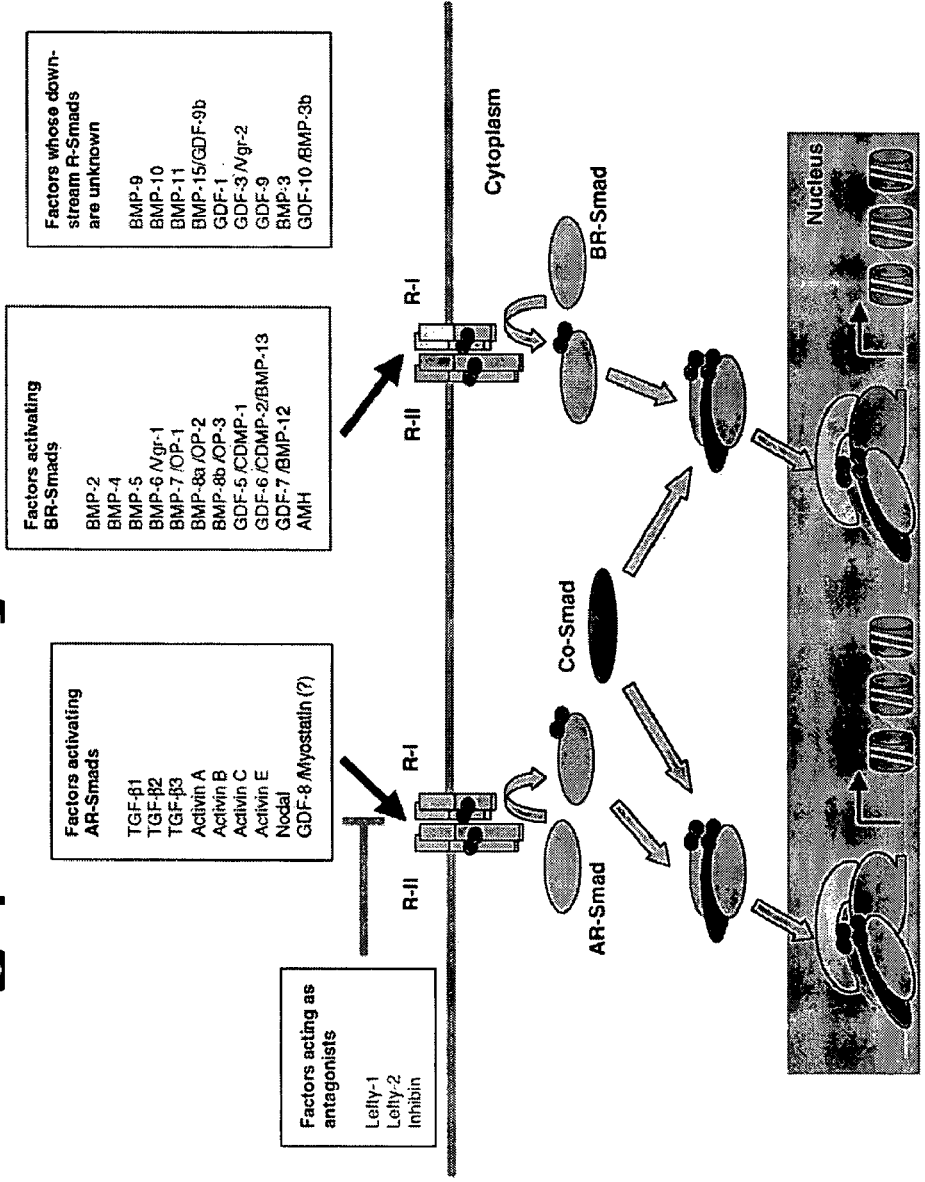
FIG. 18 is a diagram depicting the TGFβ family of ligands and receptors. Factors activating AR Smads and BR Smads are useful in the production of definitive endoderm from human embryonic stem cells (see, *J Cell Physiol.* 187:265-76).

Based on negative correlations of SOX17 and SPARC gene expression levels by Q-PCR, the vast majority of these SOX17 positive, AFP negative cells will be negative for parietal endoderm markers by antibody co-labeling. This was specifically demonstrated for TM-expressing parietal endoderm cells as shown in FIGS. 15A-B. Exposure to Nodal factors activin A and B resulted in a dramatic decrease in the intensity of TM expression and the number of TM positive cells. By triple labeling using SOX17, AFP and TM antibodies on an activin treated culture, clusters of SOX17 positive cells that were also negative for AFP and TM were observed (FIGS. 16A-D). These are the first cellular demonstrations of SOX17 positive definitive endoderm cells in differentiating hESC cultures (FIGS. 16A-D and 17).

With the SOX17 antibody and Q-PCR tools described above we have explored a number of procedures capable of efficiently programming hESCs to become SOX17$^{hi}$/AFP$^{lo}$/SPARC/TM$^{lo}$ definitive endoderm cells. We applied a variety of differentiation protocols aimed at increasing the number and proliferative capacity of these cells as measured at the population level by Q-PCR for SOX17 gene expression and at the level of individual cells by antibody labeling of SOX17 protein.

We were the first to analyze and describe the effect of TGFβ family growth factors, such as Nodal/activin/BMP, for use in creating definitive endoderm cells from embryonic stem cells in in vitro cell cultures. In typical experiments, activin A, activin B, BMP or combinations of these growth factors were added to cultures of undifferentiated human stem cell line hESCyt-25 to begin the differentiation process.

Figure 19:
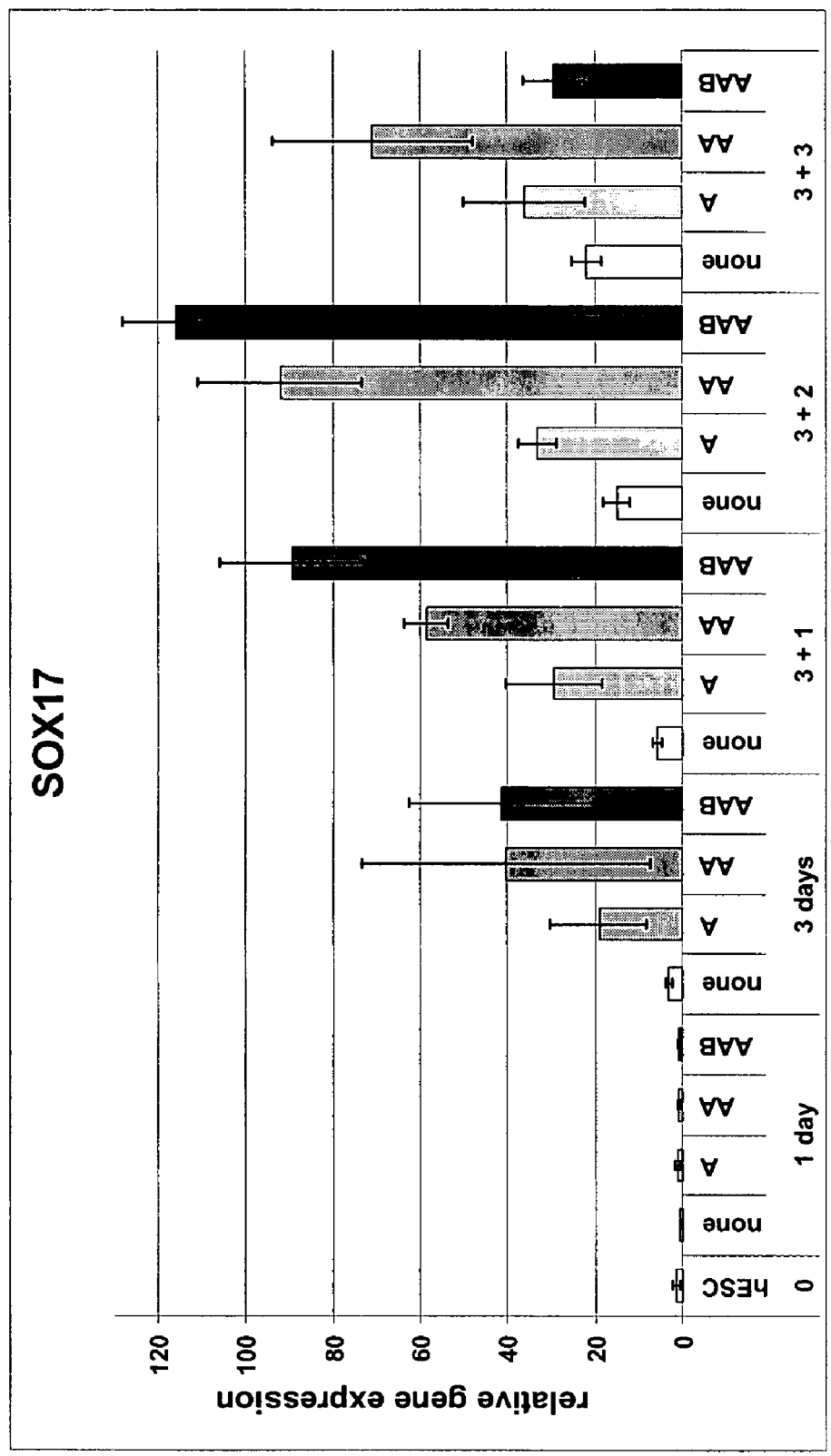
FIG. 19 is a bar chart showing the induction of SOX17 expression over time as a result of treatment with individual and combinations of TGFβ factors.

As shown in FIG. 19, addition of activin A at 100 ng/ml resulted in a 19-fold induction of SOX17 gene expression vs. undifferentiated hESCs by day 4 of differentiation. Adding activin B, a second member of the activin family, together with activin A, resulted in a 37-fold induction over undifferentiated hESCs by day 4 of combined activin treatment. Finally, adding a third member of the TGFβ family from the Nodal/Activin and BMP subgroups, BMP4, together with activin A and activin B, increased the fold induction to 57 times that of undifferentiated hESCs (FIG. 19). When SOX17 induction with activins and BMP was compared to no factor medium controls 5-, 10-, and 15-fold inductions resulted at the 4-day time point. By five days of triple treatment with activins A, B and BMP, SOX17 was induced more than 70 times higher than hESCs. These data indicate that higher doses and longer treatment times of the Nodal/activin TGFβ family members results in increased expression of SOX17.

Nodal and related molecules activin A, B and BMP facilitate the expression of SOX17 and definitive endoderm formation in vivo or in vitro. Furthermore, addition of BMP results in an improved SOX17 induction possibly through the further induction of Cripto, the Nodal co-receptor.

We have demonstrated that the combination of activins A and B together with BMP4 result in additive increases in SOX17 induction and hence definitive endoderm formation. BMP4 addition for prolonged periods (>4 days), in combination with activin A and B may induce SOX17 in parietal and visceral endoderm as well as definitive endoderm. In some embodiments of the present invention, it is therefore valuable to remove BMP4 from the treatment within 4 days of addition.

Figure 20:
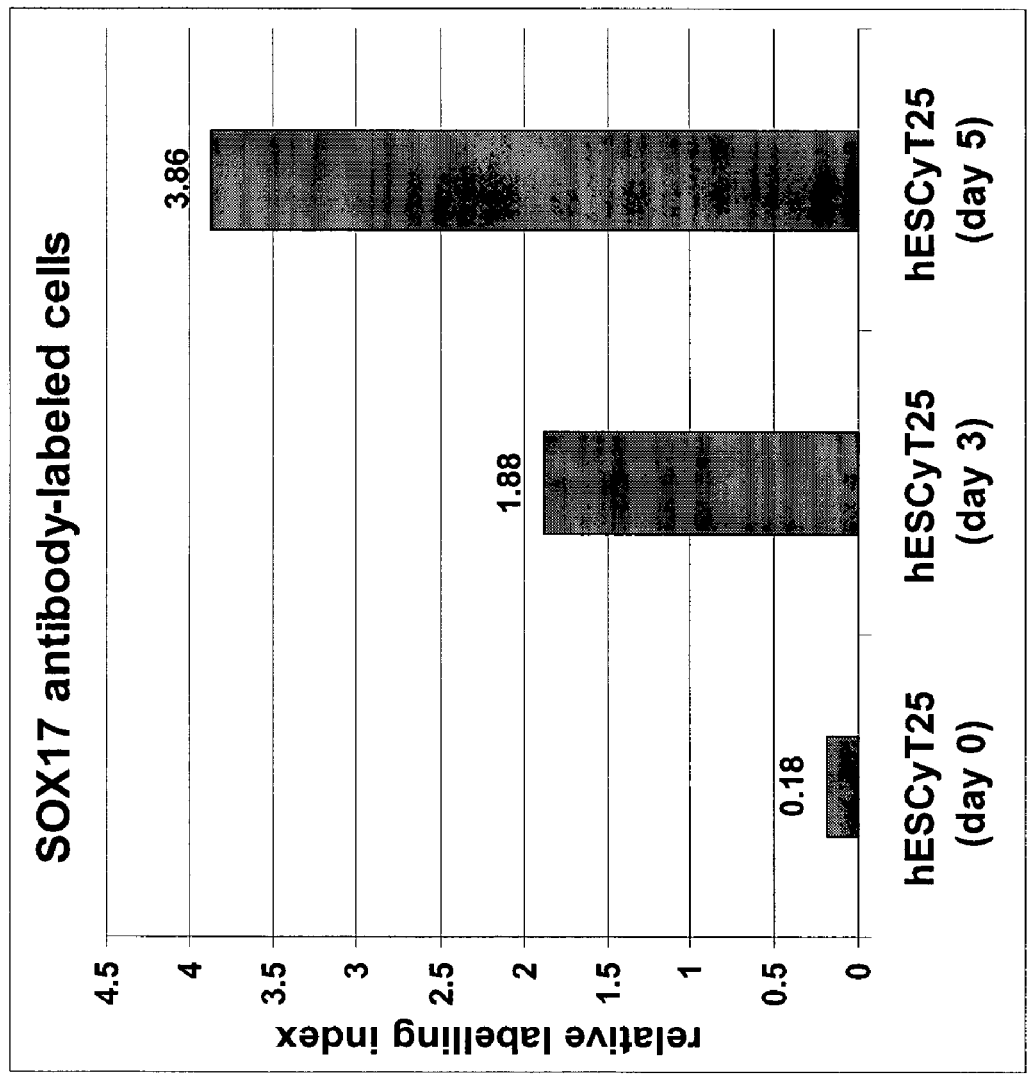
FIG. 20 is a bar chart showing the increase in SOX17+ cell number with time as a result of treatment with combinations of TGFβ factors.
Figure 21:
FIG. 21 is a bar chart showing induction of SOX17 expression over time as a result of treatment with combinations of TGFβ factors.
Figure 22:
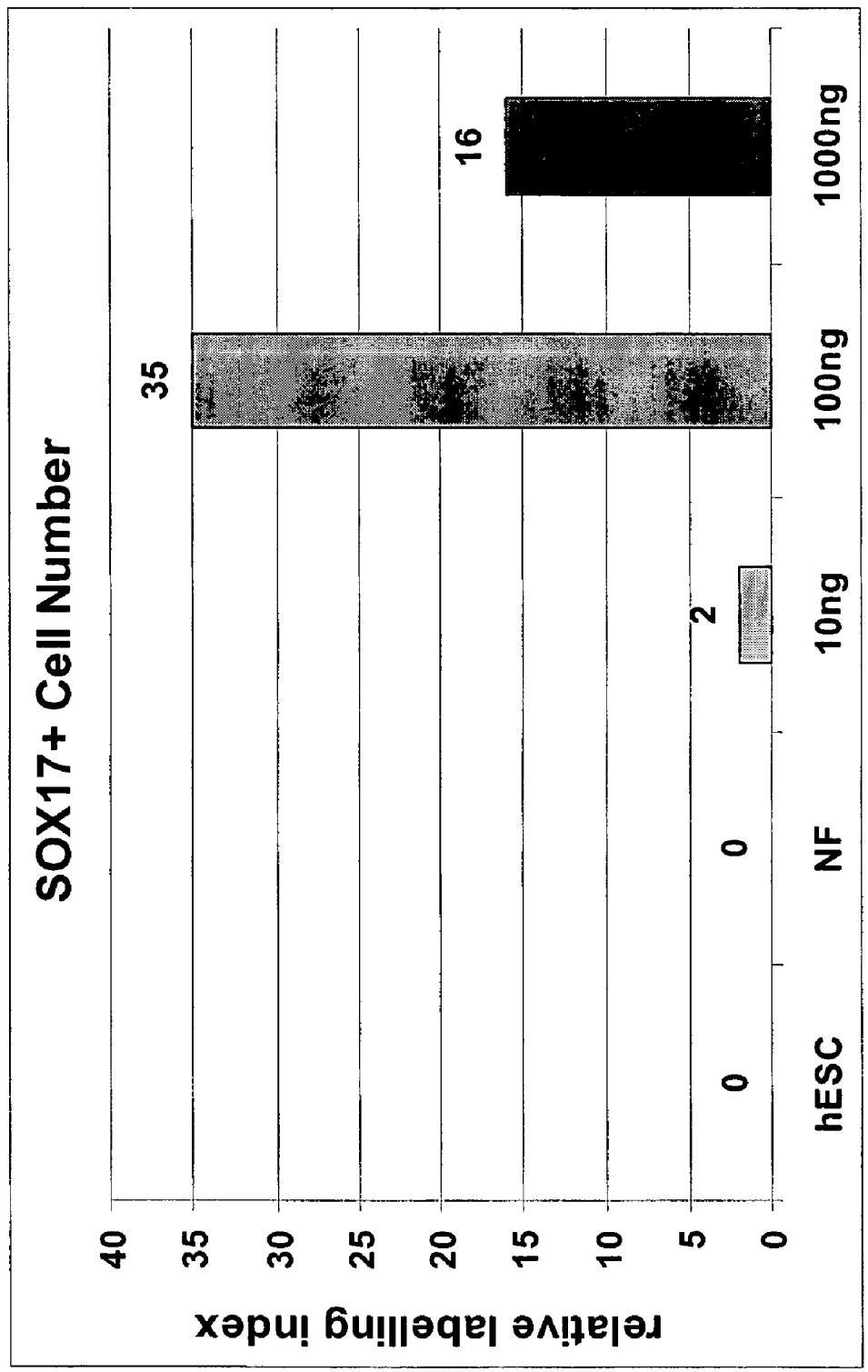
FIG. 22 is a bar chart showing that activin A induces a dose-dependent increase in SOX17+ cell number.

To determine the effect of TGFβ factor treatment at the individual cell level, a time course of TGFβ factor addition was examined using SOX17 antibody labeling. As previously shown in FIGS. 10A-F, there was a dramatic increase in the relative number of SOX17 labeled cells over time. The relative quantification (FIG. 20) shows more than a 20-fold increase in SOX17-labeled cells. This result indicates that both the numbers of cells as well SOX17 gene expression level are increasing with time of TGFβ factor exposure. As shown in FIG. 21, after four days of exposure to Nodal, activin A, activin B and BMP4, the level of SOX17 induction reached 168-fold over undifferentiated hESCs. FIG. 22 shows that the relative number of SOX17-positive cells was also dose responsive. activin A doses of 100 ng/ml or more were capable of potently inducing SOX17 gene expression and cell number.

Figure 23:
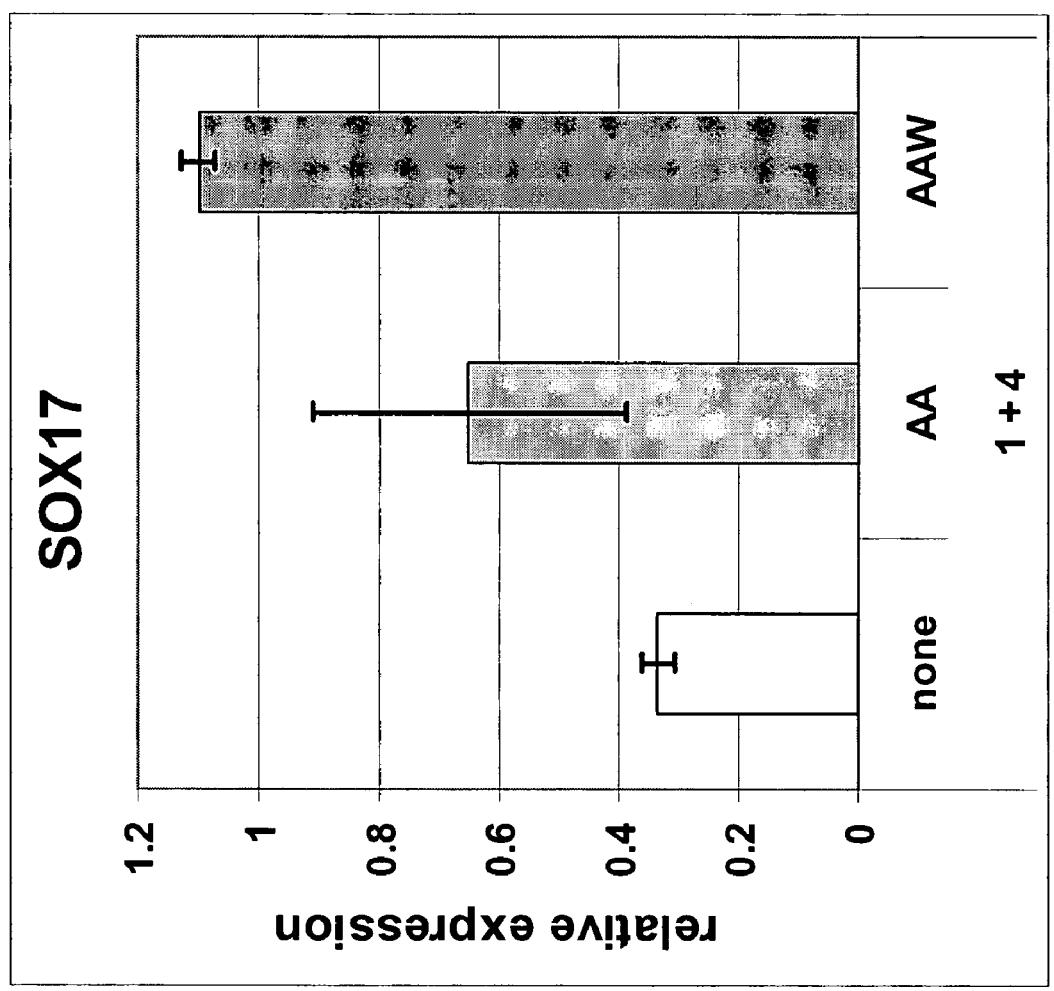
FIG. 23 is a bar chart showing that addition of Wnt3a to activin A and activin B treated cultures increases SOX17 expression above the levels induced by activin A and activin B alone.

In addition to the TGFβ family members, the Wnt family of molecules may play a role in specification and/or maintenance of definitive endoderm. The use of Wnt molecules was also beneficial for the differentiation of hESCs to definitive endoderm as indicated by the increased SOX17 gene expression in samples that were treated with activins plus Wnt3a over that of activins alone (FIG. 23).

Figure 24:
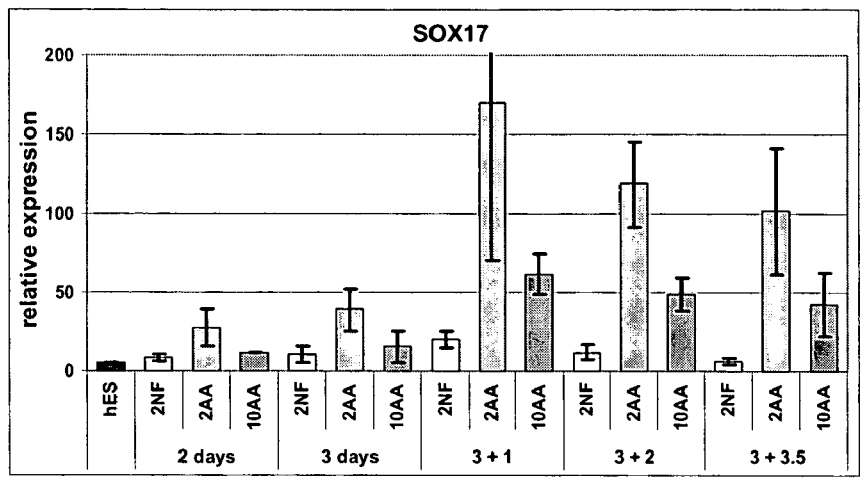
FIGS. 24A-C are bar charts showing differentiation to definitive endoderm is enhanced in low FBS conditions. Treatment of hESCs with activins A and B in media containing 2% FBS (2AA) yields a 2-3 times greater level of SOX17 expression as compared to the same treatment in 10% FBS media (10AA) (panel A). Induction of the definitive endoderm marker MIXL1 (panel B) is also affected in the same way and the suppression of AFP (visceral endoderm) (panel C) is greater in 2% FBS than in 10% FBS conditions.
Figure 24:
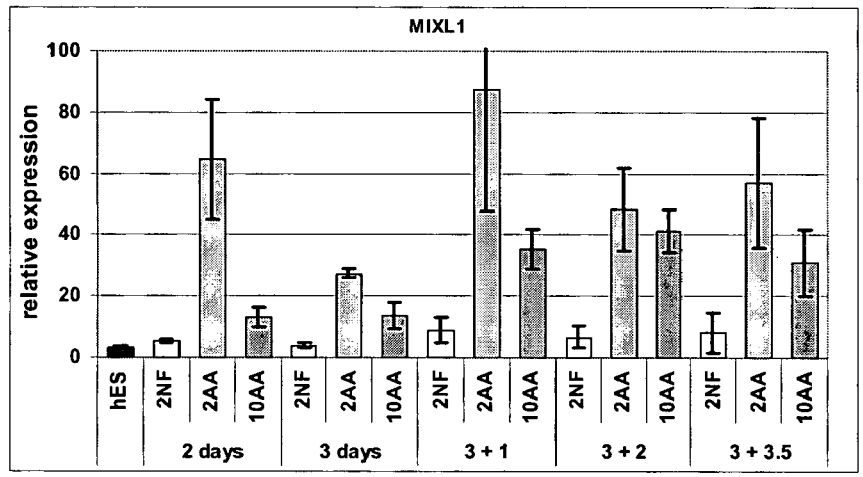
Figure 24:
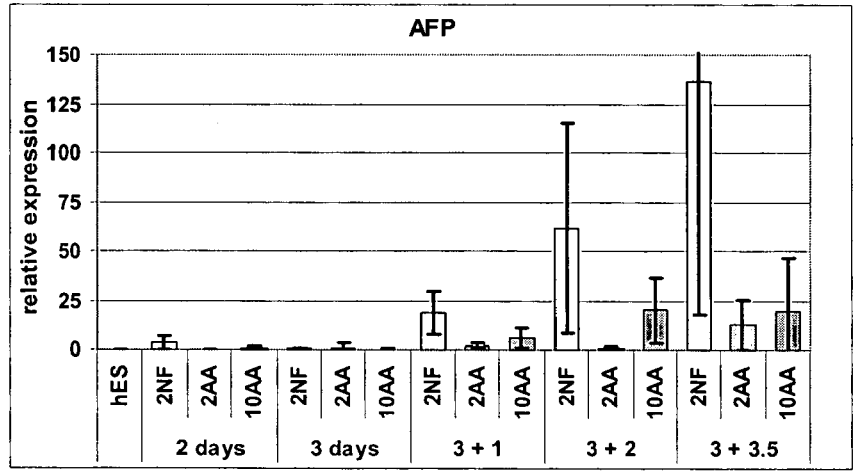
Figure 25:
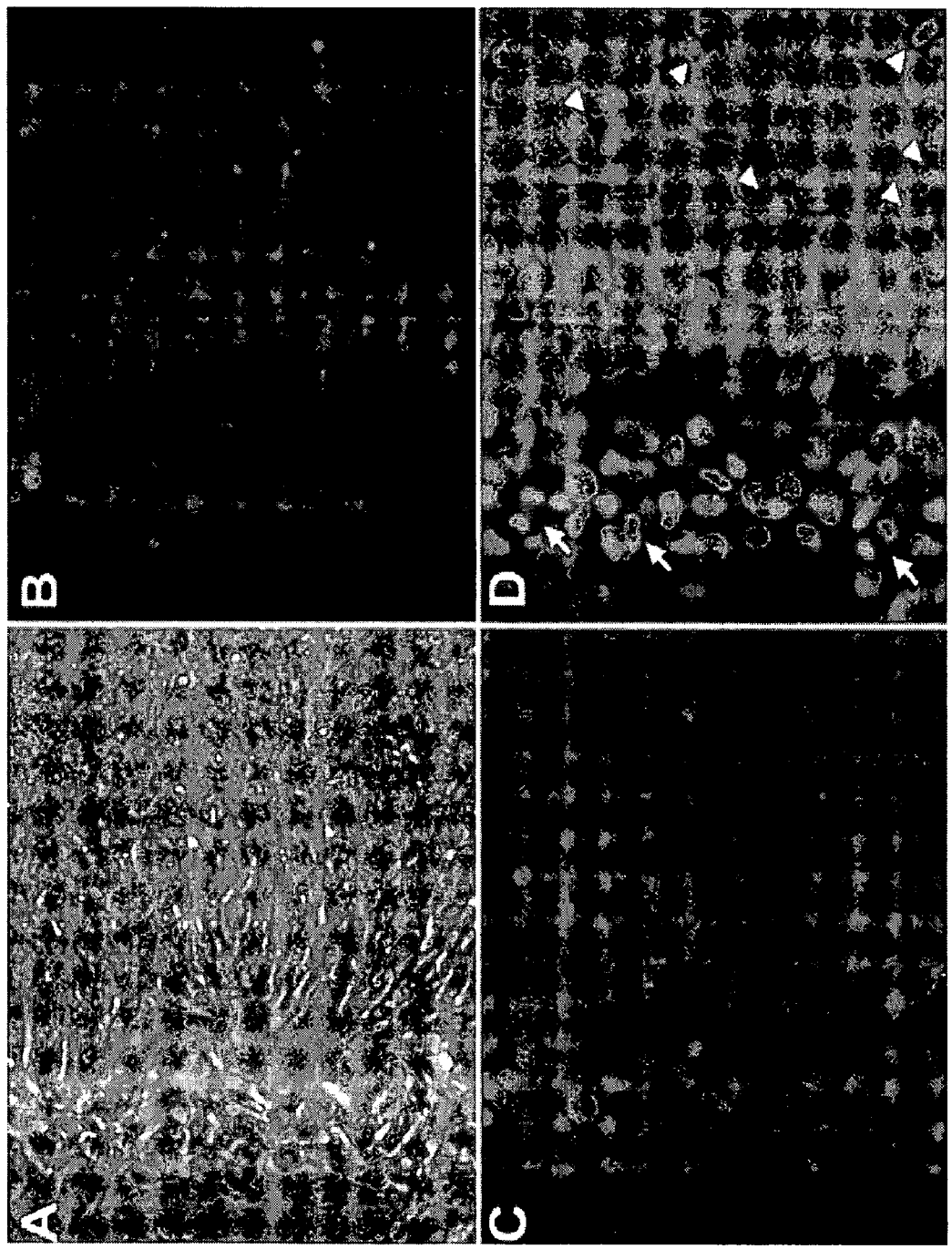
FIGS. 25A-D are micrographs which show SOX17+ cells are dividing in culture. SOX17 immunoreactive cells are present at the differentiating edge of an hESC colony (C, D) and are labeled with proliferating cell nuclear antigen (PCNA) (panel B) yet are not co-labeled with OCT4 (panel C). In addition, clear mitotic figures can be seen by DAPI labeling of nuclei in both SOX17+ cells (arrows) as well as OCT4+, undifferentiated hESCs (arrowheads) (D).

All of the experiments described above were performed using a tissue culture medium containing 10% serum with added factors. Surprisingly, we discovered that the concentration of serum had an effect on the level of SOX17 expression in the presence of added activins as shown in FIGS. 24A-C. When serum levels were reduced from 10% to 2%, SOX17 expression tripled in the presence of activins A and B.

Finally, we demonstrated that activin induced SOX17$^+$ cells divide in culture as depicted in FIGS. 25A-D. The arrows show cells labeled with SOX17/PCNA/DAPI that are in mitosis as evidenced by the PCNA/DAPI-labeled mitotic plate pattern and the phase contrast mitotic profile.

Example 7

Chemokine Receptor 4 (CXCR4) Expression Correlates with Markers for Definitive Endoderm and not Markers for Mesoderm, Ectoderm or Visceral Endoderm As described above, hESCs can be induced to differentiate to the definitive endoderm germ layer by the application of cytokines of the TGFβ family and more specifically of the activin/nodal subfamily. Additionally, we have shown that the proportion of fetal bovine serum (FBS) in the differentiation culture medium effects the efficiency of definitive endoderm differentiation from hESCs. This effect is such that at a given concentration of activin A in the medium, higher levels of FBS will inhibit maximal differentiation to definitive endoderm. In the absence of exogenous activin A, differentiation of hESCs to the definitive endoderm lineage is very inefficient and the FBS concentration has much milder effects on the differentiation process of hESCs.

In these experiments, hESCs were differentiated by growing in RPMI medium (Invitrogen, Carlsbad, Calif.; cat# 61870-036) supplemented with 0.5%, 2.0% or 10% FBS and either with or without 100 ng/ml activin A for 6 days. In addition, a gradient of FBS ranging from 0.5% to 2.0% over the first three days of differentiation was also used in conjunction with 100 ng/ml of activin A. After the 6 days, replicate samples were collected from each culture condition and analyzed for relative gene expression by real-time quantitative PCR. The remaining cells were fixed for immunofluorescent detection of SOX17 protein.

Figure 26:
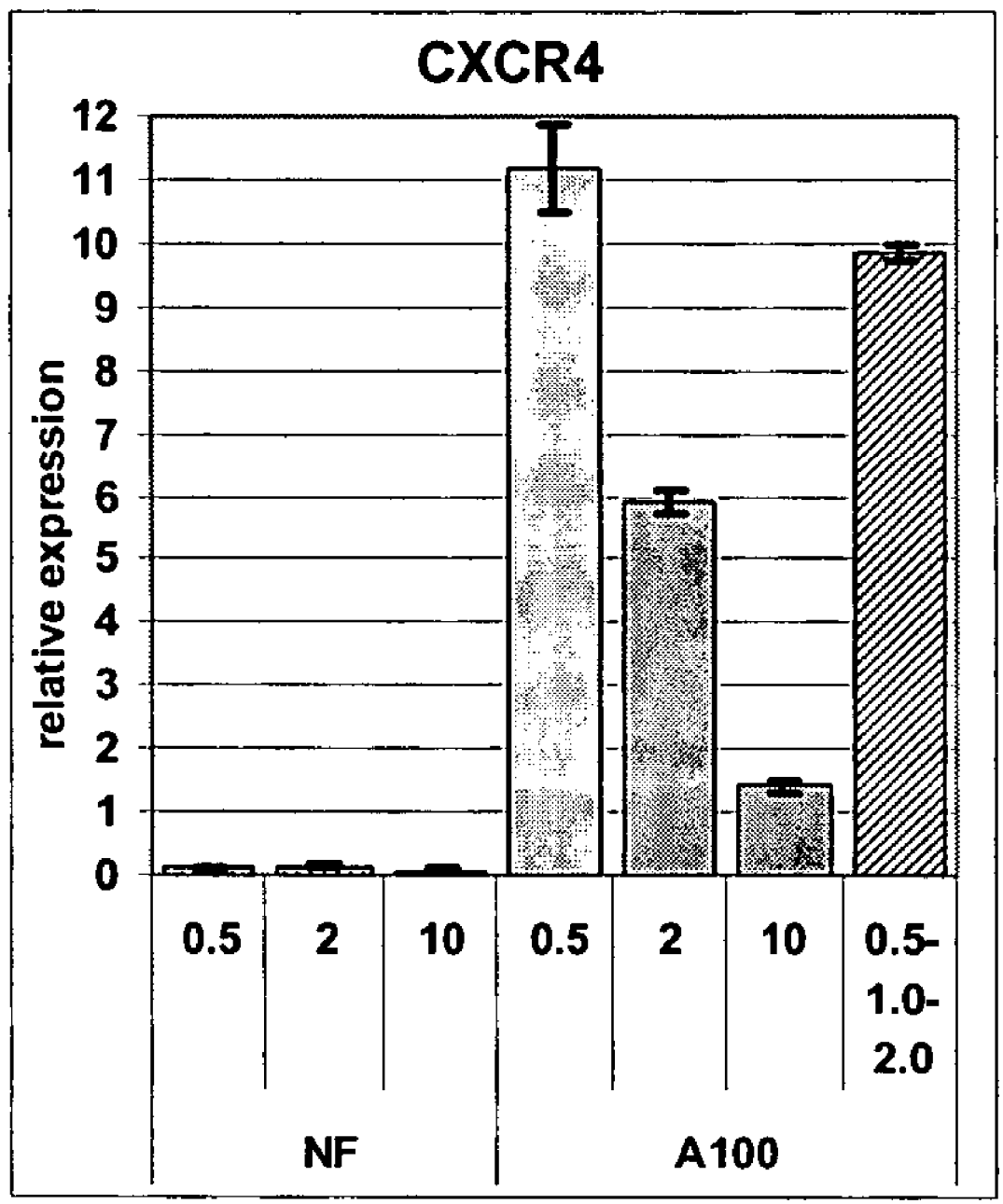
FIG. 26 is a bar chart showing the relative expression level of CXCR4 in differentiating hESCs under various media conditions.
Figure 27:
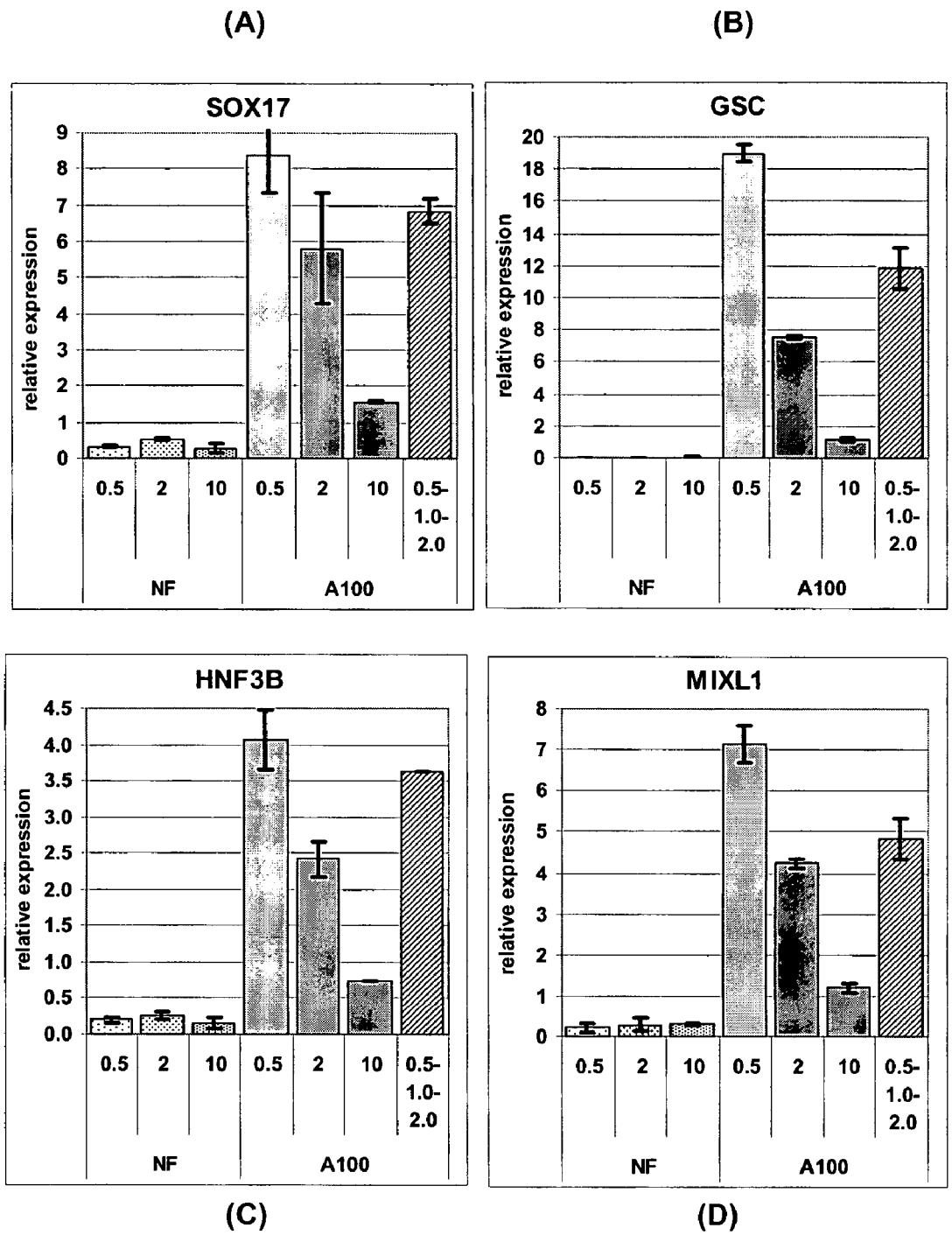
FIGS. 27A-D are bar charts that show how a panel of definitive endoderm markers share a very similar pattern of expression to CXCR4 across the same differentiation treatments displayed in FIG. 26.

The expression levels of CXCR4 varied dramatically across the 7 culture conditions used (FIG. 26). In general, CXCR4 expression was high in activin A treated cultures (A100) and low in those which did not receive exogenous activin A (NF). In addition, among the A100 treated cultures, CXCR4 expression was highest when FBS concentration was lowest. There was a remarkable decrease in CXCR4 level in the 10% FBS condition such that the relative expression was more in line with the conditions that did not receive activin A (NF).

As described above, expression of the SOX17, GSC, MIXL1, and HNF3β genes is consistent with the characterization of a cell as definitive endoderm. The relative expression of these four genes across the 7 differentiation conditions mirrors that of CXCR4 (FIGS. 27A-D). This demonstrates that CXCR4 is also a marker of definitive endoderm.

Ectoderm and mesoderm lineages can be distinguished from definitive endoderm by their expression of various markers. Early mesoderm expresses the genes Brachyury and MOX1 while nascent neuro-ectoderm expresses SOX1 and ZIC1. FIGS. 28A-D demonstrate that the cultures which did not receive exogenous activin A were preferentially enriched for mesoderm and ectoderm gene expression and that among the activin A treated cultures, the 10% FBS condition also had increased levels of mesoderm and ectoderm marker expression. These patterns of expression were inverse to that of CXCR4 and indicated that CXCR4 was not highly expressed in mesoderm or ectoderm derived from hESCs at this developmental time period.

Figure 28:
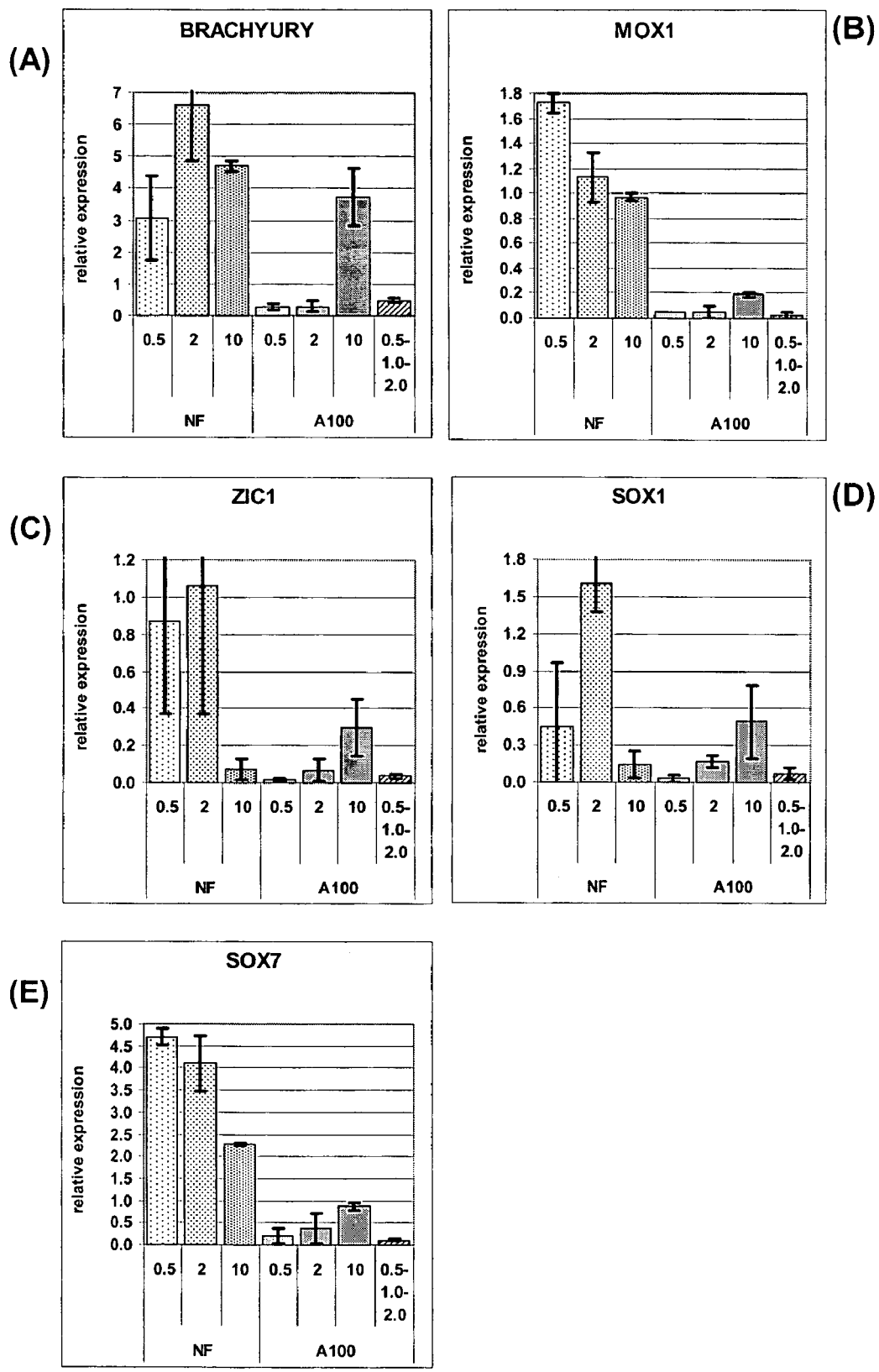
FIGS. 28A-E are bar charts showing how markers for mesoderm (BRACHYURY, MOX1), ectoderm (SOX1, ZIC1) and visceral endoderm (SOX7) exhibit an inverse relationship to CXCR4 expression across the same treatments displayed in FIG. 26.

Early during mammalian development, differentiation to extra-embryonic lineages also occurs. Of particular relevance here is the differentiation of visceral endoderm that shares the expression of many genes in common with definitive endoderm, including SOX17. To distinguish definitive endoderm from extra-embryonic visceral endoderm one should examine a marker that is distinct between these two. SOX7 represents a marker that is expressed in the visceral endoderm but not in the definitive endoderm lineage. Thus, culture conditions that exhibit robust SOX17 gene expression in the absence of SOX7 expression are likely to contain definitive and not visceral endoderm. It is shown in FIG. 28E that SOX7 was highly expressed in cultures that did not receive activin A, SOX7 also exhibited increased expression even in the presence of activin A when FBS was included at 10%. This pattern is the inverse of the CXCR4 expression pattern and suggests that CXCR4 is not highly expressed in visceral endoderm.

Figure 29:
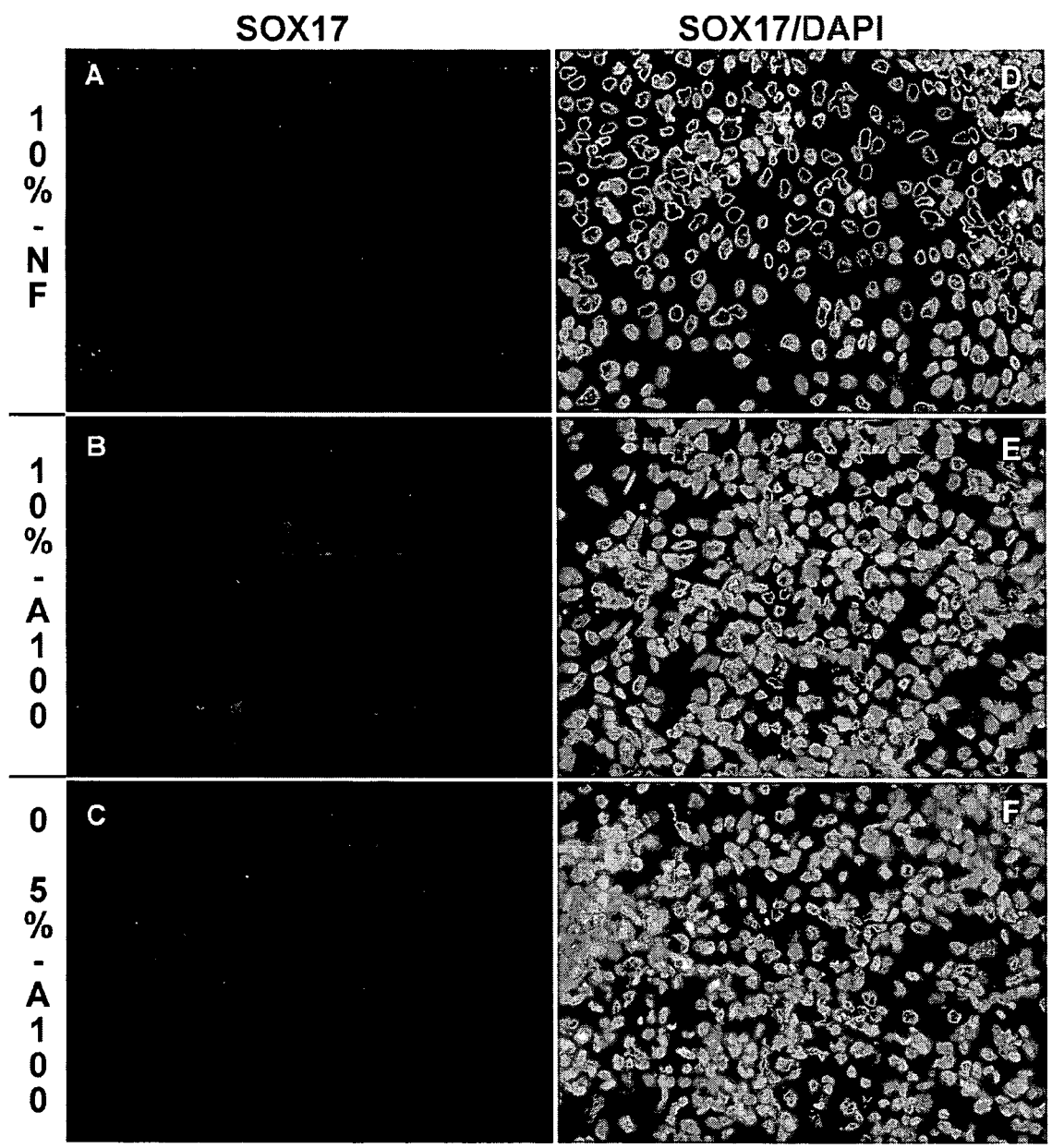
FIGS. 29A-F are micrographs that show the relative difference in SOX17 immunoreactive cells across three of the media conditions displayed in FIGS. 26-28.

The relative number of SOX17 immunoreactive (SOX17$^+$) cells present in each of the differentiation conditions mentioned above was also determined. When hESCs were differentiated in the presence of high dose activin A and low FBS concentration (0.5%-2.0%) SOX17$^+$ cells were ubiquitously distributed throughout the culture. When high dose activin A was used but FBS was included at 10% (v/v), the SOX17$^+$ cells appeared at much lower frequency and always appeared in isolated clusters rather than evenly distributed throughout the culture (FIGS. 29A and C as well as B and E). A further decrease in SOX17$^+$ cells was seen when no exogenous activin A was used. Under these conditions the SOX17$^+$ cells also appeared in clusters and these clusters were smaller and much more rare than those found in the high activin A, low FBS treatment (FIG. 29 C and F). These results demonstrate that the CXCR4 expression patterns not only correspond to definitive endoderm gene expression but also to the number of definitive endoderm cells in each condition.

Example 8

Differentiation Conditions that Enrich for Definitive Endoderm Increase the Proportion of CXCR4 Positive Cells The dose of activin A also effects the efficiency at which definitive endoderm can be derived from hESCs. This example demonstrates that increasing the dose of activin A increases the proportion of CXCR4$^+$ cells in the culture.

hESCs were differentiated in RPMI media supplemented with 0.5%-2% FBS (increased from 0.5% to 1.0% to 2.0% over the first 3 days of differentiation) and either 0, 10, or 100 ng/ml of activin A. After 7 days of differentiation the cells were dissociated in PBS without $Ca^{2+}/Mg^{2+}$ containing 2% FBS and 2 mM (EDTA) for 5 minutes at room temperature. The cells were filtered through 35 μm nylon filters, counted and pelleted. Pellets were resuspended in a small volume of 50% human serum/50% normal donkey serum and incubated for 2 minutes on ice to block non-specific antibody binding sites. To this, 1 μl of mouse anti-CXCR4 antibody (Abcam, cat# ab10403-100) was added per 50 μl (containing approximately $10^5$ cells) and labeling proceeded for 45 minutes on ice. Cells were washed by adding 5 ml of PBS containing 2% human serum (buffer) and pelleted. A second wash with 5 ml of buffer was completed then cells were resuspended in 50 μl buffer per $10^5$ cells. Secondary antibody (FITC conjugated donkey anti-mouse; Jackson ImmunoResearch, cat# 715-096-151) was added at 5 μg/ml final concentration and allowed to label for 30 minutes followed by two washes in buffer as above. Cells were resuspended at $5 \times 10^6$ cells/ml in buffer and analyzed and sorted using a FACS Vantage (Beckton Dickenson) by the staff at the flow cytometry core facility (The Scripps Research Institute). Cells were collected directly into RLT lysis buffer (Qiagen) for subsequent isolation of total RNA for gene expression analysis by real-time quantitative PCR.

Figure 30:
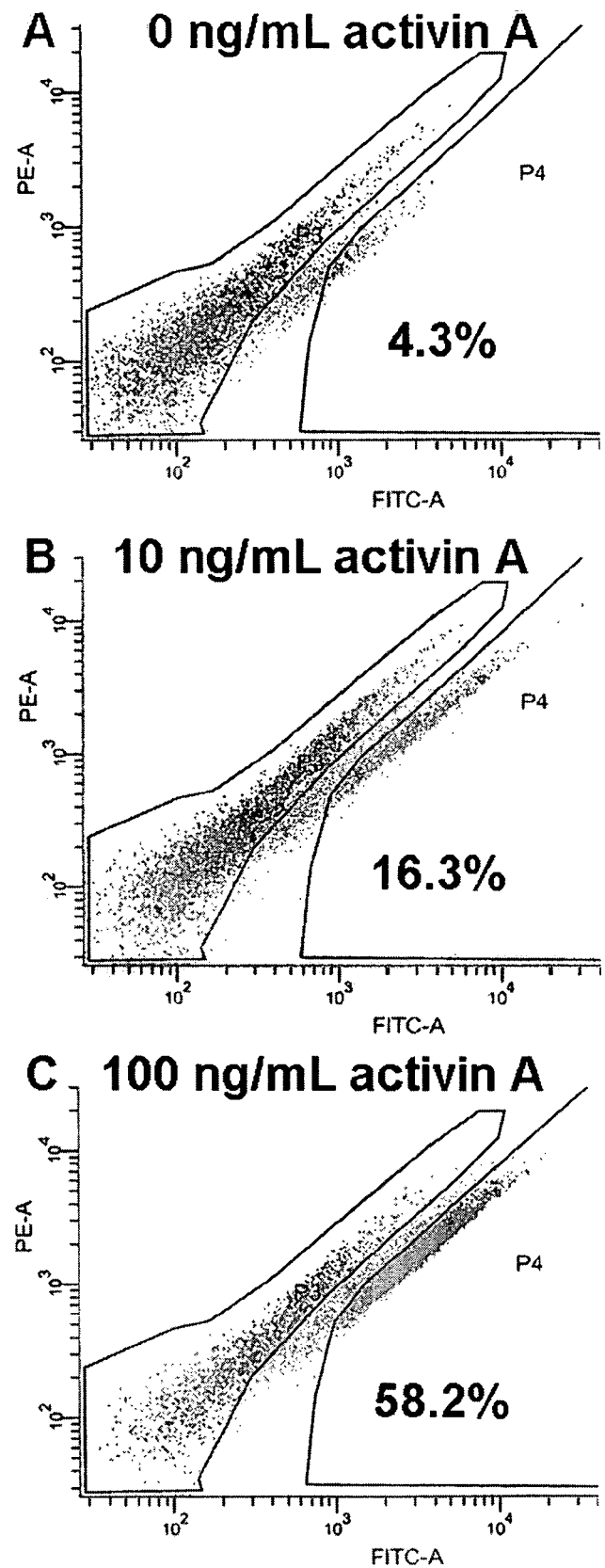
FIGS. 30A-C are flow cytometry dot plots that demonstrate the increase in CXCR4+ cell number with increasing concentration of activin A added to the differentiation media.
Figure 31:
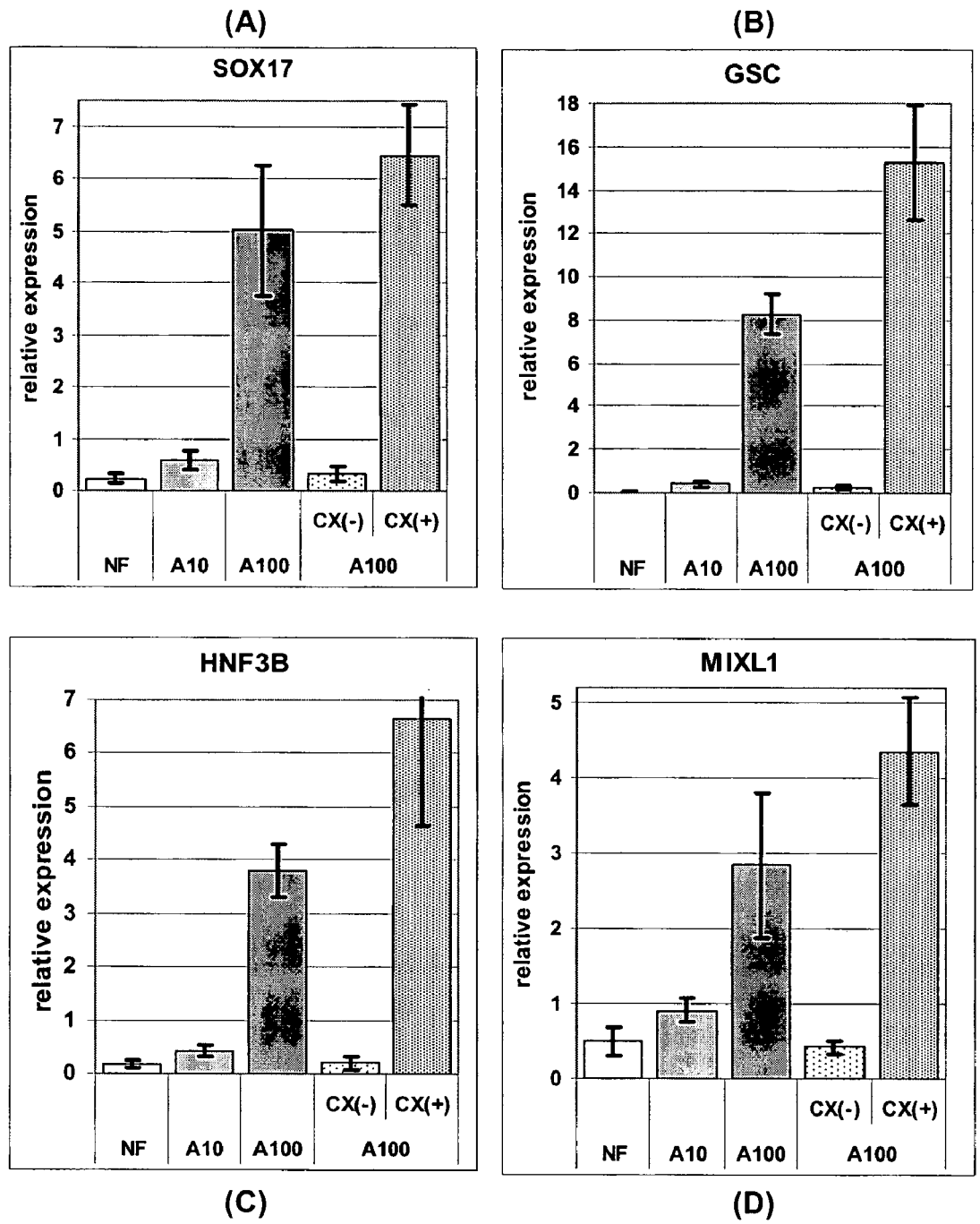
FIGS. 31A-D are bar charts that show the CXCR4+ cells isolated from the high dose activin A treatment (A100-CX+) are even further enriched for definitive endoderm markers than the parent population (A100).

The number of CXCR4+ cells as determined by flow cytometry were observed to increase dramatically as the dose of activin A was increased in the differentiation culture media (FIGS. 30A-C). The CXCR4+ cells were those falling within the R4 gate and this gate was set using a secondary antibody-only control for which 0.2% of events were located in the R4 gate. The dramatically increased numbers of CXCR4+ cells correlates with a robust increase in definitive endoderm gene expression as activin A dose is increased (FIGS. 31A-D).

Example 9

Isolation of CXCR4 Positive Cells Enriches for Definitive Endoderm Gene Expression and Depletes Cells Expressing Markers of Mesoderm, Ectoderm and Visceral Endoderm The CXCR4+ and CXCR4− cells identified in Example 8 above were collected and analyzed for relative gene expression and the gene expression of the parent populations was determined simultaneously.

Figure 32:
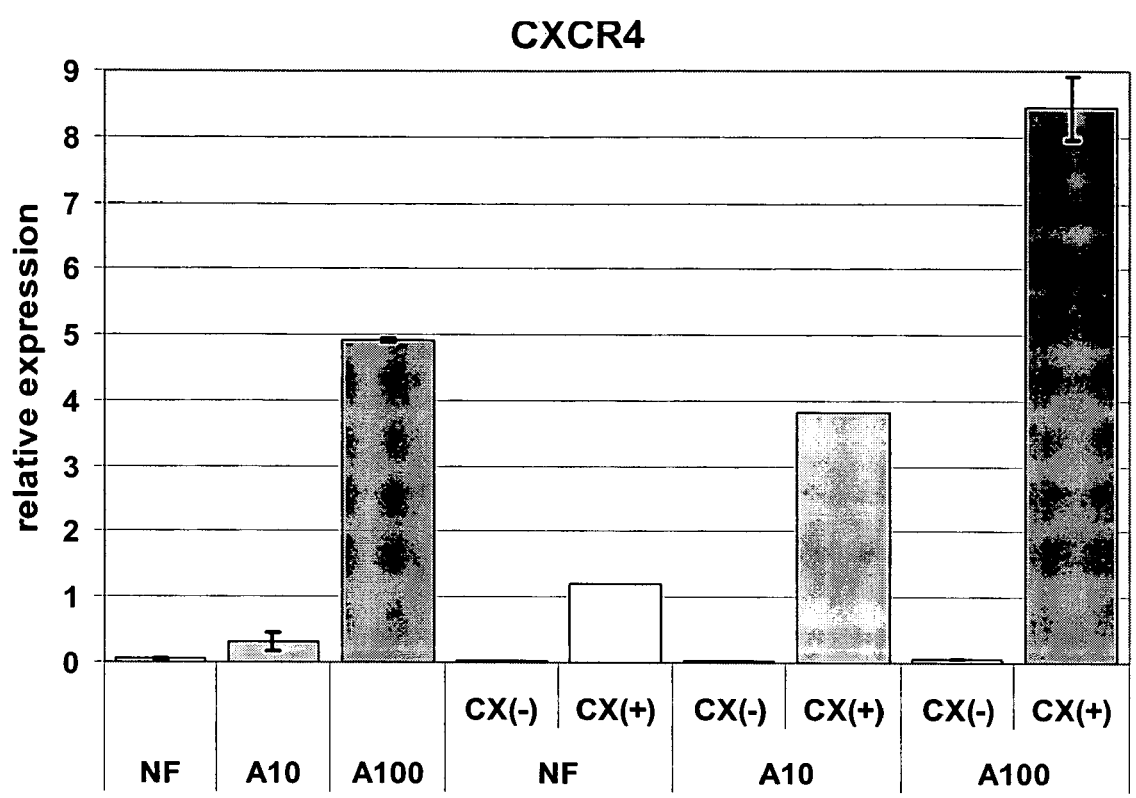
FIG. 32 is a bar chart showing gene expression from CXCR4+ and CXCR4− cells isolated using fluorescence-activated cell sorting (FACS) as well as gene expression in the parent populations. This demonstrates that the CXCR4+ cells contain essentially all the CXCR4 gene expression present in each parent population and the CXCR4− populations contain very little or no CXCR4 gene expression.
Figure 33:
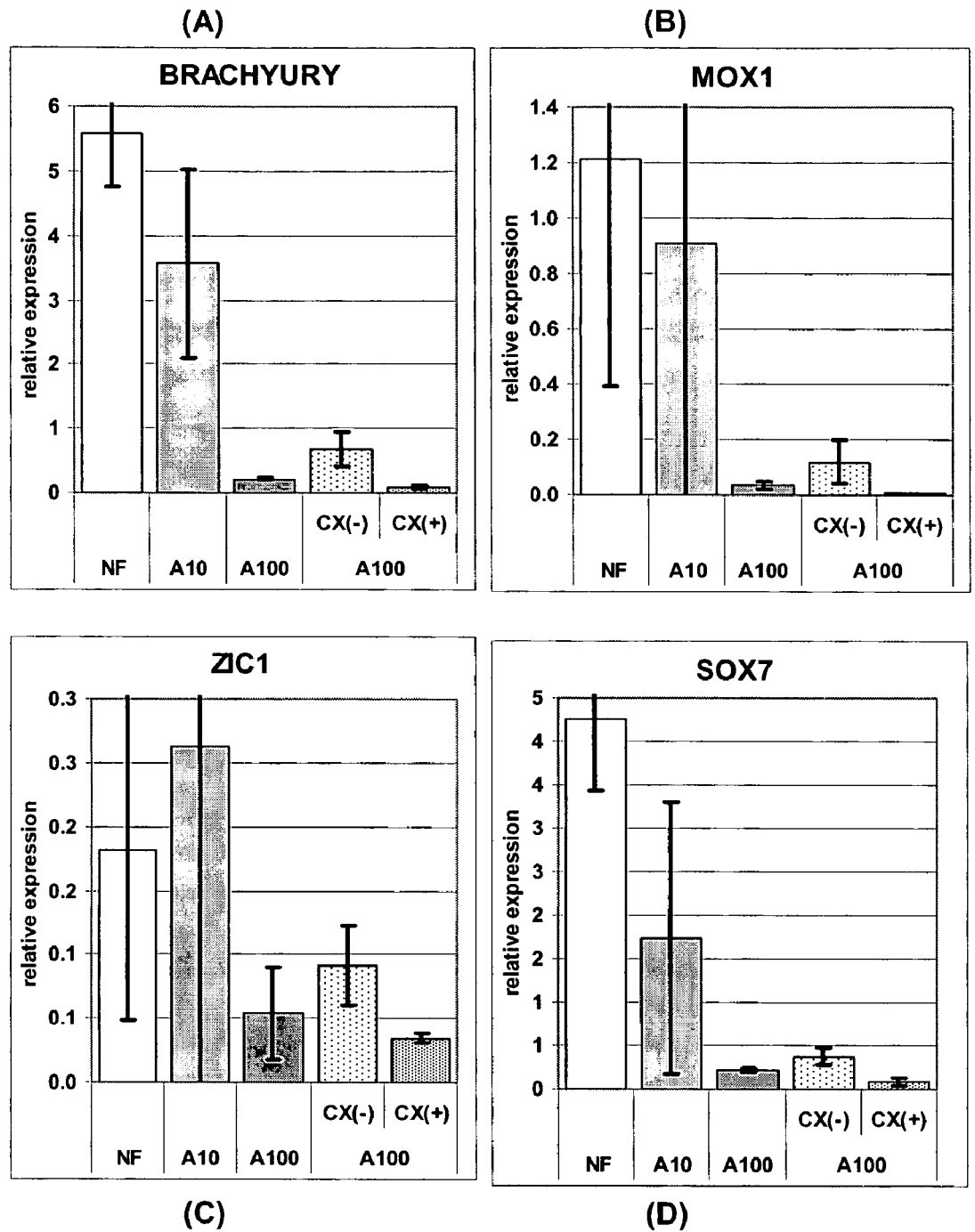
FIGS. 33A-D are bar charts that demonstrate the depletion of mesoderm (BRACHYURY, MOX1), ectoderm (ZIC1) and visceral endoderm (SOX7) gene expression in the CXCR4+ cells isolated from the high dose activin A treatment which is already suppressed in expression of these non-definitive endoderm markers.

The relative levels of CXCR4 gene expression was dramatically increased with increasing dose of activin A (FIG. 32). This correlated very well with the activin A dose-dependent increase of CXCR4+ cells (FIGS. 30A-C). It is also clear that isolation of the CXCR4+ cells from each population accounted for nearly all of the CXCR4 gene expression in that population. This demonstrates the efficiency of the FACS method for collecting these cells.

Gene expression analysis revealed that the CXCR4+ cells contain not only the majority of the CXCR4 gene expression, but they also contained gene expression for other markers of definitive endoderm. As shown in FIGS. 31A-D, the CXCR4+ cells were further enriched over the parent A100 population for SOX17, GSC, HNF3B, and MIXL1. In addition, the CXCR4− fraction contained very little gene expression for these definitive endoderm markers. Moreover, the CXCR4+ and CXCR4− populations displayed the inverse pattern of gene expression for markers of mesoderm, ectoderm and extra-embryonic endoderm. FIGS. 33A-D shows that the CXCR4+ cells were depleted for gene expression of Brachyury, MOX1, ZIC1, and SOX7 relative to the A100 parent population. This A100 parent population was already low in expression of these markers relative to the low dose or no activin A conditions. These results show that the isolation of CXCR4+ cells from hESCs differentiated in the presence of high activin A yields a population that is highly enriched for and substantially pure definitive endoderm.

Example 10

Quantitation of Definitive Endoderm Cells in a Cell Population Using CXCR4

To confirm the quantitation of the proportion of definitive endoderm cells present in a cell culture or cell population as determined previously herein and as determined in U.S. Provisional Patent Application No. 60/532,004, entitled DEFINITIVE ENDODERM, filed Dec. 23, 2003, the disclosure of which is incorporated herein by reference in its entirety, cells expressing CXCR4 and other markers of definitive endoderm were analyzed by FACS.

Using the methods such as those described in the above Examples, hESCs were differentiated to produce definitive endoderm. In particular, to increase the yield and purity in differentiating cell cultures, the serum concentration of the medium was controlled as follows: 0.2% FBS on day 1, 1.0% FBS on day 2 and 2.0% FBS on days 3-6. Differentiated cultures were sorted by FACS using three cell surface epitopes, E-Cadherin, CXCR4, and Thrombomodulin. Sorted cell populations were then analyzed by Q-PCR to determine relative expression levels of markers for definitive and extraembryonic-endoderm as well as other cell types. CXCR4 sorted cells taken from optimally differentiated cultures resulted in the isolation of definitive endoderm cells that were >98% pure.

Table 2 shows the results of a marker analysis for a definitive endoderm culture that was differentiated from hESCs using the methods described herein.

TABLE 2

| | Composition of Definitive Endoderm Cultures | | | |
|---|---|---|---|---|
| Marker(s) | Percent of culture | Percent Definitive Endoderm | Percent Extraembryonic endoderm | Percent hES cells |
| SOX17 | 70-80 | 100 | | |
| Thrombomodulin | <2 | 0 | 75 | |
| AFP | <1 | 0 | 25 | |
| CXCR4 | 70-80 | 100 | 0 | |
| ECAD | 10 | 0 | | 100 |
| other (ECAD neg.) | 10-20 | | | |
| Total | 100 | 100 | 100 | 100 |

In particular, Table 2 indicates that CXCR4 and SOX17 positive cells (endoderm) comprised from 70%-80% of the cells in the cell culture. Of these SOX17-expressing cells, less than 2% expressed TM (parietal endoderm) and less than 1% expressed AFP (visceral endoderm). After subtracting the proportion of TM-positive and AFP-positive cells (combined parietal and visceral endoderm; 3% total) from the proportion of SOX17/CXCR4 positive cells, it can be seen that about 67% to about 77% of the cell culture was definitive endoderm. Approximately 10% of the cells were positive for E-Cadherin (ECAD), which is a marker for hESCs, and about 10-20% of the cells were of other cell types.

We have discovered that the purity of definitive endoderm in the differentiating cell cultures that are obtained prior to FACS separation can be improved as compared to the above-described low serum procedure by maintaining the FBS concentration at ≦0.5% throughout the 5-6 day differentiation procedure. However, maintaining the cell culture at ≦0.5% throughout the 5-6 day differentiation procedure also results in a reduced number of total definitive endoderm cells that are produced.

Definitive endoderm cells produced by methods described herein have been maintained and expanded in culture in the presence of activin for greater than 50 days without appreciable differentiation. In such cases, SOX17, CXCR4, MIXL1, GATA4, HNF3β expression is maintained over the culture period. Additionally, TM, SPARC, OCT4, AFP, SOX7, ZIC1 and BRACH were not detected in these cultures.

It is likely that such cells can be maintained and expanded in culture for substantially longer than 50 days without appreciable differentiation.

Example 11

Additional Marker of Definitive Endoderm Cells

In the following experiment, RNA was isolated from purified definitive endoderm and human embryonic stem cell populations. Gene expression was then analyzed by gene chip analysis of the RNA from each purified population. Q-PCR was also performed to further investigate the potential of genes expressed in definitive endoderm, but not in embryonic stem cells, as a marker for definitive endoderm.

Human embryonic stem cells (hESCs) were maintained in DMEM/F12 media supplemented with 20% KnockOut Serum Replacement, 4 ng/ml recombinant human basic fibroblast growth factor (bFGF), 0.1 mM 2-mercaptoethanol, L-glutamine, non-essential amino acids and penicillin/streptomycin. hESCs were differentiated to definitive endoderm by culturing for 5 days in RPMI media supplemented with 100 ng/ml of recombinant human activin A, fetal bovine serum (FBS), and penicillin/streptomycin. The concentration of FBS was varied each day as follows: 0.1% (first day), 0.2% (second day), 2% (days 3-5).

Cells were isolated by fluorescence activated cell sorting (FACS) in order to obtain purified populations of hESCs and definitive endoderm for gene expression analysis. Immunopurification was achieved for hESCs using SSEA4 antigen (R&D Systems, cat# FAB1435P) and for definitive endoderm using CXCR4 (R&D Systems, cat# FAB170P). Cells were dissociated using trypsin/EDTA (Invitrogen, cat# 25300-054), washed in phosphate buffered saline (PBS) containing 2% human serum and resuspended in 100% human serum on ice for 10 minutes to block non-specific binding. Staining was carried out for 30 minutes on ice by adding 200 μl of phycoerythrin-conjugated antibody to $5\times10^6$ cells in 800 μl human serum. Cells were washed twice with 8 ml of PBS buffer and resuspended in 1 ml of the same. FACS isolation was carried out by the core facility of The Scripps Research Institute using a FACS Vantage (BD Biosciences). Cells were collected directly into RLT lysis buffer and RNA was isolated by RNeasy according to the manufacturers instructions (Qiagen).

Purified RNA was submitted in duplicate to Expression Analysis (Durham, N.C.) for generation of the expression profile data using the Affymetrix platform and U133 Plus 2.0 high-density oligonucleotide arrays. Data presented is a group comparison that identifies genes differentially expressed between the two populations, hESCs and definitive endoderm. Genes that exhibited a robust upward change in expression level over that found in hESCs were selected as new candidate markers that are highly characteristic of definitive endoderm. Select genes were assayed by Q-PCR, as described above, to verify the gene expression changes found on the gene chip and also to investigate the expression pattern of these genes during a time course of hESC differentiation.

Figure 34:
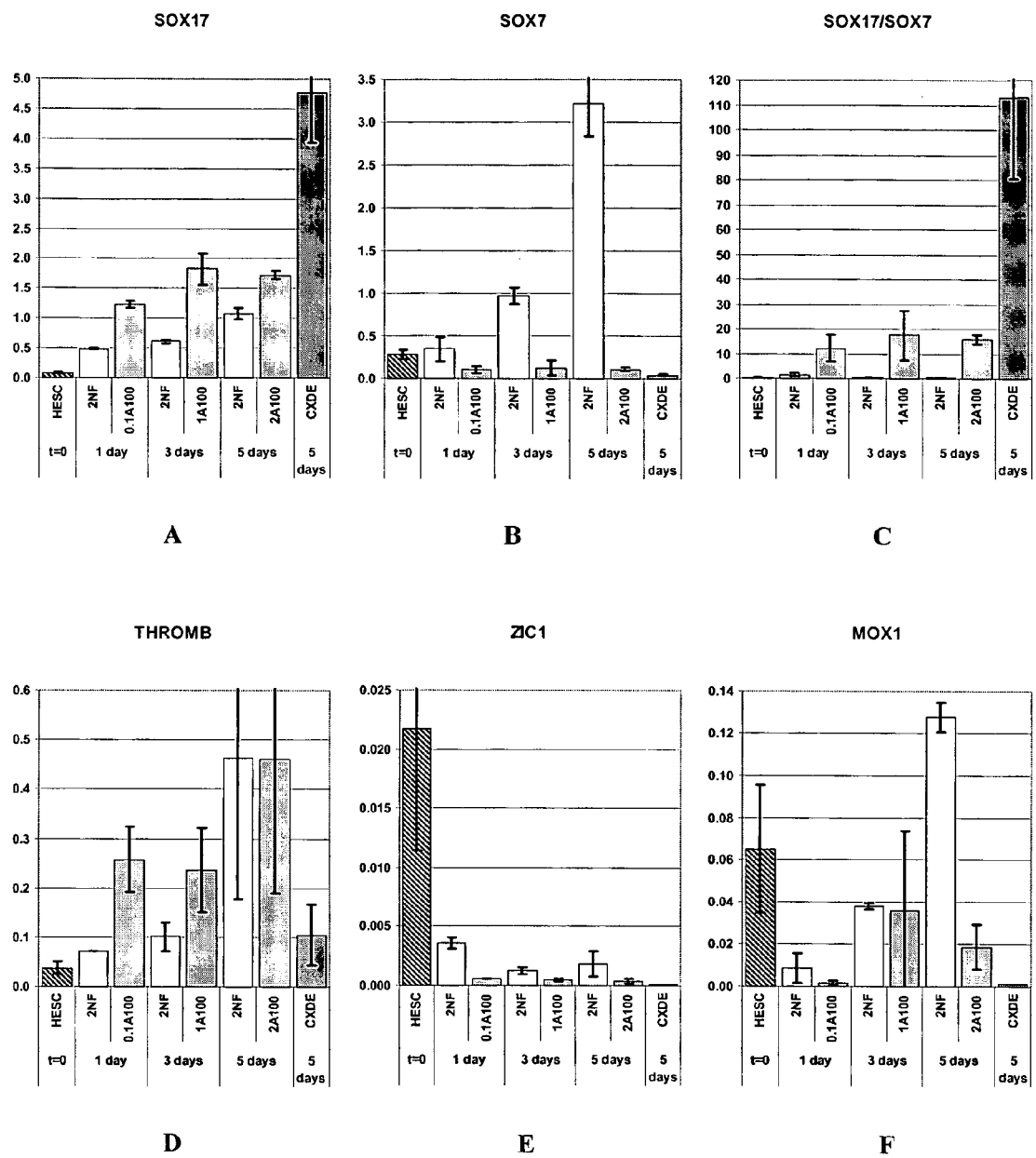
FIGS. 34A-M are bar charts showing the expression patterns of marker genes that can be used to identify definitive endoderm cells. The expression analysis of definitive endoderm markers, FGF17, VWF, CALCR, FOXQ1, CMKOR1 and CRIP1 is shown in panels G-L, respectively. The expression analysis of previously described lineage marking genes, SOX17, SOX7, SOX17/SOX7, TM, ZIC1, and MOX1 is shown in panels A-F, respectively. Panel M shows the expression analysis of CXCR4. With respect to each of panels A-M, the column labeled hESC indicates gene expression from purified human embryonic stem cells; 2NF indicates cells treated with 2% FBS, no activin addition; 0.1A100 indicates cells treated with 0.1% FBS, 100 ng/ml activin A; 1A100 indicates cells treated with 1% FBS, 100 ng/ml activin A; and 2A100 indicates cells treated with 2% FBS, 100 ng/ml activin A.
Figure 34:
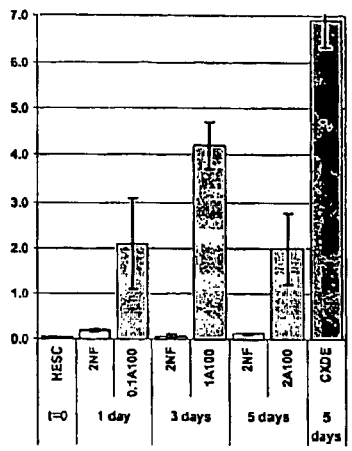
Figure 34:
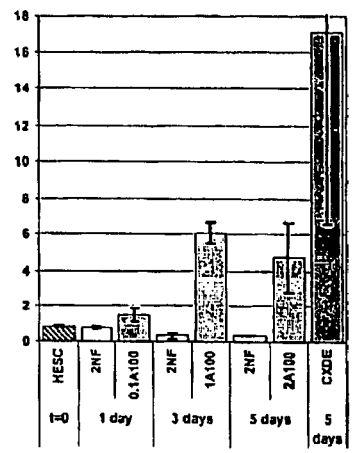
Figure 34:
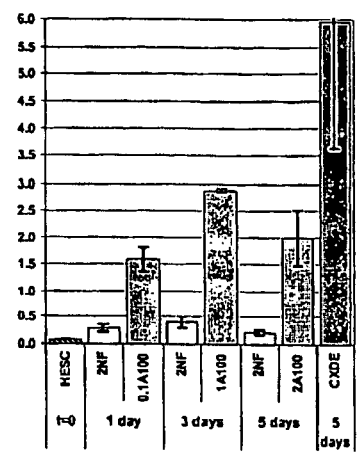
Figure 34:
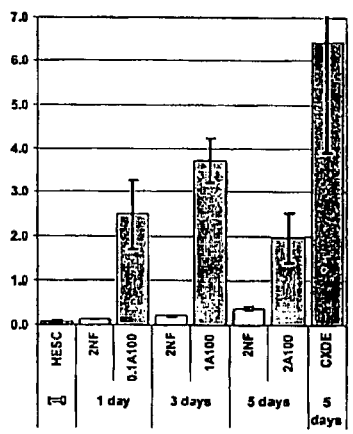
Figure 34:
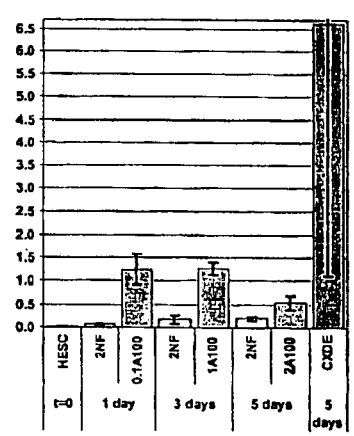
Figure 34:
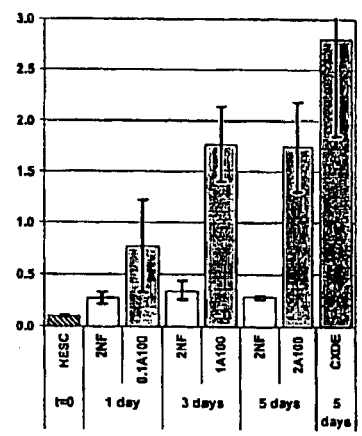
Figure 34:
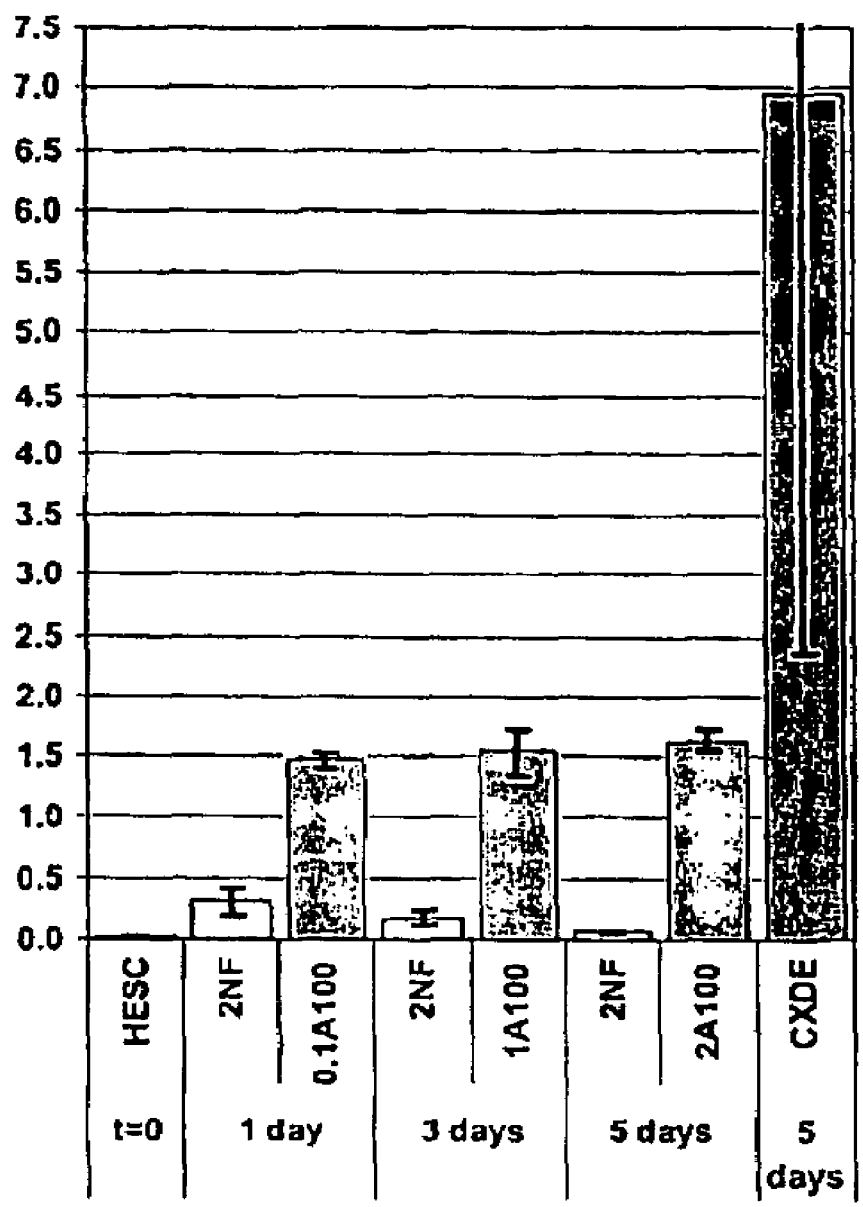
Figure 35:
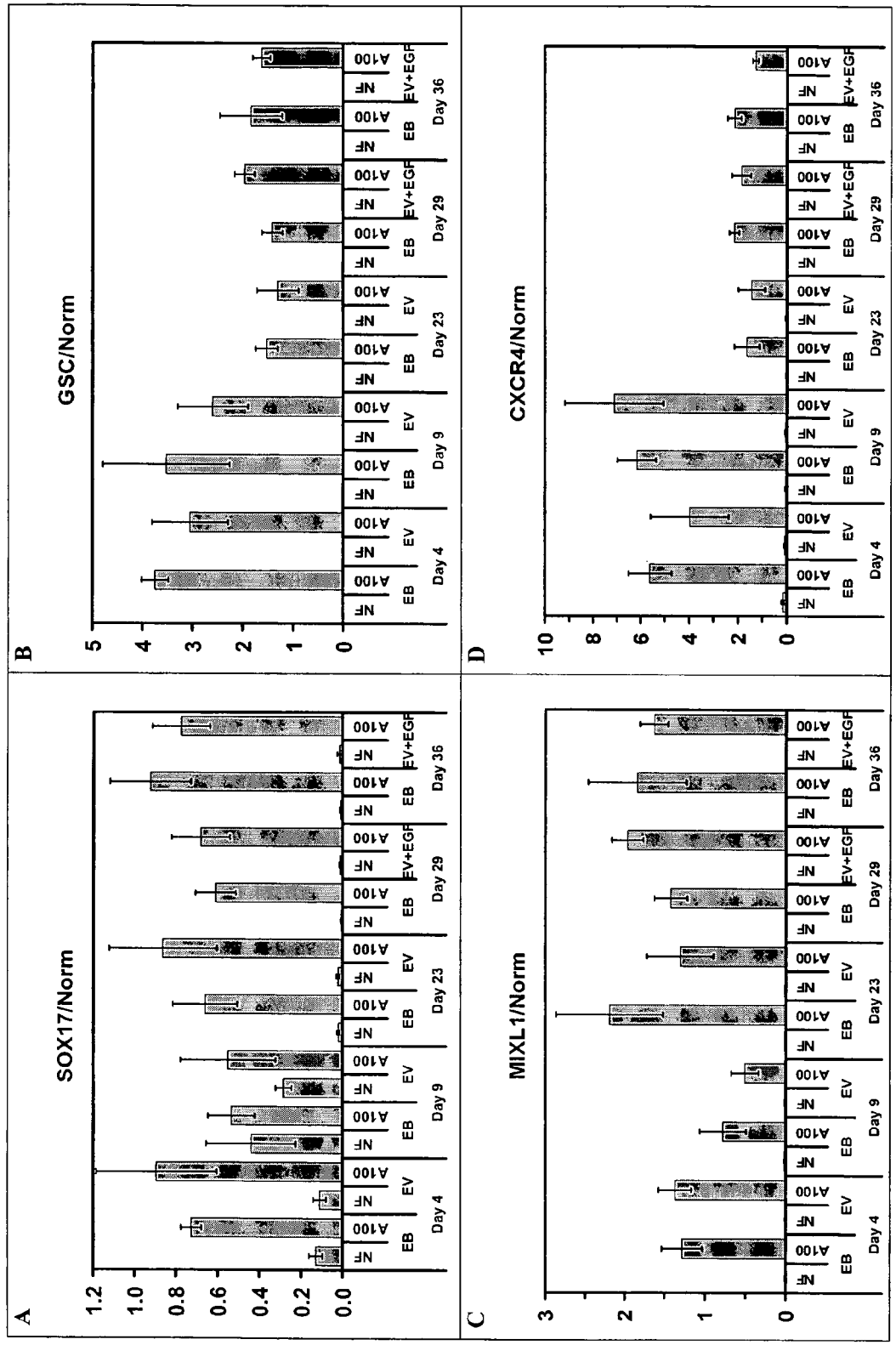
FIGS. 35A-D are bar charts showing the expression patterns of definitive endoderm marker genes in cell cultures maintained for 36 days under various growth conditions. The expression analysis of definitive endoderm markers SOX17, GSC, MIXL1 and CXCR4 is shown in panels A-D, respectively. EB and EV are used to designate to separate cell populations each from the hCyT25 hESC line. The abbreviation NF indicates cells grown in the absence of activin A, whereas A100 indicates cells grown in the presence of 100 ng/ml this factor. EGF indicates 50 ng/ml epidermal growth factor.

FIGS. 34A-M show the gene expression results for certain markers. Results are displayed for cell cultures analyzed 1, 3 and 5 days after the addition of 100 ng/ml activin A, CXCR4-expressing definitive endoderm cells purified at the end of the five day differentiation procedure (CXDE), and in purified hESCs. A comparison of FIGS. 34C and G-M demonstrates that the six marker genes, FGF17, VWF, CALCR, FOXQ1, CMKOR1 and CRIP1, exhibit an expression pattern that is almost identical to each other and which is also identical to the pattern of expression of CXCR4 and the ratio of SOX17/SOX7. As described previously, SOX17 is expressed in both the definitive endoderm as well as in the SOX7-expressing extra-embryonic endoderm. Since SOX7 is not expressed in the definitive endoderm, the ratio of SOX17/SOX7 provides a reliable estimate of definitive endoderm contribution to the SOX17 expression witnessed in the population as a whole. The similarity of panels G-L and M to panel C indicates that FGF17, VWF, CALCR, FOXQ1, CMKOR1 and CRIP1 are likely markers of definitive endoderm and that they are not significantly expressed in extra-embryonic endoderm cells.

It will be appreciated that the Q-PCR results described herein can be further confirmed by ICC.

Example 12

Generation of SOX17 Promoter-EGFP Transgenic hESC Lines and CXCR4 Promoter-EGFP Transgenic hESC Lines As an alternative to purification of definitive endoderm using the CXCR4-specific antibody, EGFP fusions to either the SOX17 or the CXCR4 promoters can be used. In particular, this Example describes the construction of a vector comprising a reporter cassette which comprises a reporter gene under the control of the SOX17 regulatory region. Additionally, the construction of a vector comprising a reporter cassette which comprises a reporter gene under the control of the CXCR4 regulatory region is described. This Example also describes the preparation of a cell, such as a human embryonic stem cell, transfected with one or more of these vectors as well as a cell having this one or both of these reporter cassettes integrated into its genome.

SOX17-expressing definitive endoderm cell lines and CXRC4-expressing definitive endoderm cell lines genetically tagged with a reporter gene are constructed by placing a GFP reporter gene under the control of the regulatory region (promoter) of the SOX17 gene or the CXCR4 gene, respectively. First, a plasmid construct in which EGFP expression is driven by the human SOX17 or CXCR4 gene promoter is generated by replacing the CMV promoter of vector pEGFP-N1 (Clontech) with the human SOX17 or CXCR4 control region. These control regions contain the characterized regulatory elements of either the SOX17 or the CXCR4 gene, and they is sufficient to confer the normal expression pattern of these genes in transgenic mice. In the resulting vector, expression of EFGP is driven by either the SOX17 promoter or the CXCR4 promoter. In some experiments, this vector can be transfected into hESCs.

The SOX17 promoter/EGFP cassette or the CXCR4 promoter/EGFP cassette is excised from the above vector, and then subcloned into a selection vector containing the neomycin phosphotransferase gene under control of the phosphoglycerate kinase-1 promoter. The selection cassette is flanked by flp recombinase recognition sites to allow removal of the cassette. This selection vector is linearized, and then introduced into hESCs using standard lipofection methods. Following 10-14 days of selection in G418, undifferentiated transgenic hESC clones is isolated and expanded.

It will be appreciated that reporter genes other than GFP or EGFP can be used in any of the above-described constructs provided that the reporter allows for cell separation by FACS.

Example 13

Alternative Isolation of Definitive Endoderm

The following Example demonstrates that hESCs comprising a SOX17 or CXCR4 promoter/EGFP cassette can be differentiated into definitive endoderm cells and then subsequently isolated by fluorescence-activated cell sorting (FACS).

SOX17 or CXCR4 promoter/EGFP transgenic hESCs are differentiated for approximately 6, 12 and 18 hours in growth medium containing 100 ng/ml activin A and no serum. The differentiated cells are then harvested by trypsin digestion and sorted on a Becton Dickinson FACS Diva directly into RNA lysis buffer or PBS. A sample of single live cells is taken without gating for EGFP and single live cells are gated into EGFP positive and GFP negative populations. In a separate experiment, the EGFP positive fraction is separated into two equally sized populations according to fluorescence intensity (Hi and Lo).

Following sorting, cell populations are analyzed by both Q-PCR and immunocytochemistry. For Q-PCR analysis, RNA is prepared using Qiagen RNeasy columns and then converted to cDNA. Q-PCR is conducted as described previously. For immunocytochemistry analysis, cells are sorted into PBS, fixed for 10 minutes in 4% paraformaldehyde, and adhered to glass slides using a Cytospin centrifuge. The primary antibody SOX17 or CXCR4. An appropriate secondary antibody conjugated to FITC (green) or Rhodamine (Red) is used to detect binding of the primary antibody.

Sorted cells are further subjected to Q-PCR analysis. Differentiated cells show a correlation of EGFP fluorescence with endogenous SOX17 or CXCR4 expression gene expression. Compared to non-fluorescing cells, the EGFP positive cells show a greater than 2-fold increase in SOX17 or CXCR4 expression levels. The separation of high and low EGFP intensity cells indicates that EGFP expression level correlates with SOX17 or CXCR4 expression level. In addition to SOX17 or CXCR4 mRNA analysis, sorted cells are subjected to immunocytochemistry analysis of SOX17 or CXCR4 polypeptide (in embodiments where CXCR4/EGFP fusions are used, SOX17 polypeptide expression is analyzed and in cases where SOX17/EGFP fusions are used, CXCR4 polypeptide expression is analyzed). Substantial expression of either the SOX17 or CXCR4 polypeptides can be seen in the enriched in the EGFP positive fraction. In contrast, little expression of either the SOX17 or CXCR4 polypeptides is seen in the EGFP negative fraction.

Given these results, at least about 5% of the cells present in the differentiated cell cultures prior to sorting are SOX17/CXCR4-positive definitive endoderm cells. At least about 90% of the cells in the sorted cell populations are SOX17/CXCR4-positive definitive endoderm cells.

Example 14

Passage of Definitive Endoderm Cells in Culture

This Example demonstrates that the definitive endoderm cells described herein can be maintained in cell culture and passaged without further differentiation.

Definitive endoderm cells were differentiated from two related passages, designated EB and EV, of the CyT25 hESC line in the presence of 100 ng/ml activin A in low serum RMPI. The low serum RPMI contained 0% (v/v) fetal bovine serum (FBS) on day 1, 0.2% (v/v) FBS on day two and 2% serum on each day thereafter. After four days of differentiation, the cells maintained in culture in either the presence or absence of 100 ng/ml activin A for a total of 36 days as measured from induction of differentiation. During the 36 day culture period, the definitive endoderm cells were passaged twice. Furthermore, on days 29-36 the cells of the group designated EV were additionally contacted with 50 mg/ml EGF. On days 4, 9, 23, 29 and 36 of culture, Q-PCR was used to measure the expression of marker genes indicative of definitive endoderm.

FIGS. 35A-D show that, in cell cultures provided with 100 ng/ml activin A, expression of the definitive endoderm markers SOX17, GSC, MIXL1 and CXCR4 was maintained during the 32 day culture period subsequent to the derivation of the definitive endoderm cells from hESCs (days 4 to 36). Little expression of these markers was observed in the cell cultures grown in the absence of activin A. Addition of 50 ng/ml EGF did not appear to significantly increase the expression of any of the definitive endoderm markers.

Example 15

Expansion of Purified Definitive Endoderm Cells

This Example demonstrates that the definitive endoderm cells described herein can be differentiated from hESCs, purified and then regrown and expanded in cell culture.

Figure 36:
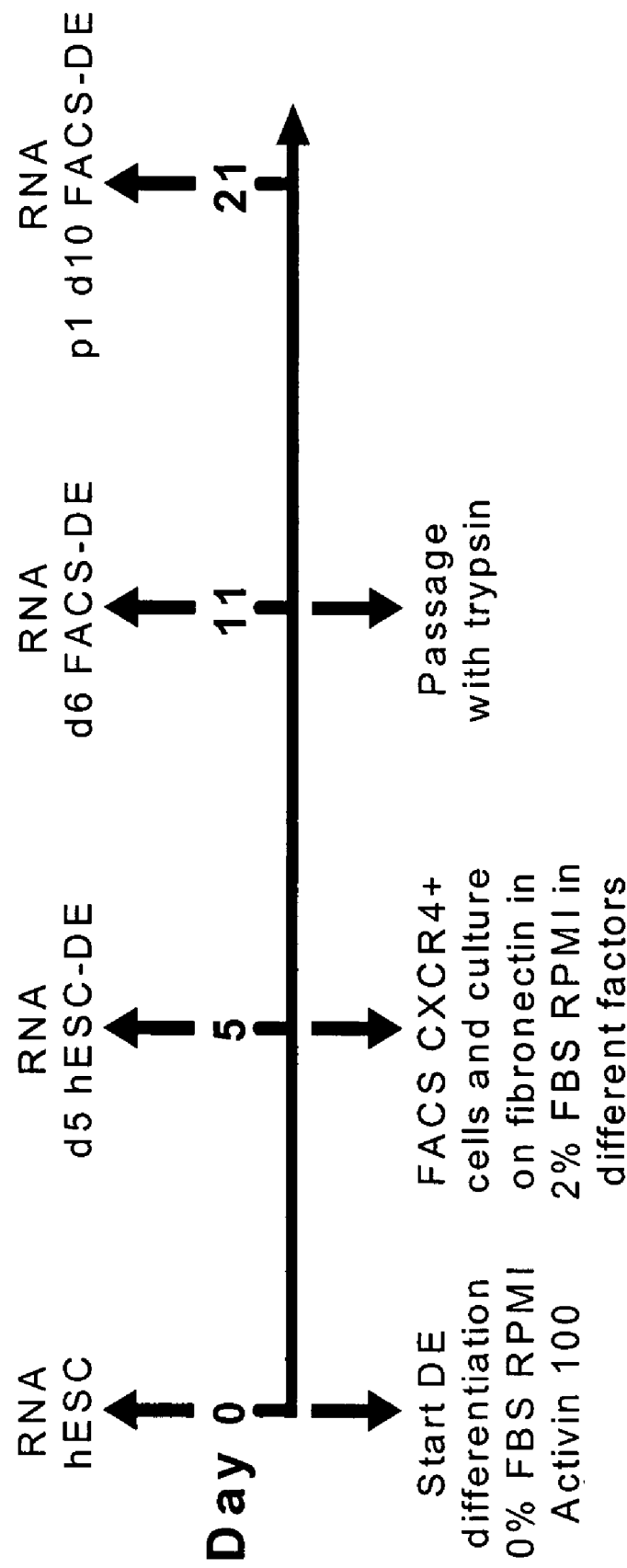
FIG. 36 is a diagram showing the cell differentiation, isolation and expansion procedure for definitive endoderm cells. The abbreviations are as follows: hESC refers to human embryonic stem cells; d5 hESC-DE refers to unpurified definitive endoderm cells; d6 FACS-DE refers to CXCR4 antibody/FACS purified definitive endoderm cells; and p1 d10 FACS-DE refers to purified definitive endoderm cells that have been passaged once and grown for 10 additional days subsequent to passage. RNA samples are taken and analyzed for marker expression at each of the indicated days.

FIG. 36 shows the design of a definitive endoderm purification/expansion experiment. In particular, definitive endoderm cells were differentiated from the 96$^{th}$ passage of hESC line CyT25 in the presence of 100 ng/ml activin A in low serum RMPI. The low serum RPMI contained 0% (v/v) fetal bovine serum (FBS) on day 1, 0.2% (v/v) FBS on day two and 2% serum on each day thereafter. After five days of differentiation, the cells were subjected to FACS purification using antibody against CXCR4 as described in previous Examples. The purified cell population was then cultured on IVF dishes coated with poly-ornithine and 10 µg/ml human fibronectin in RPMI containing 2% FBS under one of the following four growth factor conditions: no added factor (NF); 100 ng/ml activin A (A); 100 ng/ml activin A and 100 ng/ml IGF1 (AI); or 100 ng/ml activin A, 12 ng/ml bFGF and 10 ng/ml EGF (AFE). On day 11, the expanded definitive endoderm cells were passaged using the standard trypsinization method. Each of the cell cultures were then grown for an additional 10 days after passage (a total of 21 days subsequent to the first contact with activin A). Samples of mRNA were obtained at days 0, 5, 11 and 21 as indicated in FIG. 36.

Figure 37:
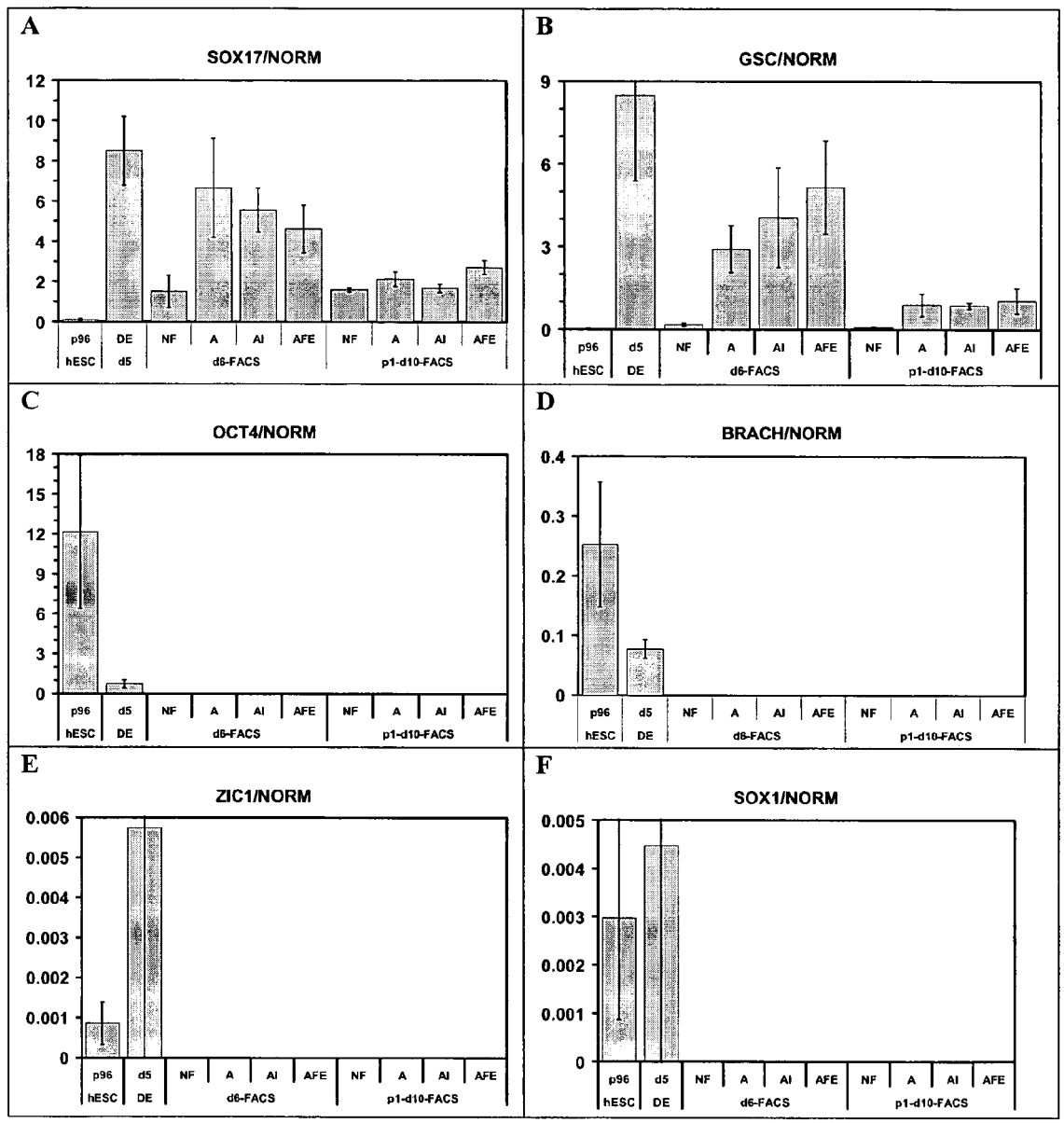
FIGS. 37A-F are bar charts showing the expression patterns of various embryonic cell lineage marker genes in cell cultures that have been differentiated to definitive endoderm then subsequently purified using the CXCR4 antibody in conjunction with fluorescence activated cell sorting (FACS). The abbreviations are as follows: p96 hESC refers to mRNA from the 96th passage of CyT25 human embryonic stem cells; d5 DE refers to mRNA from unpurified definitive endoderm cells on the fifth day of differentiation from p96 hESCs; NF d6-FACS refers to mRNA taken 11 days post differentiation from CXCR4 antibody/FACS purified definitive endoderm cells incubated in the absence of activin A; A refers to mRNA taken 11 days post differentiation from CXCR4 antibody/FACS purified definitive endoderm cells incubated in the presence of 100 ng/ml activin A; AI refers to mRNA taken 11 days post differentiation from CXCR4 antibody/FACS purified definitive endoderm cells incubated in the presence of 100 ng/ml activin A and 100 ng/ml IGF1; AFE refers to mRNA taken 11 days post differentiation from CXCR4 antibody/FACS purified definitive endoderm cells incubated in the presence of 100 ng/ml activin A, 12 ng/ml bFGF and 10 ng/ml EGF; NF p1-d10-FACS refers to mRNA taken 10 days post passage of CXCR4 antibody/FACS purified definitive endoderm cells incubated in the absence of activin A; A refers to mRNA taken 10 days post passage from CXCR4 antibody/FACS purified definitive endoderm cells incubated in the presence of 100 ng/ml activin A; AI refers to mRNA taken 10 days post passage from CXCR4 antibody/FACS purified definitive endoderm cells incubated in the presence of 100 ng/ml activin A and 100 ng/ml IGF1; and AFE refers to mRNA taken 10 days post passage from CXCR4 antibody/FACS purified definitive endoderm cells incubated in the presence of 100 ng/ml activin A, 12 ng/ml bFGF and 10 ng/ml EGF. Panel A—SOX17; B—GSC; C—OCT4; D—Brachyury; E—ZIC1; F—SOX1.

FIGS. 37A-E show the expression of marker genes for various embryonic cell types at each of the sample time points for each of the culture conditions. As shown in FIGS. 37A-B, the definitive endoderm markers SOX17 and GSC were highly expressed five day old unpurified definitive endoderm cultures but were not expressed in hESCs. This expression is in contrast to that of the hESC marker, OCT4 (FIG. 37C). Six days after the purification of definitive endoderm cells (day 11) the expression of SOX17 and GSC expression remained high in each of the cell cultures treated with growth factor(s) but not in cell cultures grown in the absence of activin A (FIG. 37A-B). A similar pattern of expression was observed for these markers 10 days after passage (day 21) (FIGS. 37A-B). No expression of mRNA for markers of hESCs (OCT4), mesoderm (brachyury), or ectoderm (ZIC1 and SOX1) was observed in any of the cell cultures subsequent to purification. This result indicates that purified definitive endoderm cells do not form hESCs or cells of the other two embryonic cell lineages even in the absence of activin A (FIGS. 37C-F).

The methods, compositions, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

REFERENCES

Numerous literature and patent references have been cited in the present patent application. Each and every reference that is cited in this patent application is incorporated by reference herein in its entirety.

For some references, the complete citation is in the body of the text. For other references the citation in the body of the text is by author and year, the complete citation being as follows:

Alexander, J., Rothenberg, M., Henry, G. L., and Stainier, D. Y. (1999). Casanova plays an early and essential role in endoderm formation in zebrafish. Dev Biol 215, 343-357.

Alexander, J., and Stainier, D. Y. (1999). A molecular pathway leading to endoderm formation in zebrafish. Curr Biol 9, 1147-1157.

Aoki, T. O., Mathieu, J., Saint-Etienne, L., Rebagliati, M. R., Peyrieras, N., and Rosa, F. M. (2002). Regulation of nodal signalling and mesendoderm formation by TARAM-A, a TGFbeta-related type I receptor. Dev Biol 241, 273-288.

Beck, S., Le Good, J. A., Guzman, M., Ben Haim, N., Roy, K., Beermann, F., and Constam, D. B. (2002). Extra-embryonic proteases regulate Nodal signalling during gastrulation. Nat Cell Biol 4, 981-985.

Beddington, R. S., Rashbass, P., and Wilson, V. (1992). Brachyury—a gene affecting mouse gastrulation and early organogenesis. Dev Suppl, 157-165.

Bongso, A., Fong, C. Y., Ng, S. C., and Ratnam, S. (1994). Isolation and culture of inner cell mass cells from human blastocysts. Hum Reprod 9, 2110-2117.

Chang, H., Brown, C. W., and Matzuk, M. M. (2002). Genetic analysis of the mammalian transforming growth factor-beta superfamily. Endocr Rev 23, 787-823.

Conlon, F. L., Lyons, K. M., Takaesu, N., Barth, K. S., Kispert, A., Herrmann, B., and Robertson, E. J. (1994). A primary requirement for nodal in the formation and maintenance of the primitive streak in the mouse. Development 120, 1919-1928.

Dougan, S. T., Warga, R. M., Kane, D. A., Schier, A. F., and Talbot, W. S. (2003). The role of the zebrafish nodal-related genes squint and cyclops in patterning of mesendoderm. Development 130, 1837-1851.

Feldman, B., Gates, M. A., Egan, E. S., Dougan, S. T., Rennebeck, G., Sirotkin, H. I., Schier, A. F., and Talbot, W. S. (1998). Zebrafish organizer development and germ-layer formation require nodal-related signals. Nature 395, 181-185.

Feng, Y., Broder, C. C., Kennedy, P. E., and Berger, E. A. (1996). HIV-1 entry cofactor: functional cDNA cloning of a seven-transmembrane, G protein-coupled receptor. Science 272, 872-877.

Futaki, S., Hayashi, Y., Yamashita, M., Yagi, K., Bono, H., Hayashizaki, Y., Okazaki, Y., and Sekiguchi, K. (2003). Molecular basis of constitutive production of basement membrane components: Gene expression profiles of engelbreth-holm-swarm tumor and F9 embryonal carcinoma cells. J Biol Chem.

Grapin-Botton, A., and Melton, D. A. (2000). Endoderm development: from patterning to organogenesis. Trends Genet 16, 124-130.

Harris, T. M., and Childs, G. (2002). Global gene expression patterns during differentiation of F9 embryonal carcinoma cells into parietal endoderm. Funct Integr Genomics 2, 105-119.

Hogan, B. L. (1996). Bone morphogenetic proteins in development. Curr Opin Genet Dev 6, 432-438.

Hogan, B. L. (1997). Pluripotent embryonic cells and methods of making same (U.S.A., Vanderbilt University).

Howe, C. C., Overton, G. C., Sawicki, J., Solter, D., Stein, P., and Strickland, S. (1988). Expression of SPARC/osteonectin transcript in murine embryos and gonads. Differentiation 37, 20-25.

Hudson, C., Clements, D., Friday, R. V., Stott, D., and Woodland, H. R. (1997). Xsox17alpha and -beta mediate endoderm formation in *Xenopus*. Cell 91, 397-405.

Imada, M., Imada, S., Iwasaki, H., Kume, A., Yamaguchi, H., and Moore, E. E. (1987). Fetomodulin: marker surface protein of fetal development which is modulatable by cyclic AMP. Dev Biol 122, 483-491.

Kanai-Azuma, M., Kanai, Y., Gad, J. M., Tajima, Y., Taya, C., Kurohmaru, M., Sanai, Y., Yonekawa, H., Yazaki, K., Tam, P. P., and Hayashi, Y. (2002). Depletion of definitive gut endoderm in Sox17-null mutant mice. Development 129, 2367-2379.

Katoh, M. (2002). Expression of human SOX7 in normal tissues and tumors. Int J Mol Med 9, 363-368.

Kikuchi, Y., Agathon, A., Alexander, J., Thisse, C., Waldron, S., Yelon, D., Thisse, B., and Stainier, D. Y. (2001). casanova encodes a novel Sox-related protein necessary and sufficient for early endoderm formation in zebrafish. Genes Dev 15, 1493-1505.

Kim, C. H., and Broxmeyer, H. E. (1999). Chemokines: signal lamps for trafficking of T and B cells for development and effector function. J Leukoc Biol 65, 6-15.

Kimelman, D., and Griffin, K. J. (2000). Vertebrate mesendoderm induction and patterning. Curr Opin Genet Dev 10, 350-356.

Kubo A, Shinozaki K, Shannon J M, Kouskoff V, Kennedy M, Woo S, Fehling H J, Keller G. (2004) Development of definitive endoderm from embryonic stem cells in culture. Development. 131, 1651-62.

Kumar, A., Novoselov, V., Celeste, A. J., Wolfman, N. M., ten Dijke, P., and Kuehn, M. R. (2001). Nodal signaling uses activin and transforming growth factor-beta receptor-regulated Smads. J Biol Chem 276, 656-661.

Labosky, P. A., Barlow, D. P., and Hogan, B. L. (1994a). Embryonic germ cell lines and their derivation from mouse primordial germ cells. Ciba Found Symp 182, 157-168; discussion 168-178.

Labosky, P. A., Barlow, D. P., and Hogan, B. L. (1994b). Mouse embryonic germ (EG) cell lines: transmission through the germline and differences in the methylation imprint of insulin-like growth factor 2 receptor (Igf2r) gene compared with embryonic stem (ES) cell lines. Development 120, 3197-3204.

Lickert, H., Kutsch, S., Kanzler, B., Tamai, Y., Taketo, M. M., and Kemler, R. (2002). Formation of multiple hearts in mice following deletion of beta-catenin in the embryonic endoderm. Dev Cell 3, 171-181.

Lu, C. C., Brennan, J., and Robertson, E. J. (2001). From fertilization to gastrulation: axis formation in the mouse embryo. Curr Opin Genet Dev 11, 384-392.

Ma, Q., Jones, D., and Springer, T. A. (1999). The chemokine receptor CXCR4 is required for the retention of B lineage and granulocytic precursors within the bone marrow microenvironment. Immunity 10, 463-471.

McGrath K E, Koniski A D, Maltby K M, McGann J K, Palis J. (1999) Embryonic expression and function of the chemokine SDF-1 and its receptor, CXCR4. Dev Biol. 213, 442-56.

Miyazono, K., Kusanagi, K., and Inoue, H. (2001). Divergence and convergence of TGF-beta/BMP signaling. J Cell Physiol 187, 265-276.

Nagasawa, T., Hirota, S., Tachibana, K., Takakura, N., Nishikawa, S., Kitamura, Y., Yoshida, N., Kikutani, H., and Kishimoto, T. (1996). Defects of B-cell lymphopoiesis and bone-marrow myelopoiesis in mice lacking the CXC chemokine PBSF/SDF-1. Nature 382, 635-638.

Niwa, H. (2001). Molecular mechanism to maintain stem cell renewal of ES cells. Cell Struct Funct 26, 137-148.

Ogura, H., Aruga, J., and Mikoshiba, K. (2001). Behavioral abnormalities of Zic1 and Zic2 mutant mice: implications as models for human neurological disorders. Behav Genet 31, 317-324.

Reubinoff, B. E., Pera, M. F., Fong, C. Y., Trounson, A., and Bongso, A. (2000). Embryonic stem cell lines from human blastocysts: somatic differentiation in vitro. Nat Biotechnol 18, 399-404.

Rodaway, A., and Patient, R. (2001). Mesendoderm. an ancient germ layer? Cell 105, 169-172.

Rodaway, A., Takeda, H., Koshida, S., Broadbent, J., Price, B., Smith, J. C., Patient, R., and Holder, N. (1999). Induction of the mesendoderm in the zebrafish germ ring by yolk cell-derived TGF-beta family signals and discrimination of mesoderm and endoderm by FGF. Development 126, 3067-3078.

Rohr, K. B., Schulte-Merker, S., and Tautz, D. (1999). Zebrafish zic1 expression in brain and somites is affected by BMP and hedgehog signalling. Mech Dev 85, 147-159.

Schier, A. F. (2003). Nodal signaling in vertebrate development. Annu Rev Cell Dev Biol 19, 589-621.

Schoenwolf, G. C., and Smith, J. L. (2000). Gastrulation and early mesodermal patterning in vertebrates. Methods Mol Biol 135, 113-125.

Shamblott, M. J., Axelman, J., Wang, S., Bugg, E. M., Littlefield, J. W., Donovan, P. J., Blumenthal, P. D., Huggins, G. R., and Gearhart, J. D. (1998). Derivation of pluripotent stem cells from cultured human primordial germ cells. Proc Natl Acad Sci USA 95, 13726-13731.

Shapiro, A. M., Lakey, J. R., Ryan, E. A., Korbutt, G. S., Toth, E., Warnock, G. L., Kneteman, N. M., and Rajotte, R. V. (2000). Islet transplantation in seven patients with type 1 diabetes mellitus using a glucocorticoid-free immunosuppressive regimen. N Engl J Med 343, 230-238.

Shapiro, A. M., Ryan, E. A., and Lakey, J. R. (2001a). Pancreatic islet transplantation in the treatment of diabetes mellitus. Best Pract Res Clin Endocrinol Metab 15, 241-264.

Shapiro, J., Ryan, E., Warnock, G. L., Kneteman, N. M., Lakey, J., Korbutt, G. S., and Rajotte, R. V. (2001b). Could fewer islet cells be transplanted in type 1 diabetes? Insulin independence should be dominant force in islet transplantation. Bmj 322, 861.

Shiozawa, M., Hiraoka, Y., Komatsu, N., Ogawa, M., Sakai, Y., and Aiso, S. (1996). Cloning and characterization of Xenopus laevis xSox7 cDNA. Biochim Biophys Acta 1309, 73-76.

Smith, J. (1997). Brachyury and the T-box genes. Curr Opin Genet Dev 7, 474-480.

Smith, J. C., Armes, N. A., Conlon, F. L., Tada, M., Umbhauer, M., and Weston, K. M. (1997). Upstream and downstream from Brachyury, a gene required for vertebrate mesoderm formation. Cold Spring Harb Symp Quant Biol 62, 337-346.

Takash, W., Canizares, J., Bonneaud, N., Poulat, F., Mattei, M. G., Jay, P., and Berta, P. (2001). SOX7 transcription factor: sequence, chromosomal localisation, expression, transactivation and interference with Wnt signalling. Nucleic Acids Res 29, 4274-4283.

Taniguchi, K., Hiraoka, Y., Ogawa, M., Sakai, Y., Kido, S., and Aiso, S. (1999). Isolation and characterization of a mouse SRY-related cDNA, mSox7. Biochim Biophys Acta 1445, 225-231.

Technau, U. (2001). Brachyury, the blastopore and the evolution of the mesoderm. Bioessays 23, 788-794.

Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147.

Tremblay, K. D., Hoodless, P. A., Bikoff, E. K., and Robertson, E. J. (2000). Formation of the definitive endoderm in mouse is a Smad2-dependent process. Development 127, 3079-3090.

Vandesompele, J., De Preter, K., Pattyn, F., Poppe, B., Van Roy, N., De Paepe, A., and Speleman, F. (2002). Accurate normalization of real-time quantitative RT-PCR data by geometric averaging of multiple internal control genes. Genome Biol 3, RESEARCH0034.

Varlet, I., Collignon, J., and Robertson, E. J. (1997). nodal expression in the primitive endoderm is required for specification of the anterior axis during mouse gastrulation. Development 124, 1033-1044.

Vincent, S. D., Dunn, N. R., Hayashi, S., Norris, D. P., and Robertson, E. J. (2003). Cell fate decisions within the mouse organizer are governed by graded Nodal signals. Genes Dev 17, 1646-1662.

Weiler-Guettler, H., Aird, W. C., Rayburn, H., Husain, M., and Rosenberg, R. D. (1996). Developmentally regulated gene expression of thrombomodulin in postimplantation mouse embryos. Development 122, 2271-2281.

Weiler-Guettler, H., Yu, K., Soff, G., Gudas, L. J., and Rosenberg, R. D. (1992). Thrombomodulin gene regulation by cAMP and retinoic acid in F9 embryonal carcinoma cells. Proceedings Of The National Academy Of Sciences Of The United States Of America 89, 2155-2159.

Wells, J. M., and Melton, D. A. (1999). Vertebrate endoderm development. Annu Rev Cell Dev Biol 15, 393-410.

Wells, J. M., and Melton, D. A. (2000). Early mouse endoderm is patterned by soluble factors from adjacent germ layers. Development 127, 1563-1572.

Willison, K. (1990). The mouse Brachyury gene and mesoderm formation. Trends Genet 6, 104-105.

Zhao, G. Q. (2003). Consequences of knocking out BMP signaling in the mouse. Genesis 35, 43-56.

Zhou, X., Sasaki, H., Lowe, L., Hogan, B. L., and Kuehn, M. R. (1993). Nodal is a novel TGF-beta-like gene expressed in the mouse node during gastrulation. Nature 361, 543-547.

What is claimed is:

1. A method of expanding definitive endoderm cells in culture, said method comprising the steps of:
   (a) obtaining a cell culture comprising definitive endoderm cells;
   (b) isolating at least some of the definitive endoderm cells from at least some of the other cells in the cell culture, thereby producing a cell population enriched in definitive endoderm cells; and
   (c) culturing said cell population enriched in definitive endoderm cells under conditions that permit the expansion of said definitive endoderm cells.

2. The method of claim 1, wherein said definitive endoderm cells are multipotent cells that can differentiate into cells of the gut tube or organs derived therefrom.

3. The method of claim 1, wherein said definitive endoderm cells are human definitive endoderm cells.

4. The method of claim 3, wherein said definitive endoderm cells are derived from human embryonic stem cells (hESCs).

5. The method of claim 4, wherein the obtaining step comprises contacting hESCs with at least one growth factor from the TGFβ superfamily so as to permit differentiation of at least some of said hESCs to definitive endoderm cells.

6. The method of claim 5, wherein said at least one growth factor from the TGFβ superfamily comprises activin A.

7. The method of claim 1, wherein the step of obtaining said cell culture comprising definitive endoderm further comprises obtaining a portion of an existing definitive endoderm culture.

8. The method of claim 1, wherein said cell population enriched in definitive endoderm cells is substantially free of cells other than definitive endoderm cells.

9. The method of claim 1, wherein said cell population enriched in definitive endoderm cells comprises at least 96% definitive endoderm cells.

10. The method of claim 1, wherein said cell population enriched in definitive endoderm cells comprises at least 98% definitive endoderm cells.

11. The method of claim 1, wherein said cell population enriched in definitive endoderm cells comprises 100% definitive endoderm cells.

12. The method of claim 1, wherein said isolating step comprises providing said cell culture with a reagent which binds to a marker expressed in said definitive endoderm cells but which is not substantially expressed in said other cells present in the cell culture, and separating said definitive endoderm cells bound to said reagent from said other cells present in the cell culture, thereby producing a cell population enriched in definitive endoderm cells.

13. The method of claim 12, wherein said marker is CXCR4.

14. The method of claim 12, wherein said reagent is an antibody.

15. The method of claim 12, wherein said definitive endoderm cells bound to said reagent are separated from said other cells present in the cell culture by fluorescence activated cell sorting (FACS).

16. The method of claim 1, wherein said isolating step comprises separating fluorescently-labeled definitive endoderm cells from unlabeled cells.

17. The method of claim 1, wherein said culturing step comprises plating said population enriched in definitive endoderm cells or a portion thereof.

18. The method of claim 17, wherein said population enriched in definitive endoderm cells or a portion thereof is plated on a surface coated with human fibronectin.

19. The method of claim 18, wherein said surface is coated with poly-ornithine.

20. The method of claim 1, wherein said culturing step comprises incubating said population enriched in definitive endoderm cells or a portion thereof in a medium comprising 2% (v/v) serum.

21. The method of claim 1, wherein said culturing step comprises incubating said population enriched in definitive endoderm cells or a portion thereof in a medium comprising 2% to 20% (v/v) serum.

22. The method of claim 1, wherein said culturing step comprises incubating said population enriched in definitive endoderm cells or a portion thereof in a medium comprising 0% to 2% (v/v) serum.

23. The method of claim 1, wherein said culturing step comprises incubating said population enriched in definitive endoderm cells or a portion thereof in a medium comprising at least one growth factor.

24. The method of claim 23, wherein said at least one growth factor is a growth factor from the TGFβ superfamily of growth factors.

25. The method of claim 24, wherein said at least one growth factor from the TGFβ superfamily of growth factors comprises activin A.

26. The method of claim 25, wherein said activin A is present in said medium at a concentration ranging from 1 ng/ml to 5000 ng/ml.

27. The method of claim 23, wherein said at least one growth factor comprises IGF1.

28. The method of claim 27, wherein said IGF1 is present in said medium at a concentration ranging from 1 ng/ml to 5000 ng/ml.

29. The method of claim 23, wherein said at least one growth factor comprises a combination of activin A and IGF1.

30. The method of claim 23, wherein said at least one growth factor comprises bFGF.

31. The method of claim 30, wherein said bFGF is present in said medium at a concentration ranging from 1 ng/ml to 5000 ng/ml.

32. The method of claim 23, wherein said at least one growth factor comprises EGF.

33. The method of claim 32, wherein said EGF is present in said medium at a concentration ranging from 1 ng/ml to 5000 ng/ml.

34. The method of claim 23, wherein said at least one growth factor comprises a combination of activin A, bFGF and EGF.

35. The method of claim 3, wherein the other cells in the cell culture are extraembryonic endoderm cells.

36. The method of claim 3, wherein the other cells in the cell culture are embryonic stem cells.

37. The method of claim 1, wherein the step of culturing said definitive endoderm cells under conditions that permit the expansion of said definitive endoderm cells comprises passaging said definitive endoderm cells, thereby producing a plurality of cell cultures comprising definitive endoderm cells.

38. The method of claim 37, wherein passaging said definitive endoderm cells comprises providing at least one enzyme to said cell culture.

39. The method of claim 38, wherein said at least one enzyme comprises at least one protease.

40. The method of claim 37, wherein passaging said definitive endoderm cells comprises mechanically disrupting contacts between said definitive endoderm cells.

* * * * *

UNITED STATES PATENT AND TRADEMARK OFFICE
CERTIFICATE OF CORRECTION

PATENT NO. : 7,625,753 B2
APPLICATION NO. : 11/317387
DATED : December 1, 2009
INVENTOR(S) : Olivia Kelly et al.

It is certified that error appears in the above-identified patent and that said Letters Patent is hereby corrected as shown below:

Title Page (Item 56) Page 2, Col. 2, Line 34, under Other Publications, change "Day" to --Dev--;

(Item 56) Page 2, Col. 2, Line 36, under Other Publications, change "C.V.," to --C.Y.,--;

(Item 56) Page 4, Col. 1, Line 52, under Other Publications, change "Ada" to --Acta--;

In the Drawings

On Sheet 29 of 39 (Figure 29), Line 13-14 (Approx.), please change "0 5%" to --0.5%--.

Signed and Sealed this

Twenty-second Day of June, 2010

*David J. Kappos*
*Director of the United States Patent and Trademark Office*

UNITED STATES PATENT AND TRADEMARK OFFICE
CERTIFICATE OF CORRECTION

| | | |
|---|---|---|
| PATENT NO. | : 7,625,753 B2 | Page 1 of 1 |
| APPLICATION NO. | : 11/317387 | |
| DATED | : December 1, 2009 | |
| INVENTOR(S) | : Kelly et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 183 days.

Signed and Sealed this

Second Day of November, 2010

David J. Kappos
*Director of the United States Patent and Trademark Office*

SEQUENCE LISTING

<160> NUMBER OF SEQ ID NOS: 2

<210> SEQ ID NO 1
<211> LENGTH: 1245
<212> TYPE: DNA
<213> ORGANISM: Homo sapiens

<400> SEQUENCE: 1

```
atgagcagcc cggatgcggg atacgccagt gacgaccaga gccagaccca gagcgcgctg      60
cccgcggtga tggccgggct ggccccctgc ccctgggccg agtcgctgag ccccatcggg     120
gacatgaagg tgaagggcga ggcgccggcg aacagcggag caccggccgg ggccgcgggc     180
cgagccaagg gcgagtcccg tatccggcgg ccgatgaacg ctttcatggt gtgggctaag     240
gacgagcgca agcggctggc gcagcagaat ccagacctgc acaacgccga gttgagcaag     300
atgctgggca agtcgtggaa ggcgctgacg ctggcggaga gcggcccctt cgtggaggag     360
gcagagcggc tgcgcgtgca gcacatgcag gaccacccca actacaagta ccggccgcgg     420
cggcgcaagc aggtgaagcg gctgaagcgg gtggagggcg gcttcctgca cggcctggct     480
gagccgcagg cggccgcgct gggccccgag gcggccgcg tggccatgga cggcctgggc      540
ctccagttcc ccgagcaggg cttccccgcc ggcccgccgc tgctgcctcc gcacatgggc     600
ggccactacc gcgactgcca gagtctgggc gcgcctccgc tcgacggcta cccgttgccc     660
acgcccgaca cgtccccgct ggacggcgtg gaccccgacc cggctttctt cgccgccccg     720
atgcccgggg actgcccggc ggccggcacc tacagctacg cgcaggtctc ggactacgct     780
ggccccccgg agcctcccgc cggtcccatg caccccccgac tcggcccaga gcccgcgggt     840
ccctcgattc cgggcctcct ggcgccaccc agcgcccttc acgtgtacta cggcgcgatg     900
ggctcgcccg gggcgggcgg cgggcgcggc ttccagatgc agccgcaaca ccagcaccag     960
caccagcacc agcaccaccc ccgggcccc ggacagccgt cgcccccctcc ggaggcactg     1020
ccctgccggg acggcacgga ccccagtcag ccgccgagc tcctcgggga ggtggaccgc     1080
acggaatttg aacagtatct gcacttcgtg tgcaagcctg agatgggcct ccctaccag     1140
gggcatgact ccggtgtgaa tctccccgac agcacgggg ccatttcctc ggtggtgtcc     1200
gacgccagct ccgcggtata ttactgcaac tatcctgacg tgtga                    1245
```

<210> SEQ ID NO 2
<211> LENGTH: 414
<212> TYPE: PRT
<213> ORGANISM: Homo sapiens

<400> SEQUENCE: 2

```
Met Ser Ser Pro Asp Ala Gly Tyr Ala Ser Asp Asp Gln Ser Gln Thr
 1               5                  10                  15

Gln Ser Ala Leu Pro Ala Val Met Ala Gly Leu Gly Pro Cys Pro Trp
            20                  25                  30

Ala Glu Ser Leu Ser Pro Ile Gly Asp Met Lys Val Lys Gly Glu Ala
        35                  40                  45

Pro Ala Asn Ser Gly Ala Pro Ala Gly Ala Ala Gly Arg Ala Lys Gly
    50                  55                  60

Glu Ser Arg Ile Arg Arg Pro Met Asn Ala Phe Met Val Trp Ala Lys
65                  70                  75                  80

Asp Glu Arg Lys Arg Leu Ala Gln Gln Asn Pro Asp Leu His Asn Ala
                85                  90                  95
```

-continued

```
Glu Leu Ser Lys Met Leu Gly Lys Ser Trp Lys Ala Leu Thr Leu Ala
            100                 105                 110
Glu Lys Arg Pro Phe Val Glu Glu Ala Glu Arg Leu Arg Val Gln His
            115                 120                 125
Met Gln Asp His Pro Asn Tyr Lys Tyr Arg Pro Arg Arg Arg Lys Gln
            130                 135                 140
Val Lys Arg Leu Lys Arg Val Glu Gly Gly Phe Leu His Gly Leu Ala
145                 150                 155                 160
Glu Pro Gln Ala Ala Ala Leu Gly Pro Glu Gly Arg Val Ala Met
                165                 170                 175
Asp Gly Leu Gly Leu Gln Phe Pro Glu Gln Gly Phe Pro Ala Gly Pro
            180                 185                 190
Pro Leu Leu Pro Pro His Met Gly Gly His Tyr Arg Asp Cys Gln Ser
            195                 200                 205
Leu Gly Ala Pro Pro Leu Asp Gly Tyr Pro Leu Pro Thr Pro Asp Thr
            210                 215                 220
Ser Pro Leu Asp Gly Val Asp Pro Asp Pro Ala Phe Phe Ala Ala Pro
225                 230                 235                 240
Met Pro Gly Asp Cys Pro Ala Ala Gly Thr Tyr Ser Tyr Ala Gln Val
                245                 250                 255
Ser Asp Tyr Ala Gly Pro Pro Glu Pro Pro Ala Gly Pro Met His His Pro
            260                 265                 270
Arg Leu Gly Pro Glu Pro Ala Gly Pro Ser Ile Pro Gly Leu Leu Ala
            275                 280                 285
Pro Pro Ser Ala Leu His Val Tyr Tyr Gly Ala Met Gly Ser Pro Gly
            290                 295                 300
Ala Gly Gly Gly Arg Gly Phe Gln Met Gln Pro Gln His Gln His Gln
305                 310                 315                 320
His Gln His Gln His His Pro Pro Gly Pro Gly Gln Pro Ser Pro Pro
                325                 330                 335
Pro Glu Ala Leu Pro Cys Arg Asp Gly Thr Asp Pro Ser Gln Pro Ala
            340                 345                 350
Glu Leu Leu Gly Glu Val Asp Arg Thr Glu Phe Glu Gln Tyr Leu His
            355                 360                 365
Phe Val Cys Lys Pro Glu Met Gly Leu Pro Tyr Gln Gly His Asp Ser
            370                 375                 380
Gly Val Asn Leu Pro Asp Ser His Gly Ala Ile Ser Ser Val Val Ser
385                 390                 395                 400
Asp Ala Ser Ser Ala Val Tyr Tyr Cys Asn Tyr Pro Asp Val
                405                 410
```